United States Patent
Nieman et al.

(10) Patent No.: US 11,939,302 B2
(45) Date of Patent: Mar. 26, 2024

(54) COMPOUNDS FOR THE TREATMENT OF ALZHEIMER'S DISEASE

(71) Applicant: The Governors of the University of Alberta, Edmonton (CA)

(72) Inventors: James A. Nieman, Sherwood Park (CA); Jack Jhamandas, Edmonton (CA); Bing Bai, Edmonton (CA); Alexandr Belovodskiy, Edmonton (CA); Wen Fu, Edmonton (CA); Mostofa Hena, Edmonton (CA); Michael Houghton, Danville, CA (US); Appan Srinivas Kandadai, Edmonton (CA); Ryoichi Kimura, Sanyo-Onoda (JP); Kamlesh Kumar Sahu, Edmonton (CA); D. Lorne Tyrrell, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 176 days.

(21) Appl. No.: 17/505,250

(22) Filed: Oct. 19, 2021

(65) Prior Publication Data
US 2022/0119356 A1  Apr. 21, 2022

Related U.S. Application Data

(60) Provisional application No. 63/094,777, filed on Oct. 21, 2020.

(51) Int. Cl.
*A61K 31/55* (2006.01)
*A61P 25/28* (2006.01)
*C07D 241/44* (2006.01)
*C07D 243/12* (2006.01)
*C07D 243/14* (2006.01)
*C07D 403/12* (2006.01)

(52) U.S. Cl.
CPC ............ *C07D 243/12* (2013.01); *A61P 25/28* (2018.01); *C07D 241/44* (2013.01); *C07D 243/14* (2013.01); *C07D 403/12* (2013.01)

(58) Field of Classification Search
CPC ............................... A61P 25/28; A61K 31/55
See application file for complete search history.

(56) References Cited

FOREIGN PATENT DOCUMENTS

CA    2325389    12/1999

OTHER PUBLICATIONS

Sun et al., (1996), "Synthesis of Chiral I-(2C-Amino-2C-carboxyethyl)-I,4-dihydro-6,7-quinoxaline-2,3-diones:R-Amino-3-hydroxy-5-methyl-4-isoxazolepropionate Receptor Agonists and Antagonists", J. Med. Chem. vol. 39, pp. 4430-4438.

*Primary Examiner* — Bruck Kifle
(74) *Attorney, Agent, or Firm* — Rudy J. Ng; Bozicevic, Field & Francis LLP

(57) ABSTRACT

The present disclosure provides compounds that are amylin receptor antagonist compounds, compositions that include the subject compounds, methods for preparing and using the amylin receptor antagonists, and compositions containing the amylin receptor antagonists for treating, preventing, or ameliorating Alzheimer's disease. Aspects of the present disclosure include a method of inhibiting activity of an amylin receptor by administering to a subject in need thereof a therapeutically effective amount of an amylin receptor antagonist.

20 Claims, 8 Drawing Sheets

Compound 1 (also known as Cmpd 1)

Compound 10 (also known as Cmpd 10)

COMPOUNDS FOR THE TREATMENT OF ALZHEIMER'S DISEASE

CROSS-REFERENCE TO RELATED APPLICATIONS

This application claims the benefit of U.S. Provisional Application No. 63/094,777, filed Oct. 21, 2020, the disclosure of which is incorporated herein by reference.

INTRODUCTION

Alzheimer's disease is the most common form of dementia that is characterized by deposition of amyloid β-protein (Aβ or Abeta) intra- and extracellularly within cortical and limbic brain structures critical for memory and cognitive functions (Selkoe, 1994 and 2013; Hardy et al., 2002). A central question in Alzheimer's disease research is whether the amyloid protein is a cause or a consequence of the disease. Presently, it appears that the likely answer is both (Hardy, 2009). Evidence strongly supports a role for Aβ in the pathogenesis of Alzheimer's disease, namely: a) Alzheimer's disease associated with inherited Amyloid Precursor Protein (APP) mutations; b) neurotoxicity of soluble oligomeric Aβ when applied to neurons; and c) APP over-expressing mice that recapitulate certain neuropathological and behavioral features of Alzheimer's disease (Liu et al., 2012; Bateman et al., 2012; Patel et al., 2012; Danysz et al., 2012). On the other hand, adverse events in clinical trials for Alzheimer's disease using Aβ vaccine-based therapy, and the subsequent failure of monoclonal antibody therapies and inhibitors of the Aβ generating gamma-secretase enzyme in improving cognitive functions in patients have forced reconsideration of these approaches as disease-modifying treatment strategies in Alzheimer's disease (Liu et al., 2012). Nonetheless, it is hard to imagine a definitive treatment that will not serve to ameliorate in some form the neurotoxic effects of Aβ, since this is a key "upstream" event in Alzheimer's disease pathogenesis (as established by alterations in CSF Aβ levels decades before clinical onset) (Bateman et al., 2012).

Multiple receptors have been implicated in mediating Aβ disruption of neuronal and synaptic processes in Alzheimer's disease, and thus identified as potential targets for developing anti-Aβ therapies (Patel et al., 2012; Danysz et al., 2012). The amylin receptor, comprised of heterodimers of the calcitonin receptor with receptor activity-modifying proteins, serves as a portal for the expression of deleterious effects of Aβ and human amylin (Fu et al., 2012). Amylin is a 37-amino acid peptide hormone that is co-secreted with insulin by beta cells of the pancreas that control glucose levels in blood.

Both Aβ and human amylin are amyloidogenic peptides which share structure-functional relationships; for example, both peptides aggregate and form soluble and insoluble oligomeric intermediates. Amylin has the propensity to aggregate and form amyloid oligomers and fibrils in the pancreas in type 2 diabetes (Westermark et al., 2011) and in Alzheimer's disease brains (Abedini et al., 2013). Aβ and human amylin cause dysfunction and death of neurons preferentially affected in Alzheimer's disease (Jhamandas et al., 2011; 2004). Neurotoxic effects of human amylin and Aβ are expressed through the amylin receptor 3 subtype (AMY3).

Amylin receptor antagonists, such as AC253 (a 24-amino acid peptide), are neuroprotective against Aβ toxicity (Jhamandas et al., 2004; 2011; 2012). Down-regulation of amylin receptor gene expression using siRNA mitigates oligomerized Aβ-induced toxicity (Jhamandas et al., 2011). In Alzheimer's disease transgenic model mice (TgCRND8) which over-express Aβ, amylin receptor was up-regulated within specific brain regions that demonstrate an increased burden of amyloid beta deposits (Jhamandas et al., 2011). Blockade of the amylin receptor with AC253 can reverse impairment of Aβ- or human amylin-induced depression of long-term potentiation, a cellular surrogate of memory, as observed in the hippocampus of Alzheimer's disease mice (TgCRND8) (Kimura et al., 2012). Similar benefits have been reported with pramlintide, a synthetic non-amyloidogenic analog of amylin. While data support a neuroprotective role for this compound, it appears to act as an amylin receptor antagonist rather than an agonist (Kimura et al., 2016). Although amylin receptor antagonist AC253 peptide has therapeutic potential in Alzheimer's disease, it suffers from poor enzymatic stability and an inability to penetrate the blood brain barrier.

SUMMARY

The present disclosure provides compounds that are amylin receptor antagonists, compositions that include the subject compounds, and methods for preparing and using the amylin receptor antagonists and the compositions for treating, preventing, or ameliorating Alzheimer's disease.

Aspects of the present disclosure include a method of inhibiting activity of an amylin receptor. The method includes administering to a subject in need thereof, a therapeutically effective amount of a compound of formula (I):

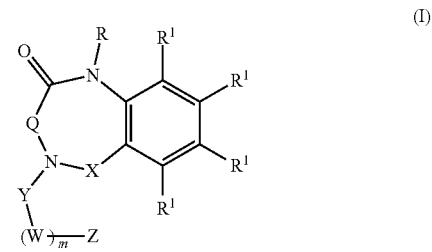

(I)

wherein:
R is selected from the group consisting of —H, $C_1$-$C_6$-alkyl, and substituted $C_1$-$C_6$-alkyl;
each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;
each $R^2$ is independently selected from the group consisting of —H, $C_1$-$C_6$-alkyl, and substituted $C_1$-$C_6$-alkyl;
each W is selected from the group consisting of —$CH_2$—, —$CHR^3$— and —$CR^3R^4$—;
$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo;
m is selected from 1, 2 or 3;
Q is selected from the group consisting of —$CH_2$—, —C(═O)—, —$CH_2$C(═O)—, and —$CH_2CH_2$—;

X is present or absent, and if present is selected from the group consisting of —CH$_2$— and —C(=O)—;

Y is selected from the group consisting of —CH$_2$—, and —C(=O)—;

Z is selected from the group consisting of —OR$^5$, halogen, —CN, —NR$^5$R$^5$, —NHC(=O)R$^5$, —NHC(=O)NR$^5$R$^5$, aryl, and heteroaryl; and each R$^5$ is independently selected from the group consisting of —H, C$_1$-C$_6$-alkyl, substituted C$_1$-C$_6$-alkyl, aryl, substituted aryl, heteroaryl, and substituted heteroaryl;

or an enantiomer, a mixture of enantiomers, a mixture of two or more diastereomers, a tautomer, a mixture of two or more tautomers, or an isotopic variant thereof;

or a pharmaceutically acceptable salt, solvate, or hydrate thereof.

In certain embodiments, the amylin receptor is an AMY3 receptor.

In certain embodiments, the administering is effective for treating a disease mediated through activity of the amylin receptor. In certain embodiments, the disease is Alzheimer's disease.

In certain embodiments, the compound is of formula (II):

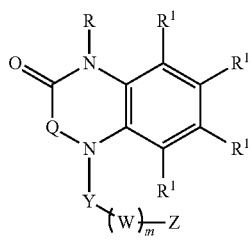

(II)

wherein:
R is selected from the group consisting of —H and C$_1$-C$_6$-alkyl;

each R$^1$ is independently selected from the group consisting of —H, halogen, C$_1$-C$_6$-alkyl, substituted C$_1$-C$_6$-alkyl, C$_3$-C$_6$-cycloalkyl, substituted C$_3$-C$_6$-cycloalkyl, —OR$^2$, heterocyclyl, substituted heterocyclyl, aryl, substituted aryl, heteroaryl, and substituted heteroaryl;

each R$^2$ is independently selected from the group consisting of —H, and C$_1$-C$_6$-alkyl;

each W is selected from the group consisting of —CH$_2$—, —CHR$^3$— and —CR$^3$R$^4$—;

R$^3$ and R$^4$ are independently selected from the group consisting of halogen, C$_1$-C$_6$-alkyl, substituted C$_1$-C$_6$-alkyl, C$_3$-C$_6$-cycloalkyl, substituted C$_3$-C$_6$-cycloalkyl, heterocyclyl, substituted heterocyclyl, aryl, substituted aryl, heteroaryl, substituted heteroaryl, fused-heterocycle, and substituted fused-heterocycle, or together R$^3$ and R$^4$ comprise a carbocycle, substituted carbocycle or oxo;

m is selected from 1, 2 or 3;

Q is selected from the group consisting of —CH$_2$—, —C(=O)— and —CH$_2$C(=O)—;

Y is selected from the group consisting of —CH$_2$—, and —C(=O)—;

Z is selected from the group consisting of —OR$^5$, -halogen, —NR$^5$R$^5$, —NHC(=O)R$^5$, —NHC(=O)NR$^5$R$^5$, aryl, and heteroaryl; and each R$^5$ is independently selected from the group consisting of —H, C$_1$-C$_6$-alkyl, substituted C$_1$-C$_6$-alkyl, aryl, substituted aryl, heteroaryl, and substituted heteroaryl;

or an enantiomer, a mixture of enantiomers, a mixture of two or more diastereomers, a tautomer, a mixture of two or more tautomers, or an isotopic variant thereof;

or a pharmaceutically acceptable salt, solvate, or hydrate thereof.

In certain embodiments, the compound is of formula (III):

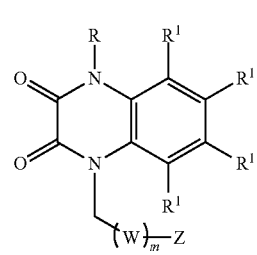

(III)

wherein:
R is selected from the group consisting of —H and C$_1$-C$_6$-alkyl;

each R$^1$ is independently selected from the group consisting of —H, halogen, C$_1$-C$_6$-alkyl, substituted C$_1$-C$_6$-alkyl, C$_3$-C$_6$-cycloalkyl, substituted C$_3$-C$_6$-cycloalkyl, —OR$^2$, heterocyclyl, substituted heterocyclyl, aryl, substituted aryl, heteroaryl, and substituted heteroaryl;

each R$^2$ is independently selected from the group consisting of —H, and C$_1$-C$_6$-alkyl;

each W is selected from the group consisting of —CH$_2$—, —CHR$^3$— and —CR$^3$R$^4$—;

R$^3$ and R$^4$ are independently selected from the group consisting of halogen, C$_1$-C$_6$-alkyl, substituted C$_1$-C$_6$-alkyl, C$_3$-C$_6$-cycloalkyl, substituted C$_3$-C$_6$-cycloalkyl, heterocyclyl, substituted heterocyclyl, aryl, substituted aryl, heteroaryl, substituted heteroaryl, fused-heterocycle, and substituted fused-heterocycle, or together R$^3$ and R$^4$ comprise a carbocycle, substituted carbocycle or oxo;

m is selected from 1, 2 or 3;

Z is selected from the group consisting of —OR$^5$, halogen, —NR$^5$R$^5$, —NHC(=O)R$^5$, —NHC(=O)NR$^5$R$^5$, aryl, and heteroaryl; and each R$^5$ is independently selected from the group consisting of —H, C$_1$-C$_6$-alkyl, substituted C$_1$-C$_6$-alkyl, aryl, substituted aryl, heteroaryl, and substituted heteroaryl;

or an enantiomer, a mixture of enantiomers, a mixture of two or more diastereomers, a tautomer, a mixture of two or more tautomers, or an isotopic variant thereof;

or a pharmaceutically acceptable salt, solvate, or hydrate thereof.

In certain embodiments, R is —H or —CH$_3$.

In certain embodiments, each R$^1$ is selected from —H, —CH$_3$, —F, —Cl, —CF$_3$, and heteroaryl.

In certain embodiments, each R$^1$ is selected from —H, —CH$_3$, —F, —Cl, —CF$_3$, and pyridyl.

In certain embodiments, R$^1$ is —H.

In certain embodiments, m is 1. In certain embodiments, m is 2.

In certain embodiments, R$^3$ and R$^4$ are independently selected from the group consisting of halogen, C$_1$-C$_6$-alkyl, substituted C$_1$-C$_6$-alkyl, C$_3$-C$_6$-cycloalkyl, substituted C$_3$-C$_6$-cycloalkyl, heteroaryl, substituted heteroaryl, fused-heterocycle, and substituted fused-heterocycle, or together R$^3$ and R$^4$ comprise a C$_3$-C$_6$ carbocycle, substituted C$_3$-C$_6$ carbocycle or oxo.

In certain embodiments, $R^3$ and $R^4$ are independently selected from the group consisting of —F, —Cl, —CH$_3$, or together $R^3$ and $R^4$ comprise a cyclopropyl, cyclobutyl, cyclopentyl or oxo.

In certain embodiments, W is selected from —CH$_2$— and —CHR$^3$—.

In certain embodiments, W is —CH$_2$—.

In certain embodiments, Z is selected from the group consisting of —OR$^5$, —F, —NHC(=O)R$^5$, and heteroaryl.

In certain embodiments, Z is selected from the group consisting of —OR$^5$, and —NHC(=O)R$^5$.

In certain embodiments, each $R^5$ is independently selected from —H, —CH$_3$, —CH$_2$CH$_3$, —CH(CH$_3$)$_2$ and phenyl.

In certain embodiments, each $R^5$ is independently selected from —H, and —CH$_3$.

In certain embodiments, the compound is selected from the group consisting of:

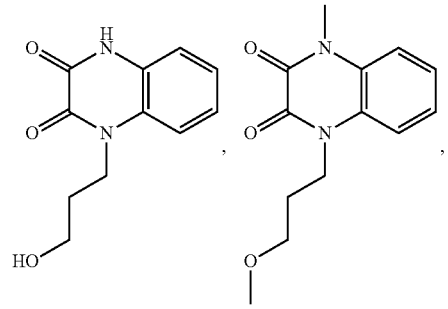

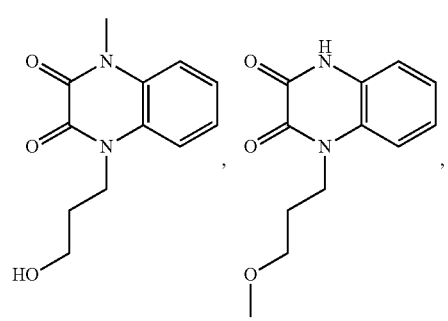

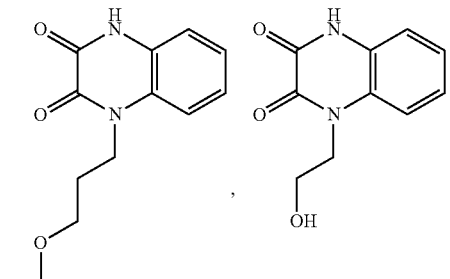

-continued

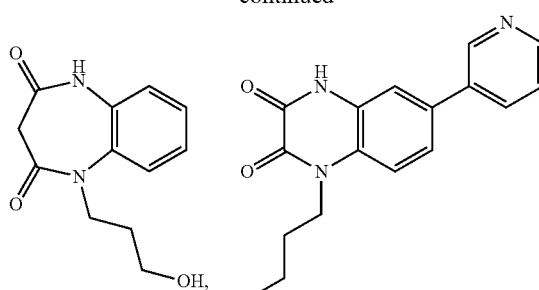

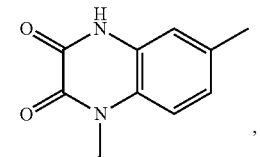

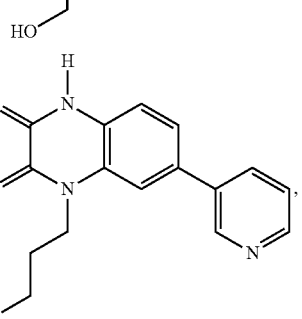

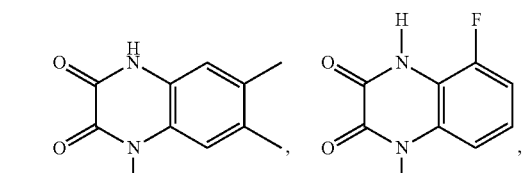

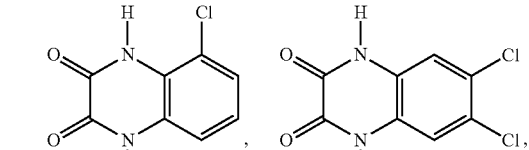

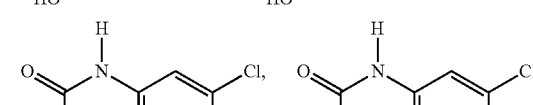

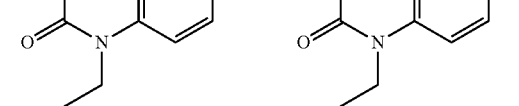

Aspects of the present disclosure include a compound of formula (IV):

$$\text{(IV)}$$

wherein:
R is selected from the group consisting of —H and $C_1$-$C_6$-alkyl;
each $R^1$ is independently selected from the group consisting of —H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;
each $R^2$ is independently selected from the group consisting of —H, and $C_1$-$C_6$-alkyl;
each W is independently selected from the group consisting of —$CH_2$—, —$CHR^3$— and —$CR^3R^4$—;
$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, or substituted carbocycle;
Z is selected from the group consisting of —OH, —OC(=O)$CH_3$, —OC(=O)Ph, and —NHC(=O)$CH_3$;
or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof;
with the proviso that the compound is not:
N-[3-(3,4-dihydro-3-oxo-1(2H)-quinoxalinyl)-3-oxopropyl]acetamide.

In certain embodiments, R is —$CH_2CH_3$ or —$CH_3$.
In certain embodiments, R is —H.
In certain embodiments, each $R^1$ is independently selected from the group consisting of —H, —F, —Cl, $C_1$-$C_6$-alkyl, substituted $C_1$-$C_6$-alkyl, —$OCH_3$, heteroaryl, and substituted heteroaryl.
In certain embodiments, each $R^1$ is independently selected from the group consisting of —H, —F, —Cl, —$CH_3$, —$CF_3$, —$OCH_3$, and pyridyl.
In certain embodiments, each $R^1$ is —H.
In certain embodiments, $R^3$ and $R^4$ are independently selected from the group consisting of —F, —Cl, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, or together $R^3$ and $R^4$ comprise a $C_3$-$C_6$-cycloalkyl, or substituted $C_3$-$C_6$-cycloalkyl.
In certain embodiments, $R^3$ and $R^4$ are independently selected from the group consisting of —F, —$CH_3$, —$CH_2CH_3$, or together $R^3$ and $R^4$ comprise cyclopropyl, substituted cyclopropyl, cyclobutyl, substituted cyclobutyl, cyclopentyl, or substituted cyclopentyl.
In certain embodiments, each W is selected from —$CHR^3$— and —$CR^3R^4$—.
In certain embodiments, each W is —$CH_2$—.
In certain embodiments, Z is selected from the group consisting of —OH, and —OC(=O)$CH_3$.
In certain embodiments, Z is —OH.
In certain embodiments, the compound is selected from:

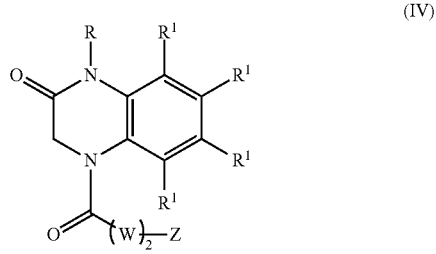

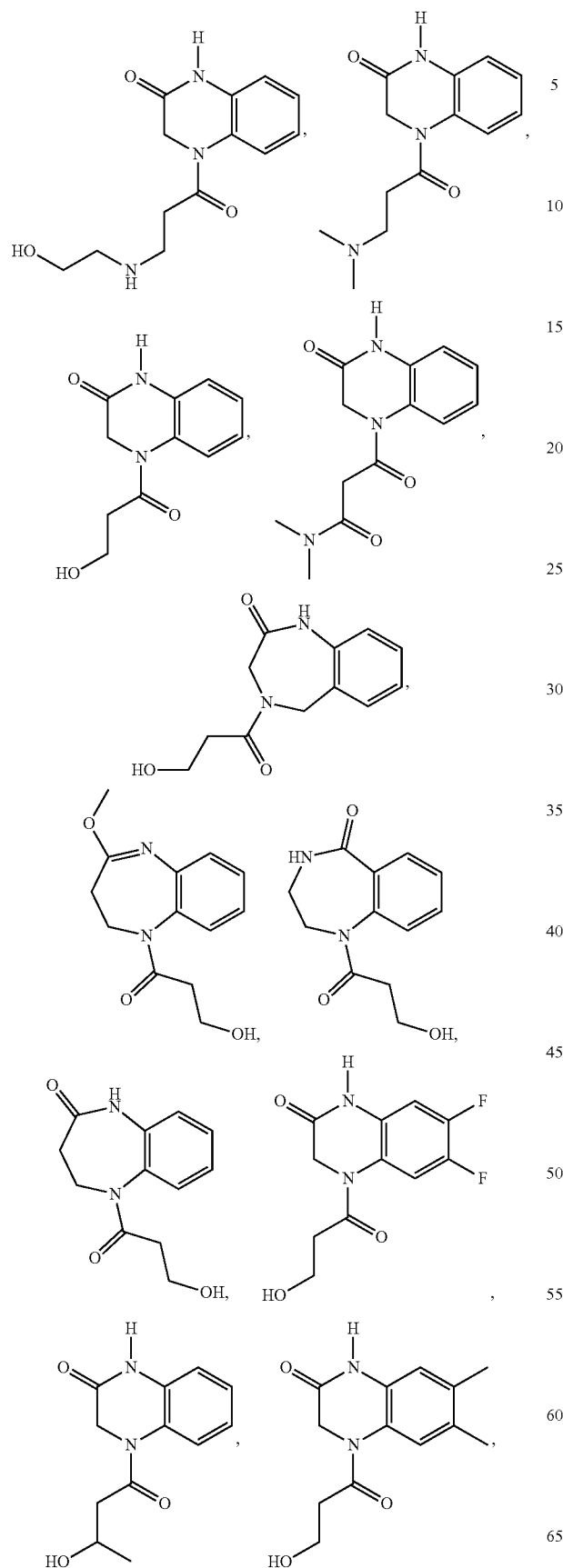
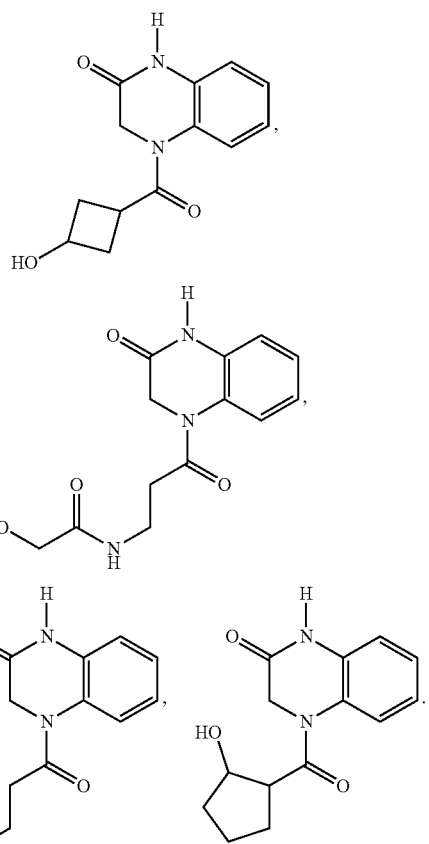
Aspects of the present disclosure include a compound of Formula (V), Formula (VI), or Formula (VII):
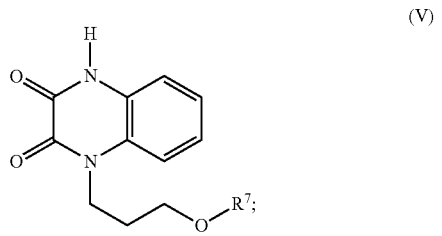
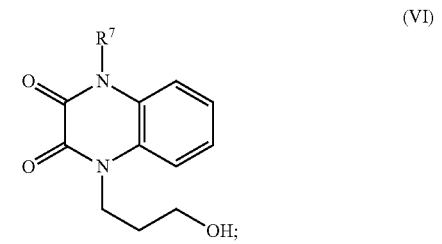

11
-continued

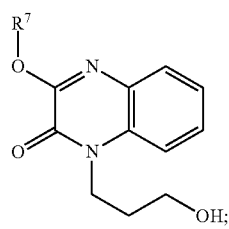
(VII)

wherein:
R⁷ is selected from the group consisting of —CH₂OC(=O)OR⁸, —C(CH₃)HOC(=O)OR⁸, —C(=O)R⁸, —C(=O)OR⁸, —C(=O)NHR⁸, —C(=O)NR⁸R⁸, and C₁-C₆-alkyl; and
each R⁸ is independently selected from C₁-C₆-alkyl, substituted C₂-C₆-alkyl, C₃-C₆-cycloalkyl, substituted C₃-C₆-cycloalkyl, heterocycyl, substituted heterocycyl, aryl, substituted aryl, heteroaryl, and substituted heteroaryl,
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

In certain embodiments, the compound is selected from:

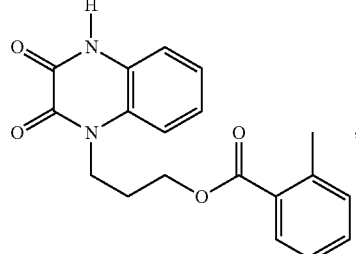

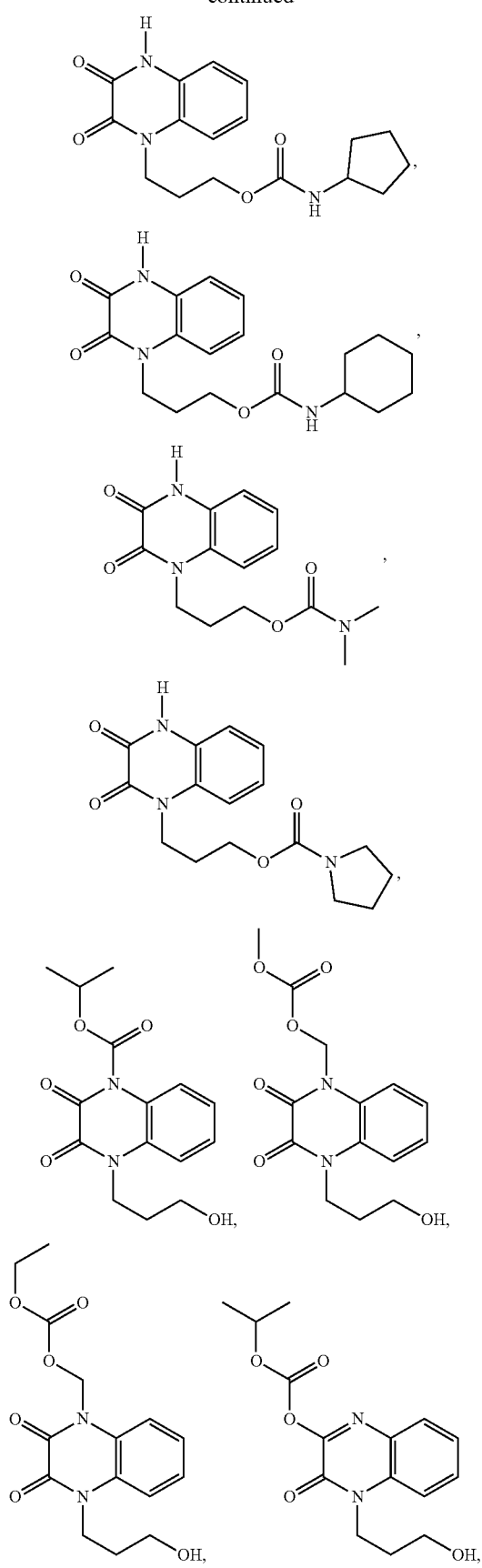

Aspects of the present disclosure include a method of inhibiting activity of an amylin receptor, where the method includes administering to a subject in need thereof, a therapeutically effective amount of a compound of formula (IV), formula (V), formula (VI), or formula (VII) of the present disclosure.

In certain embodiments, the amylin receptor is an AMY3 receptor.

In certain embodiments, the administering is effective for treating a disease mediated through activity of the amylin receptor. In certain embodiments, the disease is Alzheimer's disease.

DEFINITIONS

Figure 1:
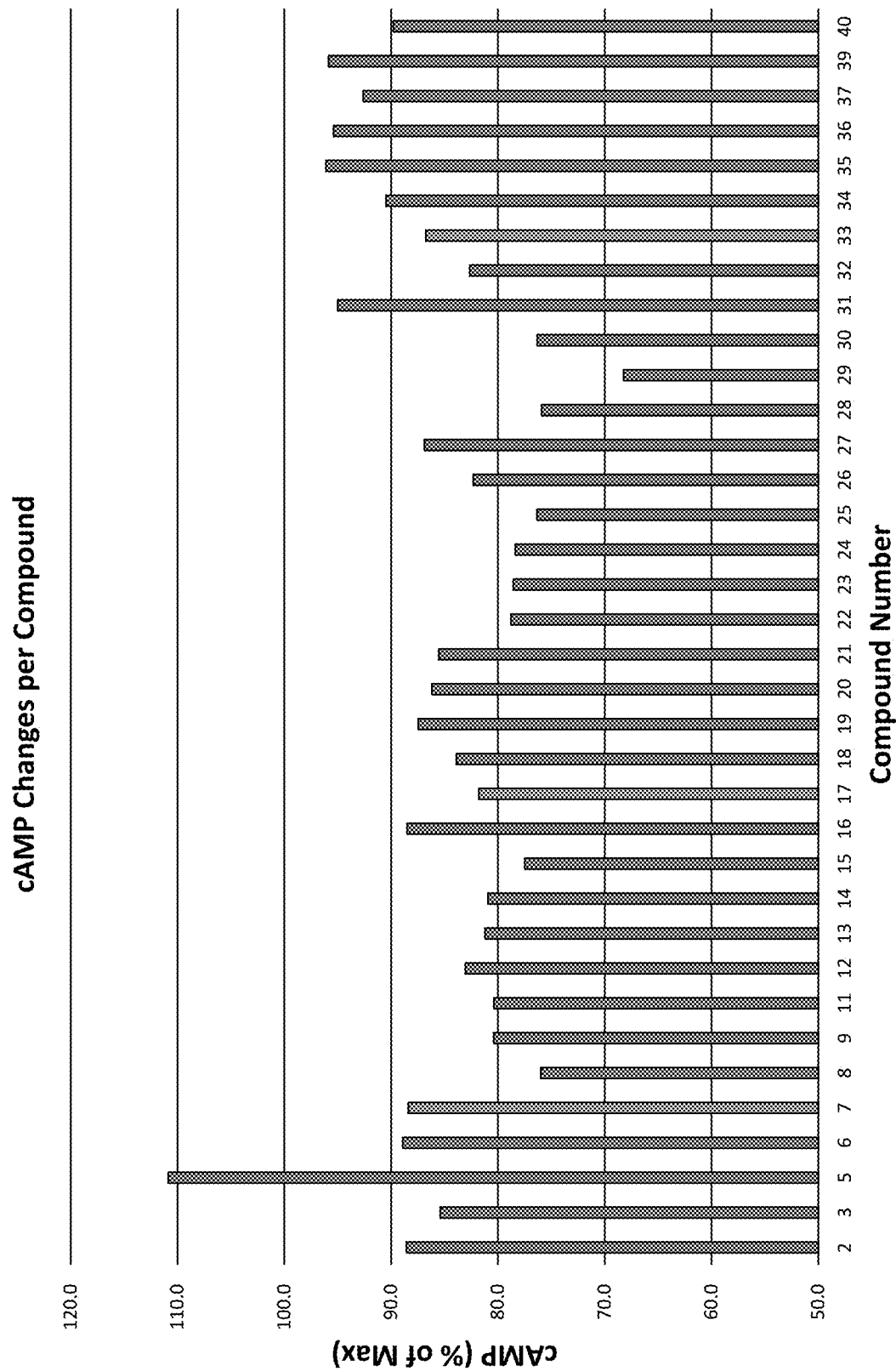
FIG. 1: Screening of compounds using ELISA assay for cAMP in AMY3 transfected cells. cAMP generation by 0.5 μM was normalized to 100% and the ability of individual compounds to attenuate this response in the presence of human amylin was assessed.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C (O)—, —C(O)NR$^{10}$— and the like, where R$^{10}$ is chosen from chosen from hydrogen, optionally substituted alkyl, cycloalkyl, alkenyl, cycloalkenyl, alkynyl, aryl, heteroaryl and heterocyclic. This term includes, by way of example, methylene (—CH$_2$—), ethylene (—CH$_2$CH$_2$—), n-propylene (—CH$_2$CH$_2$CH$_2$—), iso-propylene (—CH$_2$CH (CH$_3$)—), (—C(CH$_3$)$_2$CH$_2$CH$_2$—), (—C(CH$_3$)$_2$CH$_2$C (O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO— substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, —NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O) NR$^{22}$R$^{23}$ where R$^{21}$, R$^{22}$, and R$^{23}$ are independently selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NR$^d$C(O)OR$^d$ where each R$^d$ is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O) O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfonylamino" refers to the group —NR$^{21}$SO$_2$R$^{22}$, wherein R$^{21}$ and R$^{22}$ independently are selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NR'''R''' where each R''' is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Carbocycle" refers to non-aromatic or aromatic cyclic groups, such as cycloalkyl, cycloalkenyl, cycloalkynyl, and aryl groups as defined herein. A carbocycle goup may be unsubstituted or substituted as defined herein.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein.

This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, heterocyclyl, aryl, or heteroaryl, provided that the point of attachment is through the non-aromatic ring. Fused ring systems include compounds where two rings share two adjacent atoms. In fused heterocycle systems one or both of the two fused rings can be heterocyclyl. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, 1,2,3,4-tetrahydroquinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, 3,4-dihydro-1,4-benzoxazine, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (═O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (═S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with ═O, ═NR$^{70}$, ═N—OR$^{70}$, ═N$_2$ or ═S) on saturated carbon atoms in the specified group or radical are, unless otherwise specified, —R$^{60}$, halo, ═O, —OR$^{70}$, —SR$^{70}$, —NR$^{80}$R$^{80}$, trihalomethyl, —CN, —OCN, —SCN, —NO, —NO$_2$, ═N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkyl-alkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

By "treating" or "treatment" is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the subject no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state or prophylactic treatment of a subject; (ii) inhibition, that is, arresting the development or further development of clinical symptoms, e.g., mitigating or completely inhibiting an active disease; and/or (iii) relief, that is, causing the regression of clinical symptoms or alleviating one or more symptoms of the disease or medical condition in the subject.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

As used herein, the term "amylin" refers to a 37 amino acid peptide hormone which is co-secreted with insulin from the pancreatic j-cell.

As used herein, the term "amyloid-beta protein" refers to peptides of 36-43 amino acids resulting from cleavage of the amyloid precursor protein, and which form the main component of neurotoxic amyloid plaques found in the brains of Alzheimer patients.

As used herein, the term "amylin receptor" refers to a receptor complex which binds amylin and amyloid-beta protein. The amylin receptor includes the calcitonin receptor (CTR) dimerized with one of three known subtypes of receptor activity-modifying protein (RAMP1, RAMP2, RAMP3). Both amylin (HA) and amyloid-beta protein (Aβ42) bind and directly activate the amylin receptor and trigger biological and neurotoxic effects. (Jhamandas et al., 2004).

As used herein, the term "amylin receptor antagonist" refers to a compound useful as an antagonist of the amylin receptor, or which binds to, but does not activate, the amylin receptor. The amylin receptor antagonist displaces and blocks the binding of amylin or amyloid-beta protein to the amylin receptor, thereby inhibiting the activity of amylin or amyloid-beta protein.

As used herein, the term "AC253" refers to a peptide antagonist of the amylin receptor. The "AC" prefix indicates the peptide's identity within the peptide library of Amylin Pharmaceuticals Inc. As used herein, the term "AC253" refers to a peptide having the amino acid sequence of SEQ ID NO: 1 (Ac-LGRLSQELHRLQTYPRTNTGSNTY) and which is capable of binding to the amylin receptor, thereby inhibiting the activity of amylin, amyloid-beta protein, or both.

As used herein, the term "chronic administration" refers to repeated administration of a compound to a subject. In such treatment, the compound can be administered at least once a week, such as at least once a day, or at least twice or three times a day for a period of at least one month, such as for example five months or more.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compounds that are amylin receptor antagonists, compositions that include the subject compounds, and methods for preparing and using the amylin receptor antagonists and the compositions for treating, preventing, or ameliorating Alzheimer's disease.

Compounds and Methods of Treatment

The present disclosure provides methods of inhibiting activity of an amylin receptor. Embodiments of the present disclosure thus relate to methods and uses of the compounds disclosed herein as amylin receptor antagonists which bind to, but do not activate, the amylin receptor. Compounds of the present disclosure may be used to displace and/or block the binding of amylin or amyloid-beta protein to the amylin receptor, thereby inhibiting the activity of amylin or amyloid-beta protein. In some instances, compounds of the present disclosure are capable of binding to the AMY1 receptor. In some instances, compounds of the present disclosure are capable of binding to the AMY2 receptor. In some instances, compounds of the present disclosure are capable of binding to the AMY3 receptor. In some instances, compounds of the present disclosure are capable of binding to the AMY1 and AMY2 receptors. In some instances, compounds of the present disclosure are capable of binding to the AMY1 and AMY3 receptors. In some instances, compounds of the present disclosure are capable of binding to the AMY2 and AMY3 receptors. In some instances, compounds of the present disclosure are capable of binding to the AMY1, AMY2 and AMY3 receptors. As used herein, "AMY1 receptor" refers to a heterodimeric complex of the calcitonin receptor and RAMP1. As used herein, "AMY2 receptor" refers to a heterodimeric complex of the calcitonin receptor and RAMP2. As used herein, "AMY3 receptor" refers to a heterodimeric complex of the calcitonin receptor and RAMP3.

The amylin receptor antagonist may be used to reduce incidence of, reduce, treat, diminish, or prevent a disease or disorder in a subject where it is of benefit to reduce amylin or amyloid-beta protein activity. In certain embodiments, the disease is Alzheimer's disease. Therapeutic uses of compounds of the present disclosure in diseases or disorders, methods of prevention or treatment using compounds of the present disclosure, and uses of compounds of the present disclosure to prepare medicaments for therapeutic use are also included in embodiments of the present disclosure. In certain instances, embodiments of the present disclosure relate to the therapeutic use of compounds of the present disclosure in humans.

In certain embodiments, a method of treating, preventing, or ameliorating a disease or disorder in a subject is provided, where the method includes administering to the subject a therapeutically effective amount of one or more compounds of the present disclosure or a composition including same. As used herein, the term "disease" includes, but is not limited to, Alzheimer's disease. An effective amount of the compound or composition may be an amount sufficient to provide either subjective relief of symptoms or an objectively identifiable improvement as noted by a clinician or other qualified observer. As such, methods of "treating", "preventing" or "ameliorating" refer to interventions performed with the intention of alleviating the symptoms associated with, preventing the development of, or altering the pathology of a disease, disorder or condition, such as Alzheimer's disease. Thus, in various embodiments, the methods of the present disclosure may include the prevention (prophylaxis), moderation, reduction, or curing of a disease, disorder or condition at various stages, such as for example Alzheimer's disease. In various embodiments, therefore, those in need of therapy/treatment may include those already having the disease, disorder or condition and/or those prone to, or at risk of developing, the disease, disorder or condition and/or those in whom the disease, disorder or condition is to be prevented.

In certain embodiments, the amylin receptor antagonist of the present disclosure is effective for reducing cyclic AMP (cAMP) signal production in a cell. For example, administration of a therapeutically effective amount of the amylin receptor antagonist may cause a reduction in cAMP signal production in a cell as compared to a cell that has not been administered the amylin receptor antagonist.

In certain embodiments, compounds of the present disclosure produce a neuroprotective effect against amylin and/or amyloid-beta protein induced neurotoxicity. For example, in some cases, administration of a compound of the present disclosure is therapeutically effective for protecting neurons against the neurotoxic effect of amyloid-beta protein. In some cases, administration of a compound of the present disclosure is therapeutically effective for protecting neurons against the neurotoxic effect of amylin.

Methods of the present disclosure include administering to a subject in need thereof, a therapeutically effective amount of an amylin receptor antagonist. In certain embodiments, the amylin receptor antagonist is a non-peptidic compound. Non-peptidic compounds according to the present disclosure do not contain as part of their chemical structure a peptide or peptide derivative (e.g., modified peptide).

Formula (I)

In certain embodiments, the amylin receptor antagonist is a compound of formula (I):

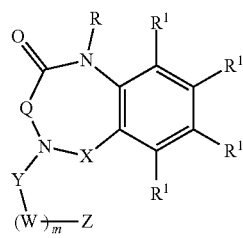

(I)

wherein:
R is selected from the group consisting of —H, $C_1$-$C_6$-alkyl, and substituted $C_1$-$C_6$-alkyl;
each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;

each $R^2$ is independently selected from the group consisting of —H, $C_1$-$C_6$-alkyl, and substituted $C_1$-$C_6$-alkyl;
each W is selected from the group consisting of —$CH_2$—, —$CHR^3$— and —$CR^3R^4$—;
$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo (i.e., =O);
m is selected from 1, 2 or 3;
Q is selected from the group consisting of —$CH_2$—, —C(=O)—, —$CH_2$C(=O)—, and —$CH_2CH_2$—;
X is present or absent, and if present is selected from the group consisting of —$CH_2$— and —C(=O)—;
Y is selected from the group consisting of —$CH_2$—, and —C(=O)—;
Z is selected from the group consisting of —$OR^5$, halogen, —CN, —$NR^5R^5$, —NHC(=O)$R^5$, —NHC(=O)$NR^5R^5$, aryl, and heteroaryl; and
each $R^5$ is independently selected from the group consisting of —H, $C_1$-$C_6$-alkyl, substituted $C_1$-$C_6$-alkyl, aryl, substituted aryl, heteroaryl, and substituted heteroaryl;
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

In certain embodiments, R is selected from —H, $C_1$-$C_6$-alkyl, and substituted $C_1$-$C_6$-alkyl. For example, in some embodiments, R can be —H. In some embodiments, R can be $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl).

In certain embodiments, each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl. For example, $R^1$ can be H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, or substituted heteroaryl. In some instances, $R^1$ is H. In some instances, $R^1$ is halogen (e.g., F, Cl, Br, I). In some instances, $R^1$ is $C_1$-$C_6$-alkyl (e.g., methyl, ethyl, propyl, butyl, pentyl, or hexyl) or substituted $C_1$-$C_6$-alkyl (e.g., substituted methyl (e.g., —$CF_3$), substituted ethyl, substituted propyl, substituted butyl, substituted pentyl, or substituted hexyl). In some instances, $R^1$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^1$ is —$OR^2$. In some instances, $R^1$ is heterocyclyl or substituted heterocyclyl (e.g., unsubstituted or substituted pyrrolidinyl, imidazolidinyl, piperidinyl, piperazinyl, morpholinyl, and the like). In some instances, $R^1$ is aryl or substituted aryl (e.g., unsubstituted or substituted phenyl). In some instances, $R^1$ is heteroaryl or substituted heteroaryl (e.g., unsubstituted or substituted pyrrolyl, pyrazolyl, imidazolyl, pyridyl, pyrimidinyl, and the like).

In certain embodiments, each $R^2$ is independently selected from the group consisting of —H, $C_1$-$C_6$-alkyl, and substituted $C_1$-$C_6$-alkyl. For example, in some embodiments, $R^2$ can be —H. In some embodiments, $R^2$ can be $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl).

In certain embodiments, each W is selected from the group consisting of —$CH_2$—, —$CHR^3$— and —$CR^3R^4$—. In some instances, W is —$CH_2$—. In some instances, W is —$CHR^3$—. In some instances, W is —$CR^3R^4$—.

In certain embodiments, $R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo.

For example, $R^3$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^3$ is halogen (e.g., F, Cl, Br, I). In some instances, $R^3$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^3$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^3$ is heterocyclyl or substituted heterocyclyl. In some instances, $R^3$ is aryl or substituted aryl (e.g., unsubstituted or substituted phenyl). In some instances, $R^3$ is heteroaryl or substituted heteroaryl. In some instances, $R^3$ is fused-heterocycle or substituted fused-heterocycle.

For example, $R^4$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^4$ is halogen (e.g., F, Cl, Br, I). In some instances, $R^4$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^4$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^4$ is heterocyclyl or substituted heterocyclyl. In some instances, $R^4$ is aryl or substituted aryl (e.g., unsubstituted or substituted phenyl). In some instances, $R^4$ is heteroaryl or substituted heteroaryl. In some instances, $R^4$ is fused-heterocycle or substituted fused-heterocycle.

In certain embodiments, together $R^3$ and $R^4$ comprise a carbocycle, substituted carbocycle or oxo (i.e., =O). In some instances, together $R^3$ and $R^4$ comprise a carbocycle, such as a $C_3$-$C_6$ carbocycle (e.g., cyclopropyl, cyclobutyl, cyclopentyl). In some instances, together $R^3$ and $R^4$ comprise a substituted carbocycle, such as a substituted $C_3$-$C_6$ carbocycle (e.g., substituted cyclopropyl, substituted cyclobutyl, substituted cyclopentyl). In some instances, together $R^3$ and $R^4$ comprise an oxo group (i.e., =O).

In some embodiments, m is selected from 1, 2 or 3. In some instances, m is 1. In some instances, m is 2. In some instances, m is 3.

In certain embodiments, Q is selected from —$CH_2$—, —C(=O)—, —$CH_2$C(=O)—, and —$CH_2CH_2$—. In some instances, Q is —$CH_2$—. In some instances, Q is —C(=O)—. In some instances, Q is —$CH_2$C(=O)—. In some instances, Q is —$CH_2CH_2$—.

In certain embodiments, X is present or absent, and if present is selected from the group consisting of —$CH_2$— and —C(=O)—. In some instances, X is absent. In embodiments were X is absent, the N adjacent to X is directly bonded to the phenyl ring in formula (I). In some instances, X is present. In some instances, X is —$CH_2$—. In some instances, X is —C(=O)—.

In certain embodiments, Y is selected from —$CH_2$—, and —C(=O)—. In some instances, Y is —$CH_2$—. In some instances, Y is —C(=O)—.

In certain embodiments, Z is selected from the group consisting of —$OR^5$, halogen, —CN, —$NR^5R^5$, —NHC(=O)$R^5$, —NHC(=O)$NR^5R^5$, aryl, and heteroaryl. In some instances, Z is —$OR^5$. In some instances, Z is halogen (e.g., F, Cl, Br, I). In some instances, Z is —CN. In some instances, Z is —$NR^5R^5$. In some instances, Z is —NHC(=O)$R^5$. In some instances, Z is —NHC(=O)$NR^5R^5$. In some instances, Z is aryl (e.g., phenyl). In some instances, Z is heteroaryl.

In certain embodiments, each $R^5$ is independently selected from the group consisting of —H, $C_1$-$C_6$-alkyl, substituted $C_1$-$C_6$-alkyl, aryl, substituted aryl, heteroaryl, and substituted heteroaryl. For example, $R^5$ can be H, $C_1$-$C_6$-alkyl, substituted $C_1$-$C_6$-alkyl, aryl, substituted aryl, heteroaryl, or substituted heteroaryl. In some instances, $R^5$ is H. In some instances, $R^5$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl (e.g., isopropyl), substituted propyl, substituted butyl, substituted pentyl, or substituted hexyl). In some instances, $R^5$ is aryl or substituted aryl (e.g., unsubstituted or substituted phenyl). In some instances, $R^5$ is heteroaryl or substituted heteroaryl (e.g., unsubstituted or substituted pyrrolyl, pyrazolyl, imidazolyl, pyridinyl, pyrimidinyl, and the like).

Formula (II)

In certain embodiments, the amylin receptor antagonist is a compound of formula (II):

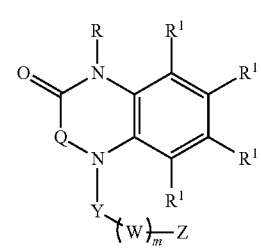

(II)

wherein:
R is selected from the group consisting of —H and $C_1$-$C_6$-alkyl;
each $R^1$ is independently selected from the group consisting of —H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;
each $R^2$ is independently selected from the group consisting of —H, and $C_1$-$C_6$-alkyl;
each W is selected from the group consisting of —$CH_2$—, —$CHR^3$— and —$CR^3R^4$—;

$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo;

m is selected from 1, 2 or 3;

Q is selected from the group consisting of —$CH_2$—, —C(=O)— and —$CH_2$C(=O)—;

Y is selected from the group consisting of —$CH_2$—, and —C(=O)—;

Z is selected from the group consisting of —$OR^5$, -halogen, —$NR^5R^5$, —NHC(=O)$R^5$, —NHC(=O)$NR^5R^5$, aryl, and heteroaryl; and each $R^5$ is independently selected from the group consisting of —H, $C_1$-$C_6$-alkyl, substituted $C_1$-$C_6$-alkyl, aryl, substituted aryl, heteroaryl, and substituted heteroaryl;

or an enantiomer, a mixture of enantiomers, a mixture of two or more diastereomers, a tautomer, a mixture of two or more tautomers, or an isotopic variant thereof;

or a pharmaceutically acceptable salt, solvate, or hydrate thereof.

In certain embodiments, R is selected from —H and $C_1$-$C_6$-alkyl. For example, in some embodiments, R can be —H. In some embodiments, R can be $C_1$-$C_6$-alkyl (e.g., methyl, ethyl, propyl, butyl, pentyl, or hexyl).

In certain embodiments, each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl. For example, $R^1$ can be H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, or substituted heteroaryl. In some instances, $R^1$ is H. In some instances, $R^1$ is halogen (e.g., F, Cl, Br, I). In some instances, $R^1$ is $C_1$-$C_6$-alkyl (e.g., methyl, ethyl, propyl, butyl, pentyl, or hexyl) or substituted $C_1$-$C_6$-alkyl (e.g., substituted methyl (e.g., —$CF_3$), substituted ethyl, substituted propyl, substituted butyl, substituted pentyl, or substituted hexyl). In some instances, $R^1$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^1$ is —$OR^2$. In some instances, $R^1$ is heterocyclyl or substituted heterocyclyl (e.g., unsubstituted or substituted pyrrolidinyl, imidazolidinyl, piperidinyl, piperazinyl, morpholinyl, and the like). In some instances, $R^1$ is aryl or substituted aryl (e.g., unsubstituted or substituted phenyl). In some instances, $R^1$ is heteroaryl or substituted heteroaryl (e.g., unsubstituted or substituted pyrrolyl, pyrazolyl, imidazolyl, pyridyl, pyrimidinyl, and the like).

In certain embodiments, each $R^2$ is independently selected from the group consisting of —H and $C_1$-$C_6$-alkyl. For example, in some embodiments, $R^2$ can be —H. In some embodiments, $R^2$ can be $C_1$-$C_6$-alkyl (e.g., methyl, ethyl, propyl, butyl, pentyl, or hexyl).

In certain embodiments, each W is selected from the group consisting of —$CH_2$—, —$CHR^3$— and —$CR^3R^4$—. In some instances, W is —$CH_2$—. In some instances, W is —$CHR^3$—. In some instances, W is —$CR^3R^4$—.

In certain embodiments, $R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo.

For example, $R^3$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^3$ is halogen (e.g., F, Cl, Br, I). In some instances, $R^3$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^3$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^3$ is heterocyclyl or substituted heterocyclyl. In some instances, $R^3$ is aryl or substituted aryl (e.g., unsubstituted or substituted phenyl). In some instances, $R^3$ is heteroaryl or substituted heteroaryl. In some instances, $R^3$ is fused-heterocycle or substituted fused-heterocycle.

For example, $R^4$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^4$ is halogen (e.g., F, Cl, Br, I). In some instances, $R^4$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^4$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^4$ is heterocyclyl or substituted heterocyclyl. In some instances, $R^4$ is aryl or substituted aryl (e.g., unsubstituted or substituted phenyl). In some instances, $R^4$ is heteroaryl or substituted heteroaryl. In some instances, $R^4$ is fused-heterocycle or substituted fused-heterocycle.

In certain embodiments, together $R^3$ and $R^4$ comprise a carbocycle, substituted carbocycle or oxo (i.e., =O). In some instances, together $R^3$ and $R^4$ comprise a carbocycle, such as a $C_3$-$C_6$ carbocycle (e.g., cyclopropyl, cyclobutyl, cyclopentyl). In some instances, together $R^3$ and $R^4$ comprise a substituted carbocycle, such as a substituted $C_3$-$C_6$ carbocycle (e.g., substituted cyclopropyl, substituted cyclobutyl, substituted cyclopentyl). In some instances, together $R^3$ and $R^4$ comprise an oxo group (i.e., =O).

In certain embodiments, m is selected from 1, 2 or 3. In some instances, m is 1. In some instances, m is 2. In some instances, m is 3.

In certain embodiments, Q is selected from —$CH_2$—, —C(=O)—, and —$CH_2$C(=O)—. In some instances, Q is —$CH_2$—. In some instances, Q is —C(=O)—. In some instances, Q is —$CH_2$C(=O)—.

In certain embodiments, Y is selected from —$CH_2$—, and —C(=O)—. In some instances, Y is —$CH_2$—. In some instances, Y is —C(=O)—.

In certain embodiments, Z is selected from the group consisting of —$OR^5$, halogen, —$NR^5R^5$, —NHC(=O)$R^5$, —NHC(=O)$NR^5R^5$, aryl, and heteroaryl. In some instances, Z is —$OR^5$. In some instances, Z is halogen (e.g., F, Cl, Br, I). In some instances, Z is —$NR^5R^5$. In some instances, Z is —NHC(═O)R$^5$. In some instances, Z is —NHC(═O)NR$^5$R$^5$. In some instances, Z is aryl (e.g., phenyl). In some instances, Z is heteroaryl.

In certain embodiments, each R$^5$ is independently selected from the group consisting of —H, C$_1$-C$_6$-alkyl, substituted C$_1$-C$_6$-alkyl, aryl, substituted aryl, heteroaryl, and substituted heteroaryl. For example, R$^5$ can be H, C$_1$-C$_6$-alkyl, substituted C$_1$-C$_6$-alkyl, aryl, substituted aryl, heteroaryl, or substituted heteroaryl. In some instances, R$^5$ is H. In some instances, R$^5$ is C$_1$-C$_6$-alkyl (e.g., methyl, ethyl, propyl, butyl, pentyl, or hexyl) or substituted C$_1$-C$_6$-alkyl (e.g., substituted methyl, substituted ethyl (e.g., isopropyl), substituted propyl, substituted butyl, substituted pentyl, or substituted hexyl). In some instances, R$^5$ is aryl or substituted aryl (e.g., unsubstituted or substituted phenyl). In some instances, R$^5$ is heteroaryl or substituted heteroaryl (e.g., unsubstituted or substituted pyrrolyl, pyrazolyl, imidazolyl, pyridinyl, pyrimidinyl, and the like).

Formula (III)

In certain embodiments, the amylin receptor antagonist is a compound of formula (III):

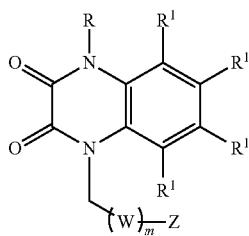

(III)

wherein:
R is selected from the group consisting of —H and C$_1$-C$_6$-alkyl;
each R$^1$ is independently selected from the group consisting of —H, halogen, C$_1$-C$_6$-alkyl, substituted C$_1$-C$_6$-alkyl, C$_3$-C$_6$-cycloalkyl, substituted C$_3$-C$_6$-cycloalkyl, —OR$^2$, heterocyclyl, substituted heterocyclyl, aryl, substituted aryl, heteroaryl, and substituted heteroaryl;
each R$^2$ is independently selected from the group consisting of —H, and C$_1$-C$_6$-alkyl;
each W is selected from the group consisting of —CH$_2$—, —CHR$^3$— and —CR$^3$R$^4$—;
R$^3$ and R$^4$ are independently selected from the group consisting of halogen, C$_1$-C$_6$-alkyl, substituted C$_1$-C$_6$-alkyl, C$_3$-C$_6$-cycloalkyl, substituted C$_3$-C$_6$-cycloalkyl, heterocyclyl, substituted heterocyclyl, aryl, substituted aryl, heteroaryl, substituted heteroaryl, fused-heterocycle, and substituted fused-heterocycle, or together R$^3$ and R$^4$ comprise a carbocycle, substituted carbocycle or oxo;
m is selected from 1, 2 or 3;
Z is selected from the group consisting of —OR$^5$, halogen, —NR$^5$R$^5$, —NHC(═O)R$^5$, —NHC(═O)NR$^5$R$^5$, aryl, and heteroaryl; and
each R$^5$ is independently selected from the group consisting of —H, C$_1$-C$_6$-alkyl, substituted C$_1$-C$_6$-alkyl, aryl, substituted aryl, heteroaryl, and substituted heteroaryl;
or an enantiomer, a mixture of enantiomers, a mixture of two or more diastereomers, a tautomer, a mixture of two or more tautomers, or an isotopic variant thereof; or a pharmaceutically acceptable salt, solvate, or hydrate thereof.

In certain embodiments, R is selected from —H and C$_1$-C$_6$-alkyl. For example, in some embodiments, R can be —H. In some embodiments, R can be C$_1$-C$_6$-alkyl (e.g., methyl, ethyl, propyl, butyl, pentyl, or hexyl).

In certain embodiments, each R$^1$ is independently selected from the group consisting of H, halogen, C$_1$-C$_6$-alkyl, substituted C$_1$-C$_6$-alkyl, C$_3$-C$_6$-cycloalkyl, substituted C$_3$-C$_6$-cycloalkyl, —OR$^2$, heterocyclyl, substituted heterocyclyl, aryl, substituted aryl, heteroaryl, and substituted heteroaryl. For example, R$^1$ can be H, halogen, C$_1$-C$_6$-alkyl, substituted C$_1$-C$_6$-alkyl, C$_3$-C$_6$-cycloalkyl, substituted C$_3$-C$_6$-cycloalkyl, —OR$^2$, heterocyclyl, substituted heterocyclyl, aryl, substituted aryl, heteroaryl, or substituted heteroaryl. In some instances, R$^1$ is H. In some instances, R$^1$ is halogen (e.g., F, Cl, Br, I). In some instances, R$^1$ is C$_1$-C$_6$-alkyl (e.g., methyl, ethyl, propyl, butyl, pentyl, or hexyl) or substituted C$_1$-C$_6$-alkyl (e.g., substituted methyl (e.g., —CF$_3$), substituted ethyl, substituted propyl, substituted butyl, substituted pentyl, or substituted hexyl). In some instances, R$^1$ is C$_3$-C$_6$-cycloalkyl (e.g., cyclopropyl, cyclobutyl, cyclopentyl, or cyclohexyl) or substituted C$_3$-C$_6$-cycloalkyl (e.g., substituted cyclopropyl, substituted cyclobutyl, substituted cyclopentyl, or substituted cyclohexyl). In some instances, R$^1$ is —OR$^2$. In some instances, R$^1$ is heterocyclyl or substituted heterocyclyl (e.g., unsubstituted or substituted pyrrolidinyl, imidazolidinyl, piperidinyl, piperazinyl, morpholinyl, and the like). In some instances, R$^1$ is aryl or substituted aryl (e.g., unsubstituted or substituted phenyl). In some instances, R$^1$ is heteroaryl or substituted heteroaryl (e.g., unsubstituted or substituted pyrrolyl, pyrazolyl, imidazolyl, pyridyl, pyrimidinyl, and the like).

In certain embodiments, each R$^2$ is independently selected from the group consisting of —H and C$_1$-C$_6$-alkyl. For example, in some embodiments, R$^2$ can be —H. In some embodiments, R$^2$ can be C$_1$-C$_6$-alkyl (e.g., methyl, ethyl, propyl, butyl, pentyl, or hexyl).

In certain embodiments, each W is selected from the group consisting of —CH$_2$—, —CHR$^3$— and —CR$^3$R$^4$—. In some instances, W is —CH$_2$—. In some instances, W is —CHR$^3$—. In some instances, W is —CR$^3$R$^4$—.

In certain embodiments, R$^3$ and R$^4$ are independently selected from the group consisting of halogen, C$_1$-C$_6$-alkyl, substituted C$_1$-C$_6$-alkyl, C$_3$-C$_6$-cycloalkyl, substituted C$_3$-C$_6$-cycloalkyl, heterocyclyl, substituted heterocyclyl, aryl, substituted aryl, heteroaryl, substituted heteroaryl, fused-heterocycle, and substituted fused-heterocycle, or together R$^3$ and R$^4$ comprise a carbocycle, substituted carbocycle or oxo.

For example, R$^3$ can be halogen, C$_1$-C$_6$-alkyl, substituted C$_1$-C$_6$-alkyl, C$_3$-C$_6$-cycloalkyl, substituted C$_3$-C$_6$-cycloalkyl, heterocyclyl, substituted heterocyclyl, aryl, substituted aryl, heteroaryl, substituted heteroaryl, fused-heterocycle, or substituted fused-heterocycle. In some instances, R$^3$ is halogen (e.g., F, Cl, Br, I). In some instances, R$^3$ is C$_1$-C$_6$-alkyl (e.g., methyl, ethyl, propyl, butyl, pentyl, or hexyl) or substituted C$_1$-C$_6$-alkyl (e.g., substituted methyl, substituted ethyl, substituted propyl, substituted butyl, substituted pentyl, or substituted hexyl). In some instances, R$^3$ is C$_3$-C$_6$-cycloalkyl (e.g., cyclopropyl, cyclobutyl, cyclopentyl, or cyclohexyl) or substituted C$_3$-C$_6$-cycloalkyl (e.g., substituted cyclopropyl, substituted cyclobutyl, substituted cyclopentyl, or substituted cyclohexyl). In some instances, R$^3$ is heterocyclyl or substituted heterocyclyl. In some instances, R$^3$ is aryl or substituted aryl (e.g., unsubstituted or substituted phenyl). In some instances, R$^3$ is heteroaryl or substituted heteroaryl. In some instances, R$^3$ is fused-heterocycle or substituted fused-heterocycle.

For example, $R^4$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^4$ is halogen (e.g., F, Cl, Br, I). In some instances, $R^4$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^4$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^4$ is heterocyclyl or substituted heterocyclyl. In some instances, $R^4$ is aryl or substituted aryl (e.g., unsubstituted or substituted phenyl). In some instances, $R^4$ is heteroaryl or substituted heteroaryl. In some instances, $R^4$ is fused-heterocycle or substituted fused-heterocycle.

In certain embodiments, together $R^3$ and $R^4$ comprise a carbocycle, substituted carbocycle or oxo (i.e., =O). In some instances, together $R^3$ and $R^4$ comprise a carbocycle, such as a $C_3$-$C_6$ carbocycle (e.g., cyclopropyl, cyclobutyl, cyclopentyl). In some instances, together $R^3$ and $R^4$ comprise a substituted carbocycle, such as a substituted $C_3$-$C_6$ carbocycle (e.g., substituted cyclopropyl, substituted cyclobutyl, substituted cyclopentyl). In some instances, together $R^3$ and $R^4$ comprise an oxo group (i.e., =O).

In certain embodiments, m is selected from 1, 2 or 3. In some instances, m is 1. In some instances, m is 2. In some instances, m is 3.

In certain embodiments, Z is selected from the group consisting of —$OR^5$, halogen, —$NR^5R^5$, —NHC(=O)$R^5$, —NHC(=O)$NR^5R^5$, aryl, and heteroaryl. In some instances, Z is —$OR^5$. In some instances, Z is halogen (e.g., F, Cl, Br, I). In some instances, Z is —$NR^5R^5$. In some instances, Z is —NHC(=O)$R^5$. In some instances, Z is —NHC(=O)$NR^5R^5$. In some instances, Z is aryl (e.g., phenyl). In some instances, Z is heteroaryl.

In certain embodiments, each $R^5$ is independently selected from the group consisting of —H, $C_1$-$C_6$-alkyl, substituted $C_1$-$C_6$-alkyl, aryl, and heteroaryl. For example, $R^5$ can be H, $C_1$-$C_6$-alkyl, substituted $C_1$-$C_6$-alkyl, aryl, substituted aryl, heteroaryl, or substituted heteroaryl. In some instances, $R^5$ is H. In some instances, $R^5$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl (e.g., isopropyl), substituted propyl, substituted butyl, substituted pentyl, or substituted hexyl). In some instances, $R^5$ is aryl (e.g., phenyl). In some instances, $R^5$ is heteroaryl (e.g., pyrrolyl, pyrazolyl, imidazolyl, pyridinyl, pyrimidinyl, and the like).

Compounds of the present disclosure (e.g., compounds of formulae (I), (II) and (III) as described herein) also include an enantiomer, a mixture of enantiomers, a mixture of two or more diastereomers, a tautomer, a mixture of two or more tautomers, or an isotopic variant thereof.

In addition, compounds of the present disclosure (e.g., compounds of formulae (I), (II) and (III) as described herein) also include a pharmaceutically acceptable salt, solvate, or hydrate thereof.

In certain embodiments, compounds of the present disclosure (e.g., compounds that find use in the methods of the present disclosure) include compounds selected from:

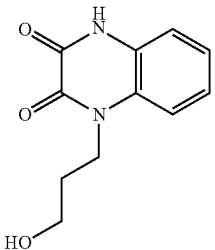

Compound 1

1-(3-hydroxypropyl)quinoxaline-2,3(1H,4H)-dione;

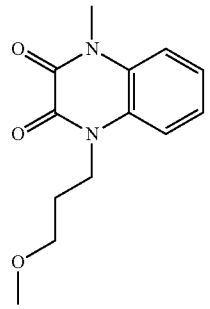

Compound 2

1-(3-methoxypropyl)-4-methylquinoxaline-2,3(1H,4H)-dione;

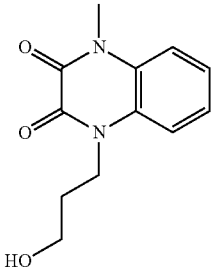

Compound 3

1-(3-hydroxypropyl)-4-methylquinoxaline-2,3(1H,4H)-dione;

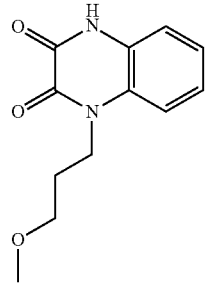

Compound 4

1-(3-methoxypropyl)quinoxaline-2,3(1H,4H)-dione;

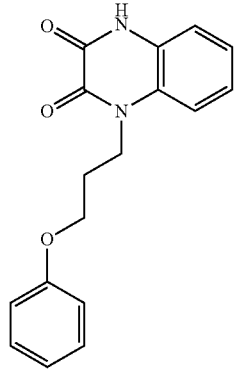
Compound 5

1-(3-phenoxypropyl)quinoxaline-2,3(1H,4H)-dione;

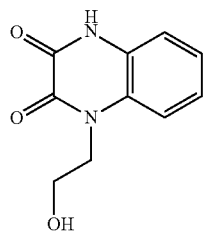
Compound 9

1-(2-hydroxyethyl)quinoxaline-2,3(1H,4H)-dione;

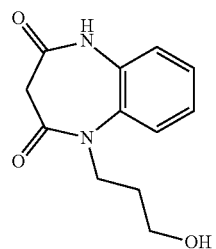
Compound 12

1-(3-hydroxypropyl)-1H-benzo[b][1,4]diazepine-2,4(3H,5H)-dione;

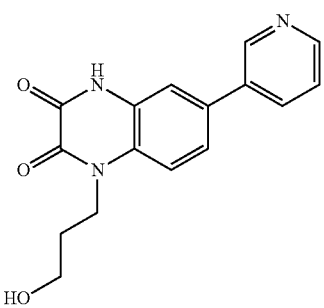
Compound 13

1-(3-hydroxypropyl)-6-(pyridin-3-yl)quinoxaline-2,3(1H,4H)-dione;

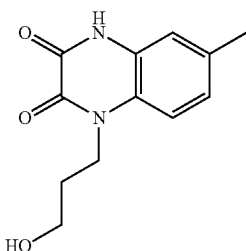
Compound 27

1-(3-hydroxypropyl)-6-methylquinoxaline-2,3(1H,4H)-dione;

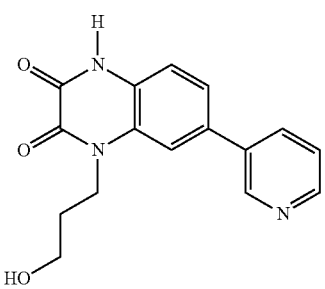
Compound 28

1-(3-hydroxypropyl)-7-(pyridin-3-yl)quinoxaline-2,3(1H,4H)-dione;

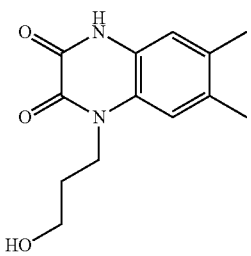
Compound 29

1-(3-hydroxypropyl)-6,7-dimethylquinoxaline-2,3(1H,4H)-dione;

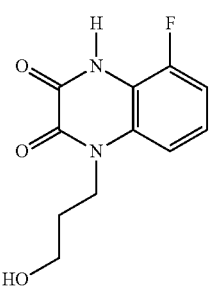
Compound 30

5-fluoro-1-(3-hydroxypropyl)quinoxaline-2,3(1H,4H)-dione;

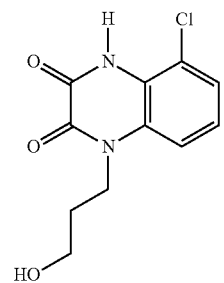

5-chloro-1-(3-hydroxypropyl)quinoxaline-2,3(1H,4H)-dione;

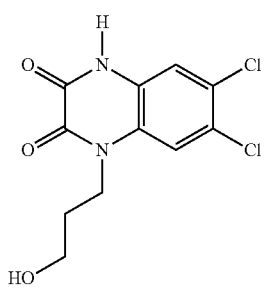

6,7-dichloro-1-(3-hydroxypropyl)quinoxaline-2,3(1H,4H)-dione;

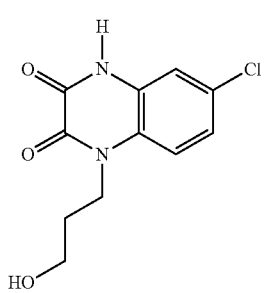

6-chloro-1-(3-hydroxypropyl)quinoxaline-2,3(1H,4H)-dione;

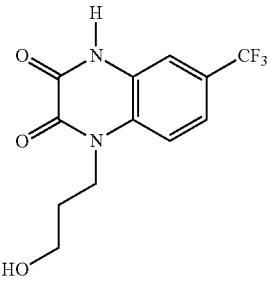

1-(3-hydroxypropyl)-6-(trifluoromethyl)quinoxaline-2,3(1H,4H)-dione;

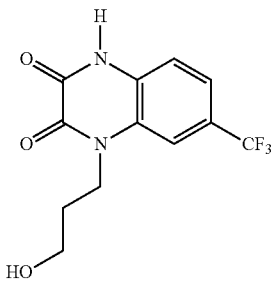

1-(3-hydroxypropyl)-7-(trifluoromethyl)quinoxaline-2,3(1H,4H)-dione;

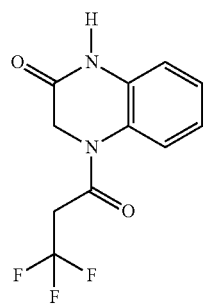

7-chloro-6-fluoro-1-(3-hydroxypropyl)quinoxaline-2,3(1H,4H)-dione;

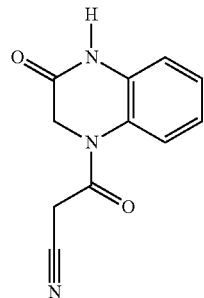

4-(3,3,3-trifluoropropanoyl)-3,4-dihydroquinoxalin-2(1H)-one;

3-oxo-3-(3-oxo-3,4-dihydroquinoxalin-1(2H)-yl)propanenitrile;

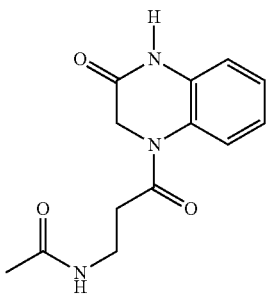

N-(3-oxo-3-(3-oxo-3,4-dihydroquinoxalin-1(2H)-yl)propyl)acetamide;

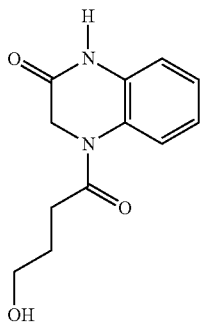

4-(4-hydroxybutanoyl)-3,4-dihydroquinoxalin-2(1H)-one; and

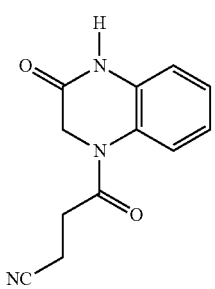

4-oxo-4-(3-oxo-3,4-dihydroquinoxalin-1(2H)-yl)butanenitrile.

Formula (IV)

In certain embodiments, the amylin receptor antagonist is a compound of formula (IV):

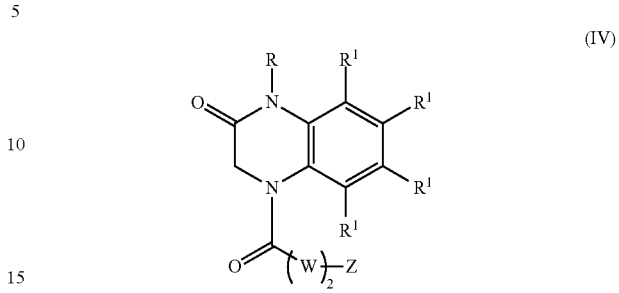

wherein:

R is selected from the group consisting of —H and $C_1$-$C_6$-alkyl;

each $R^1$ is independently selected from the group consisting of —H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;

each $R^2$ is independently selected from the group consisting of —H, and $C_1$-$C_6$-alkyl;

each W is independently selected from the group consisting of —$CH_2$—, —$CHR^3$— and —$CR^3R^4$—;

$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, or substituted carbocycle;

Z is selected from the group consisting of —OH, —OC(=O)$CH_3$, —OC(=O)Ph, and —NHC(=O)$CH_3$;

or an enantiomer, a mixture of enantiomers, a mixture of two or more diastereomers, a tautomer, a mixture of two or more tautomers, or an isotopic variant thereof;

or a pharmaceutically acceptable salt, solvate, or hydrate thereof;

with the proviso that the compound is not:
N-[3-(3,4-dihydro-3-oxo-1(2H)-quinoxalinyl)-3-oxopropyl]acetamide.

In certain embodiments, R is selected from —H and $C_1$-$C_6$-alkyl. For example, in some embodiments, R can be —H. In some embodiments, R can be $C_1$-$C_6$-alkyl (e.g., methyl, ethyl, propyl, butyl, pentyl, or hexyl).

In certain embodiments, each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl. For example, $R^1$ can be H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, or substituted heteroaryl. In some instances, $R^1$ is H. In some instances, $R^1$ is halogen (e.g., F, Cl, Br, I). In some instances, $R^1$ is $C_1$-$C_6$-alkyl (e.g., methyl, ethyl, propyl, butyl, pentyl, or hexyl) or substituted $C_1$-$C_6$-alkyl (e.g., substituted methyl (e.g., —$CF_3$), substituted ethyl, substituted propyl, substituted butyl, substituted pentyl, or substituted hexyl). In some instances, $R^1$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^1$ is —$OR^2$, such as —$OCH_3$. In some instances, $R^1$ is heterocyclyl or substituted heterocyclyl (e.g., unsubstituted or substituted pyrrolidinyl, imidazolidinyl, piperidinyl, piperazinyl, morpholinyl, and the like). In some instances, $R^1$ is aryl or substituted aryl (e.g., unsubstituted or substituted phenyl). In some instances, $R^1$ is heteroaryl or substituted heteroaryl (e.g., unsubstituted or substituted pyrrolyl, pyrazolyl, imidazolyl, pyridyl, pyrimidinyl, and the like).

In certain embodiments, each $R^2$ is independently selected from the group consisting of —H and $C_1$-$C_6$-alkyl. For example, in some embodiments, $R^2$ can be —H. In some embodiments, $R^2$ can be $C_1$-$C_6$-alkyl (e.g., methyl, ethyl, propyl, butyl, pentyl, or hexyl).

In certain embodiments, each W is selected from the group consisting of —$CH_2$—, —$CHR^3$— and —$CR^3R^4$—. In some instances, W is —$CH_2$—. In some instances, W is —$CHR^3$—. In some instances, W is —$CR^3R^4$—.

In certain embodiments, $R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle or substituted carbocycle.

For example, $R^3$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^3$ is halogen (e.g., F, Cl, Br, I). In some instances, $R^3$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^3$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^3$ is heterocyclyl or substituted heterocyclyl. In some instances, $R^3$ is aryl or substituted aryl (e.g., unsubstituted or substituted phenyl). In some instances, $R^3$ is heteroaryl or substituted heteroaryl. In some instances, $R^3$ is fused-heterocycle or substituted fused-heterocycle.

For example, $R^4$ can be halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, or substituted fused-heterocycle. In some instances, $R^4$ is halogen (e.g., F, Cl, Br, I). In some instances, $R^4$ is $C_1$-$C_6$-alkyl (e.g., methyl, ethyl, propyl, butyl, pentyl, or hexyl) or substituted $C_1$-$C_6$-alkyl (e.g., substituted methyl, substituted ethyl, substituted propyl, substituted butyl, substituted pentyl, or substituted hexyl). In some instances, $R^4$ is $C_3$-$C_6$-cycloalkyl (e.g., cyclopropyl, cyclobutyl, cyclopentyl, or cyclohexyl) or substituted $C_3$-$C_6$-cycloalkyl (e.g., substituted cyclopropyl, substituted cyclobutyl, substituted cyclopentyl, or substituted cyclohexyl). In some instances, $R^4$ is heterocyclyl or substituted heterocyclyl. In some instances, $R^4$ is aryl or substituted aryl (e.g., unsubstituted or substituted phenyl). In some instances, $R^4$ is heteroaryl or substituted heteroaryl. In some instances, $R^4$ is fused-heterocycle or substituted fused-heterocycle.

In certain embodiments, together $R^3$ and $R^4$ comprise a carbocycle or substituted carbocycle. In some instances, together $R^3$ and $R^4$ comprise a carbocycle, such as a $C_3$-$C_6$ carbocycle (e.g., cyclopropyl, cyclobutyl, cyclopentyl). In some instances, together $R^3$ and $R^4$ comprise a substituted carbocycle, such as a substituted $C_3$-$C_6$ carbocycle (e.g., substituted cyclopropyl, substituted cyclobutyl, substituted cyclopentyl.

In certain embodiments, Z is selected from the group consisting of —OH, —OC(=O)$CH_3$, —OC(=O)Ph, and —NHC(=O)$CH_3$. In some instances, Z is —OH. In some instances, Z is —OC(=O)$CH_3$. In some instances, Z is —OC(=O)Ph. In some instances, Z is —NHC(=O)$CH_3$.

Compounds of the present disclosure (e.g., compounds of formula (IV) as described herein) also include an enantiomer, a mixture of enantiomers, a mixture of two or more diastereomers, a tautomer, a mixture of two or more tautomers, or an isotopic variant thereof.

In addition, compounds of the present disclosure (e.g., compounds of formula (IV) as described herein) also include a pharmaceutically acceptable salt, solvate, or hydrate thereof.

In certain embodiments, compounds of the present disclosure (e.g., compounds that find use in the methods of the present disclosure) include compounds selected from:

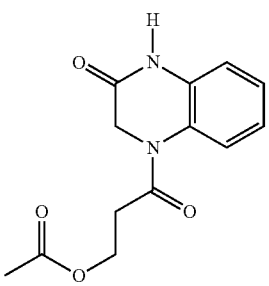

Compound 6

3-oxo-3-(3-oxo-3,4-dihydroquinoxalin-1(2H)-yl)propyl acetate;

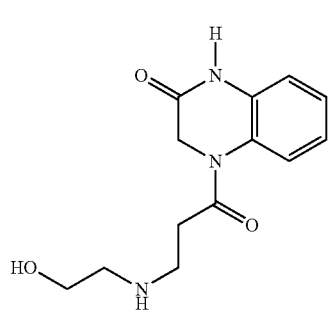

Compound 7

4-(3-(2-hydroxyethylamino)propanoyl)-3,4-dihydroquinoxalin-2(1H)-one;

Compound 8

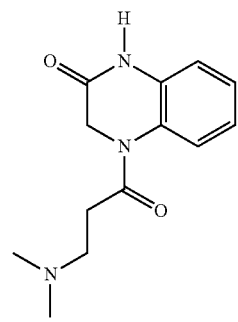

4-(3-(dimethylamino)propanoyl)-3,4-dihydroquinoxalin-2(1H)-one;

Compound 10

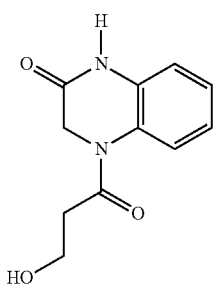

4-(3-hydroxypropanoyl)-3,4-dihydroquinoxalin-2(1H)-one;

Compound 14

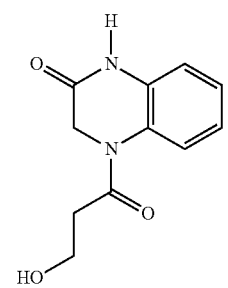

N,N-dimethyl-3-oxo-3-(3-oxo-3,4-dihydroquinoxalin-1(2H)-yl)propanamide;

Compound 15

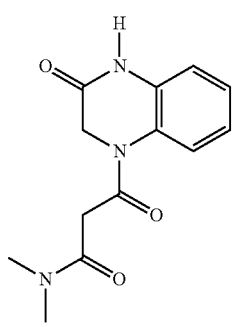

4-(3-hydroxypropanoyl)-4,5-dihydro-1H-benzo[e][1,4]diazepin-2(3H)-one;

Compound 11

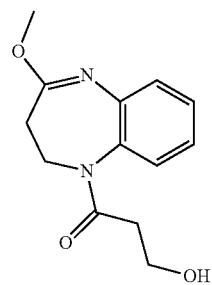

3-hydroxy-1-(4-methoxy-2,3-dihydro-1H-benzo[b][1,4]diazepin-1-yl)propan-1-one;

Compound 16

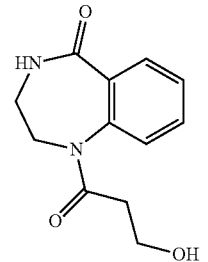

1-(3-hydroxypropanoyl)-3,4-dihydro-1H-benzo[e][1,4]diazepin-5(2H)-one;

Compound 17

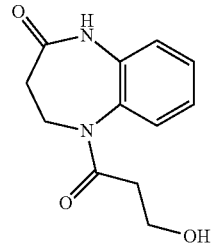

5-(3-hydroxypropanoyl)-4,5-dihydro-1H-benzo[b][1,4]diazepin-2(3H)-one;

Compound 18

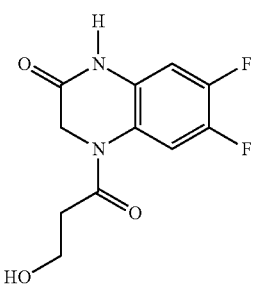

6,7-difluoro-4-(3-hydroxypropanoyl)-3,4-dihydroquinoxalin-2(1H)-one;

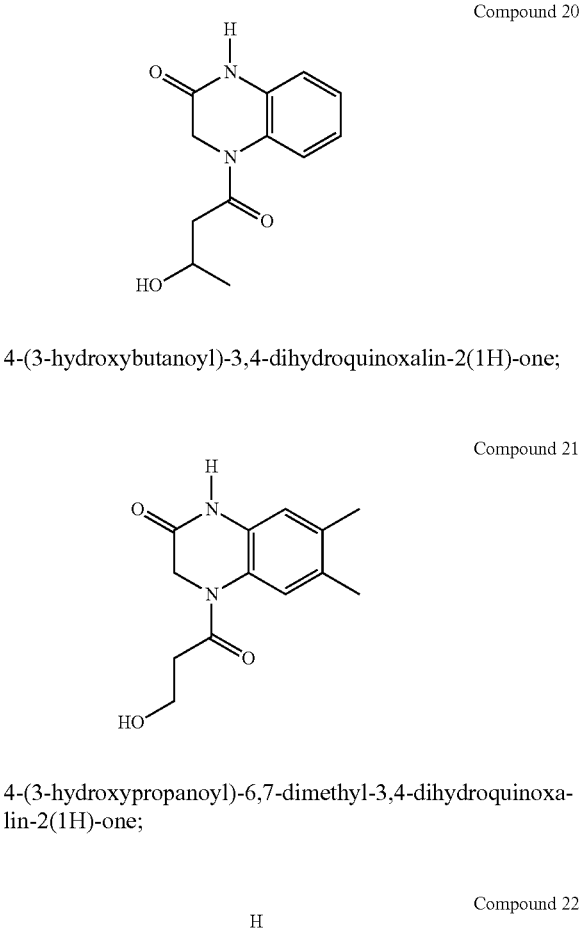

Compound 20

4-(3-hydroxybutanoyl)-3,4-dihydroquinoxalin-2(1H)-one;

Compound 21

4-(3-hydroxypropanoyl)-6,7-dimethyl-3,4-dihydroquinoxalin-2(1H)-one;

Compound 22

4-(3-hydroxycyclobutanecarbonyl)-3,4-dihydroquinoxalin-2(1H)-one;

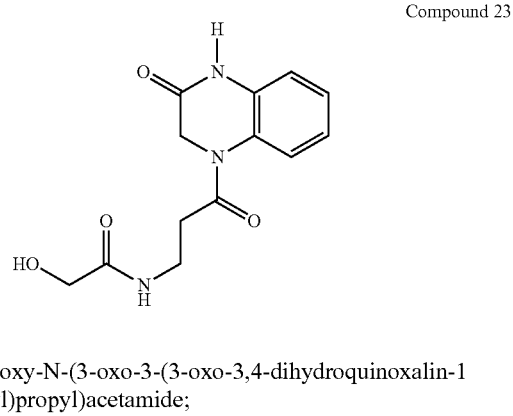

Compound 23

2-hydroxy-N-(3-oxo-3-(3-oxo-3,4-dihydroquinoxalin-1(2H)-yl)propyl)acetamide;

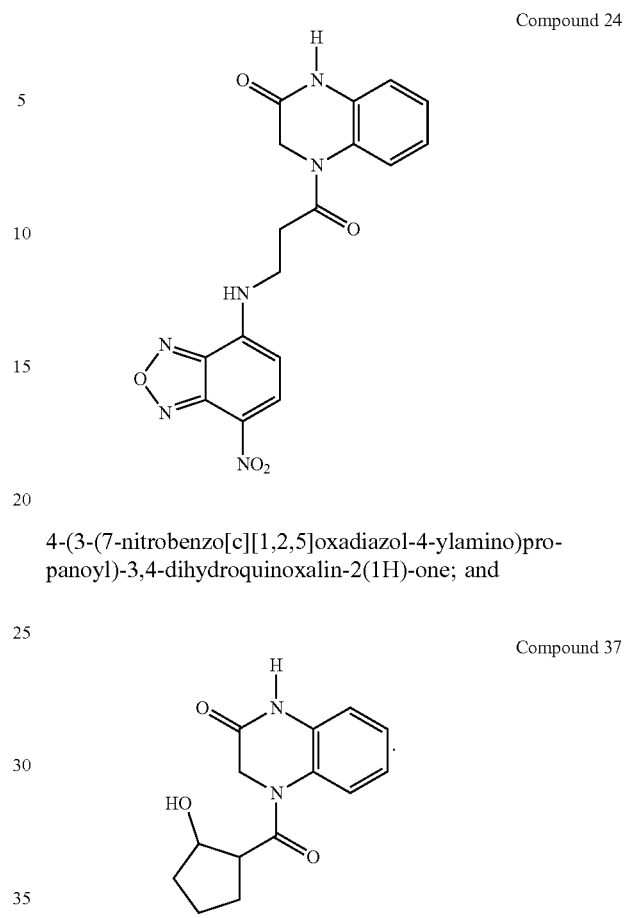

Compound 24

4-(3-(7-nitrobenzo[c][1,2,5]oxadiazol-4-ylamino)propanoyl)-3,4-dihydroquinoxalin-2(1H)-one; and Compound 37

4-(2-hydroxycyclopentanecarbonyl)-3,4-dihydroquinoxalin-2(1H)-one.

In certain embodiments, the compound of formula (IV) does not include N-[3-(3,4-dihydro-3-oxo-1(2H)-quinoxalinyl)-3-oxopropyl]acetamide.

Formula (V), Formula (VI) and Formula (VII)

In certain embodiments, the amylin receptor antagonist is a compound of formula (V), formula (VI) or formula (VII):

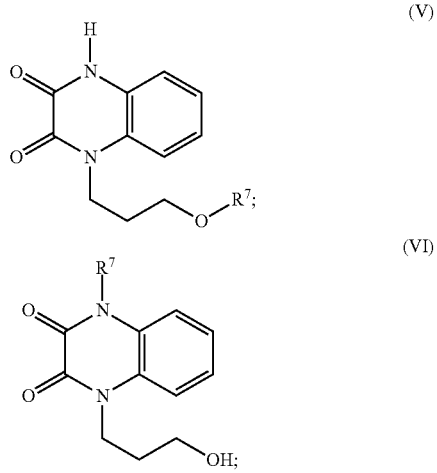

(V)

(VI)

-continued

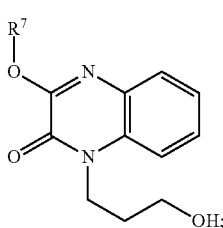

(VII)

wherein:
R⁷ is selected from the group consisting of —CH₂OC(=O)OR⁸, —C(CH₃)HOC(=O)OR⁸, —C(=O)R⁸, —C(=O)OR⁸, —C(=O)NHR⁸, —C(=O)NR⁸R⁸, and C₁-C₆-alkyl; and
each R⁸ is independently selected from C₁-C₆-alkyl, substituted C₂-C₆-alkyl, C₃-C₆-cycloalkyl, substituted C₃-C₆-cycloalkyl, heterocycyl, substituted heterocycyl, aryl, substituted aryl, heteroaryl, and substituted heteroaryl,
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

In certain embodiments, R⁷ is selected from the group consisting of —CH₂OC(=O)OR⁸, —C(CH₃)HOC(=O)OR⁸, —C(=O)R⁸, —C(=O)OR⁸, —C(=O)NHR⁸, —C(=O)NR⁸R⁸, and C₁-C₆-alkyl. In some instances, R⁷ is —CH₂OC(=O)OR⁸. In some instances, R⁷ is —C(CH₃)HOC(=O)OR⁸. In some instances, R⁷ is —C(=O)R⁸. In some instances, R⁷ is —C(=O)OR⁸. In some instances, R⁷ is —C(=O)NHR⁸. In some instances, R⁷ is —C(=O)NR⁸R⁸. In some instances, R⁷ is C₁-C₆-alkyl.

In certain embodiments, each R⁸ is independently selected from C₁-C₆-alkyl, substituted C₂-C₆-alkyl, C₃-C₆-cycloalkyl, substituted C₃-C₆-cycloalkyl, heterocycyl, substituted heterocycyl, aryl, substituted aryl, heteroaryl, and substituted heteroaryl. For example, R⁸ can be C₁-C₆-alkyl alkyl (e.g., methyl, ethyl, propyl, butyl, pentyl, or hexyl) or substituted C₂-C₆-alkyl (e.g., substituted ethyl, substituted propyl, substituted butyl, substituted pentyl, or substituted hexyl). In some instances, R⁸ is C₃-C₆-cycloalkyl (e.g., cyclopropyl, cyclobutyl, cyclopentyl, or cyclohexyl) or substituted C₃-C₆-cycloalkyl (e.g., substituted cyclopropyl, substituted cyclobutyl, substituted cyclopentyl, or substituted cyclohexyl). In some instances, R⁸ is heterocyclyl or substituted heterocyclyl (e.g., unsubstituted or substituted pyrrolidinyl, imidazolidinyl, piperidinyl, piperazinyl, morpholinyl, and the like). In some instances, R⁸ is aryl or substituted aryl (e.g., unsubstituted or substituted phenyl). In some instances, R⁸ is heteroaryl or substituted heteroaryl (e.g., unsubstituted or substituted pyrrolyl, pyrazolyl, imidazolyl, pyridinyl, pyrimidinyl, and the like).

Compounds of the present disclosure (e.g., compounds of formula (V), formula (VI) or formula (VII) as described herein) also include an enantiomer, a mixture of enantiomers, a mixture of two or more diastereomers, a tautomer, a mixture of two or more tautomers, or an isotopic variant thereof.

In addition, compounds of the present disclosure (e.g., compounds of formula (V), formula (VI) or formula (VII) as described herein) also include a pharmaceutically acceptable salt, solvate, or hydrate thereof.

In certain embodiments, compounds of the present disclosure (e.g., compounds that find use in the methods of the present disclosure) include compounds selected from:

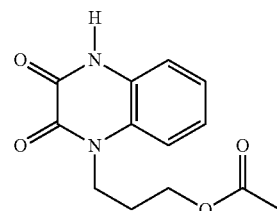

Compound 51

3-(2,3-dioxo-3,4-dihydroquinoxalin-1(2H)-yl)propyl acetate;

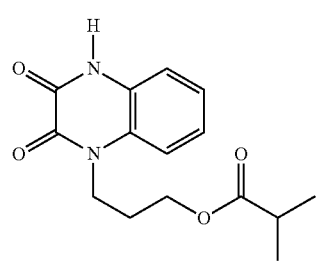

Compound 41

3-(2,3-dioxo-3,4-dihydroquinoxalin-1(2H)-yl)propyl isobutyrate;

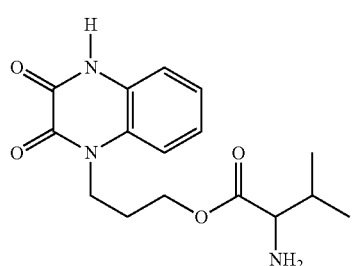

Compound 42

3-(2,3-dioxo-3,4-dihydroquinoxalin-1(2H)-yl)propyl 2-amino-3-methylbutanoate;

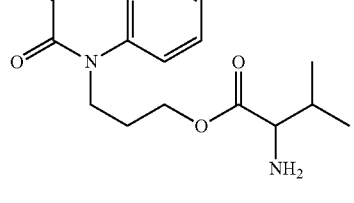

Compound 48

3-(2,3-dioxo-3,4-dihydroquinoxalin-1(2H)-yl)propyl benzoate;

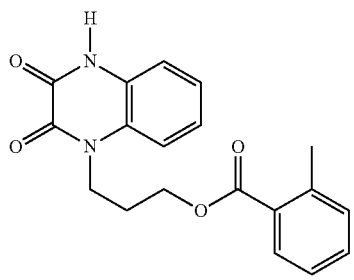 [SMILES: Cc1ccccc1C(=O)OCCCn1c(=O)c(=O)[nH]c2ccccc21]

Compound 46
3-(2,3-dioxo-3,4-dihydroquinoxalin-1(2H)-yl)propyl 2-methylbenzoate;

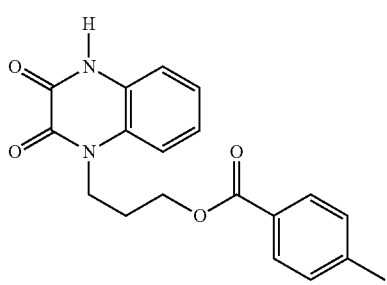

Compound 47
3-(2,3-dioxo-3,4-dihydroquinoxalin-1(2H)-yl)propyl 4-methylbenzoate;

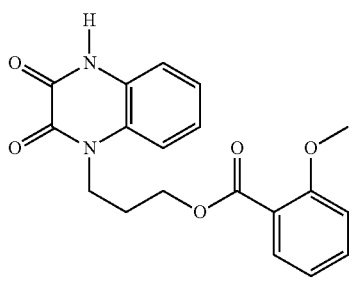

Compound 49
3-(2,3-dioxo-3,4-dihydroquinoxalin-1(2H)-yl)propyl 2-methoxybenzoate;

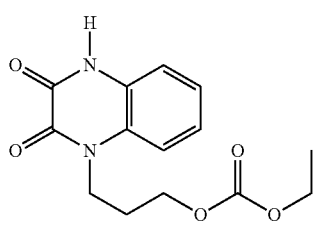

Compound 52
3-(2,3-dioxo-3,4-dihydroquinoxalin-1(2H)-yl)propyl ethyl carbonate;

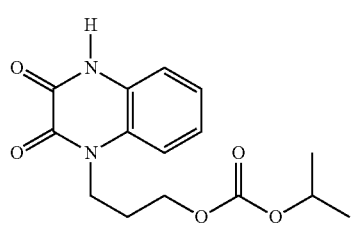

Compound 53
3-(2,3-dioxo-3,4-dihydroquinoxalin-1(2H)-yl)propyl isopropyl carbonate;

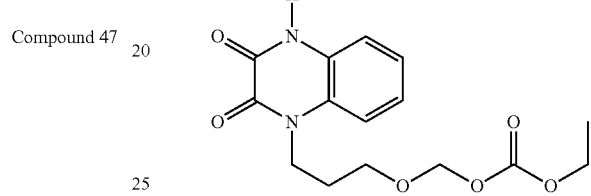

Compound 54
(3-(2,3-dioxo-3,4-dihydroquinoxalin-1(2H)-yl)propoxy)methyl ethyl carbonate;

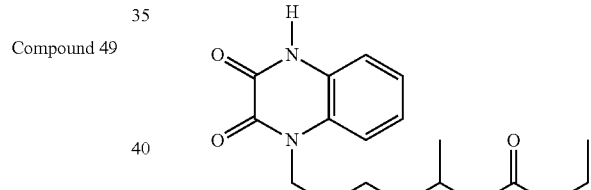

Compound 55
1-(3-(2,3-dioxo-3,4-dihydroquinoxalin-1(2H)-yl)propoxy)ethyl ethyl carbonate;

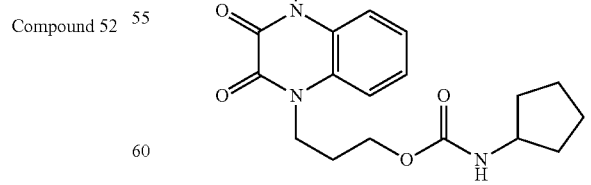

Compound 56
3-(2,3-dioxo-3,4-dihydroquinoxalin-1(2H)-yl)propyl cyclopentylcarbamate;

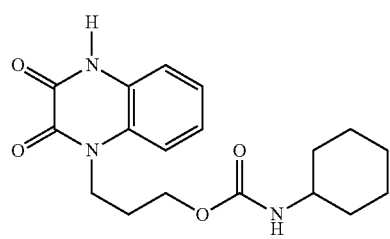

Compound 50

3-(2,3-dioxo-3,4-dihydroquinoxalin-1(2H)-yl)propyl cyclohexylcarbamate;

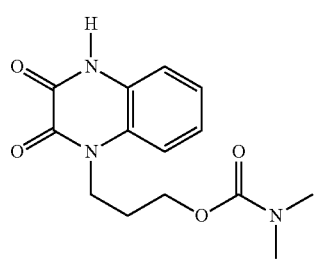

Compound 57

3-(2,3-dioxo-3,4-dihydroquinoxalin-1(2H)-yl)propyl dimethylcarbamate;

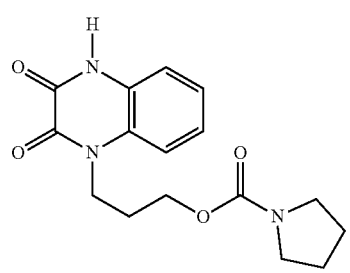

Compound 58

3-(2,3-dioxo-3,4-dihydroquinoxalin-1(2H)-yl)propyl pyrrolidine-1-carboxylate;

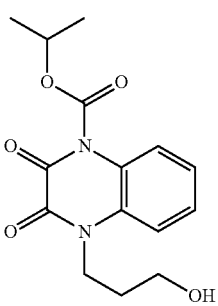

Compound 43 isopropyl 4-(3-hydroxypropyl)-2,3-dioxo-3,4-dihydroquinoxaline-1(2H)-carboxylate;

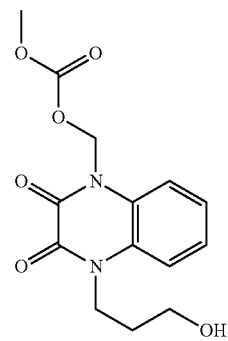

Compound 44

(4-(3-hydroxypropyl)-2,3-dioxo-3,4-dihydroquinoxalin-1(2H)-yl)methyl methyl carbonate;

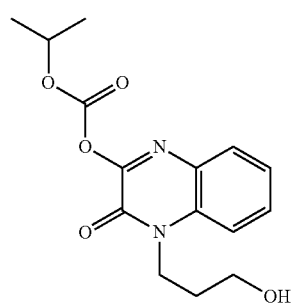

Compound 59 ethyl (4-(3-hydroxypropyl)-2,3-dioxo-3,4-dihydroquinoxalin-1(2H)-yl)methyl carbonate;

Compound 60

4-(3-hydroxypropyl)-3-oxo-3,4-dihydroquinoxalin-2-yl isopropyl carbonate; and

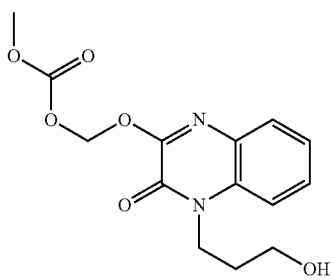

Compound 45

(4-(3-hydroxypropyl)-3-oxo-3,4-dihydroquinoxalin-2-yloxy)methyl methyl carbonate.

In certain embodiments, a compound of formula (V), formula (VI) and formula (VII) is a prodrug of a compound of formula (I), formula (II) or formula (III) as described herein. Embodiments of prodrugs of compounds of formula (IV) are also provided by the disclosure herein.

The term "prodrug" refers to a derivative of an active compound (e.g., a drug or active agent) that undergoes a transformation under the conditions of use, such as within the body, to release the active compound. Prodrugs may be, but are not necessarily, pharmacologically inactive until converted into the active drug. In some cases, prodrugs are pharmacologically inactive until converted into the active drug. In certain cases, compounds that include a progroup may facilitate removal of the progroup at a desired site of action for the pharmaceutically active form of the compound, or after a desired amount of time after administration of the compound (e.g., delayed release formulations, controlled release formulations, and the like). A wide variety of progroups, as well as the resultant promoieties, suitable for masking functional groups in the active drugs to yield prodrugs may be used. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art.

In some instances, prodrugs may be obtained by masking a functional group in the drug believed to be in part required for activity with a progroup to form a promoiety which undergoes a transformation, such as cleavage, under the specified conditions of use to release the active drug. The cleavage of the promoiety can proceed spontaneously, such as by way of a hydrolysis or oxidation reaction, or it can be catalyzed or induced by another agent, such as by an enzyme (e.g., cytochrome P450, an esterase, a peptidase, and the like), by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. For example, in certain cases, compounds that include a progroup may facilitate an increase in gastrointestinal permeability, an increase in gastrointestinal absorption, and/or an increase in solubility of the compound.

The prodrugs of the present disclosure include compounds of the formulae described herein. Pharmaceutical compositions of the prodrugs and methods of use involving the prodrugs of the present disclosure are also contemplated herein.

Methods of Use

The compounds of the present disclosure find use in treatment of a condition or disease in a subject that is amenable to treatment by administration of the compound. Thus, in some embodiments, provided are methods that include administering to a subject a therapeutically effective amount of any of the compounds of the present disclosure. In certain aspects, provided are methods of delivering a compound to a target site in a subject, the method including administering to the subject a pharmaceutical composition including any of the compounds of the present disclosure, where the administering is effective to provide a therapeutically effective amount of the compound at the target site in the subject.

The subject to be treated can be one that is in need of therapy, where the subject to be treated is one amenable to treatment using the compounds disclosed herein. Accordingly, a variety of subjects may be amenable to treatment using the compounds disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The present disclosure provides methods that include delivering a compound of the present disclosure to an individual having Alzheimer's disease, such as methods that include administering to the subject a therapeutically effective amount of a compound of the present disclosure. The methods are useful for treating a wide variety of conditions and/or symptoms associated with Alzheimer's disease. In the context of Alzheimer's disease, the term "treating" includes one or more (e.g., each) of: reducing the severity of one or more symptoms, inhibiting the progression, reducing the duration of one or more symptoms, and ameliorating one or more symptoms associated with Alzheimer's disease. In certain embodiments, methods of the present disclosure include administering a compound of the present disclosure to a subject, where the administering is effective for treating a disease mediated through activity of the amylin receptor. In some instances, compounds of the present disclosure are effective for inhibiting the activity of the amylin receptor.

The compounds described herein can be isolated by procedures known to those skilled in the art. The compounds described herein may be obtained, for instance, by a resolution technique or by chromatography techniques (e.g., silica gel chromatography, chiral chromatography, etc.). As used herein, the term "isolated" refers to compounds that are non-naturally occurring and can be obtained or purified from synthetic reaction mixtures. Isolated compounds may find use in the pharmaceutical compositions and methods of treatment described herein.

The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^2H$; D) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%. In some embodiments, one or more (e.g., 1, 2, 3, 4, 5, 6, 7 or more) hydrogen atoms of a substituent group (e.g., an R-group) of any one of the subject compounds described herein are substituted with a deuterium.

Pharmaceutical Compositions

In certain embodiments, the disclosed compounds are useful for the treatment of a disease or disorder, such as Alzheimer's disease. Accordingly, pharmaceutical compositions comprising at least one disclosed compound are also described herein. For example, the present disclosure provides pharmaceutical compositions that include a therapeutically effective amount of a compound of the present disclosure (or a pharmaceutically acceptable salt or solvate or hydrate or stereoisomer thereof) and a pharmaceutically acceptable excipient.

A pharmaceutical composition that includes a subject compound may be administered to a patient alone, or in combination with other supplementary active agents. For example, one or more compounds according to the present disclosure can be administered to a patient with or without supplementary active agents. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, spray dried dispersion, lyophilisate, tablet, microtablets, pill, pellet, capsule, powder, syrup, elixir or any other dosage form suitable for administration.

A compound of the present disclosure may be administered to a subject using any convenient means capable of resulting in the desired reduction in disease condition or symptom. Thus, a compound can be incorporated into a variety of formulations for therapeutic administration. More particularly, a compound can be formulated into pharmaceutical compositions by combination with appropriate pharmaceutically acceptable excipients, carriers or diluents, and may be formulated into preparations in solid, semi-solid, liquid or gaseous forms, such as tablets, capsules, powders, granules, ointments, solutions, suppositories, injections, inhalants, aerosols, and the like.

Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of the disclosed compounds. Pharmaceutical compositions that include at least one of the compounds can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable excipient in addition to at least one active ingredient, such as a compound of the present disclosure. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. In addition to biologically neutral carriers, pharmaceutical compositions to be administered can optionally contain non-toxic auxiliary substances (e.g., excipients), such as wetting or emulsifying agents, preservatives, and pH buffering agents, and the like. The disclosed pharmaceutical compositions may be formulated as a pharmaceutically acceptable salt of a disclosed compound.

In some embodiments, the disclosed pharmaceutical compositions may be formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. A BBB disrupting agent can be co-administered with the pharmaceutical compositions disclosed herein when the compositions are administered by intravenous injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to a compound disclosed herein for use in the methods disclosed herein to facilitate transport across the epithelial wall of the blood vessel. Alternatively, drug delivery behind the BBB may be by intrathecal delivery of therapeutics, e.g., administering the disclosed pharmaceutical compositions directly to the cranium, as through an Ommaya reservoir.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, excipient, carrier or vehicle. The specifications for a compound depend on the particular compound employed and the effect to be achieved, and the pharmacodynamics associated with each compound in the subject.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions that include a subject compound may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual compound may be administered at the same time as another therapeutic compound or sequentially, in any order thereof.

A disclosed compound can be administered alone, as the sole active pharmaceutical agent, or in combination with one or more additional compounds of the present disclosure or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of the present disclosure optionally include other therapeutic agents. Accordingly, certain embodiments are directed to such pharmaceutical compositions, where the composition further includes a therapeutically effective amount of an agent selected as is known to those of skill in the art.

Methods of Administration

The subject compounds find use for treating a disease or disorder in a subject, such as Alzheimer's disease. The route of administration may be selected according to a variety of factors including, but not limited to, the condition to be treated, the formulation and/or device used, the subject to be treated, and the like. Routes of administration useful in the disclosed methods include, but are not limited to, oral and parenteral routes, such as intravenous (iv), intraperitoneal (ip), rectal, topical, ophthalmic, nasal, intrathecal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (e.g., patient) being treated. For example, this may be the amount of a subject compound necessary to prevent, inhibit, reduce or relieve a disease or disorder in a subject, such as Alzheimer's disease. Ideally, a therapeutically effective amount of a compound is an amount sufficient to prevent, inhibit, reduce or relieve a disease or disorder in a subject without causing a substantial cytotoxic effect on host cells in the subject.

Therapeutically effective doses of a subject compound or pharmaceutical composition can be determined by one of skill in the art. For example, in some instances, a therapeutically effective dose of a compound or pharmaceutical composition is administered with a goal of achieving local (e.g., tissue) concentrations that are at least as high as the $EC_{50}$ of an applicable compound disclosed herein.

The specific dose level and frequency of dosage for any particular subject may be varied and may depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

In some embodiments, multiple doses of a compound are administered. The frequency of administration of a compound can vary depending on any of a variety of factors, e.g., severity of the symptoms, condition of the subject, etc. For example, in some embodiments, a compound is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds, including compounds that are not commercially available, can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

In certain embodiments, compounds of Formula (I) are synthesized using methods and conditions that are known to one of ordinary skill in the art, as depicted in Scheme 1:

leaving group can be accomplished by one of ordinary skilled in the art. Regarding a nitrogen protecting group, a non-limiting example is a t-butylcarbonate (Boc) group, which will allow protection of one nitrogen and let reaction occur at the other nitrogen. Selective removal of the protecting group is well documented in the literature and is of common knowledge to one of ordinary skill in the art. For example, removal of a Boc group can be accomplished with acid, such as trifluoroacetic acid or hydrochloric acid. For the leaving groups, some non-limiting examples are chloride, mesylate, and —O(C=O)OtBu, which will allow the desired nitrogen carbon bond to be formed. The selection of base will depend on the nature of the bond being created and functional groups present and some non-limiting examples are: triethylamine, pyridine, N,N-diisopropylethylamine, sodium hydride, potassium tert-butoxide and potassium carbonate.

In certain embodiments, compounds of Formula (II) are synthesized using methods and conditions that are known to one of ordinary skill in the art, as depicted in Scheme 2:

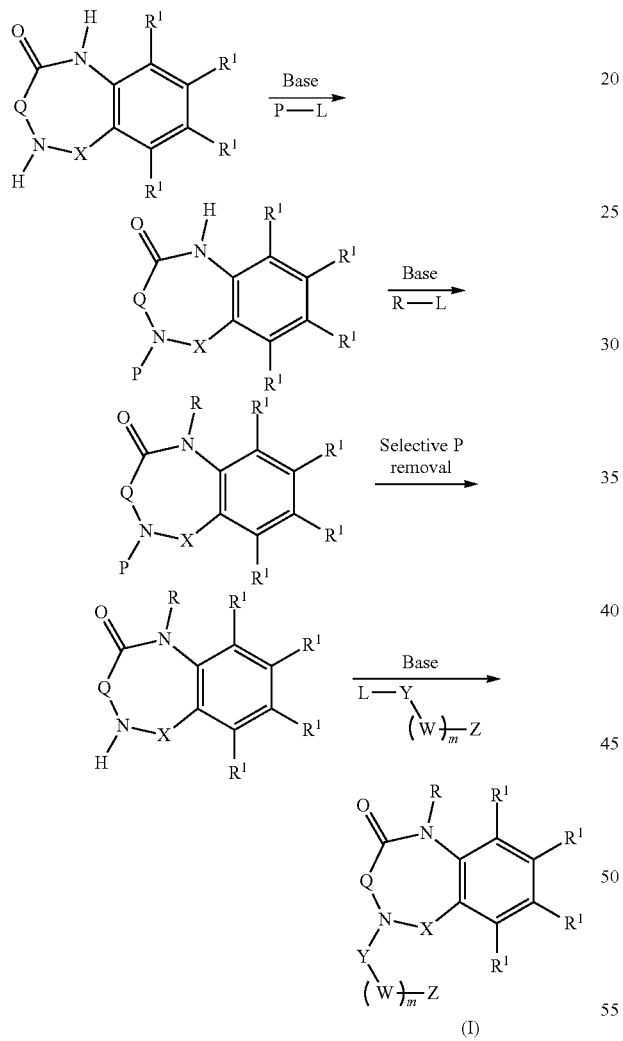

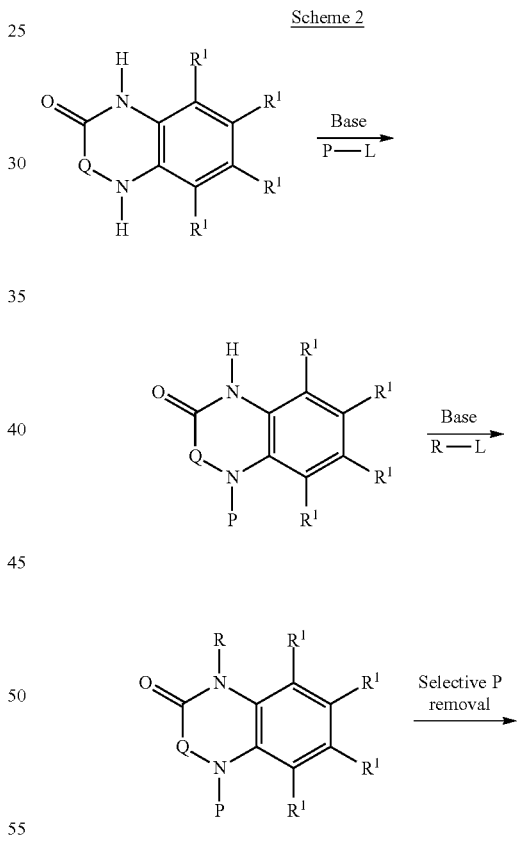

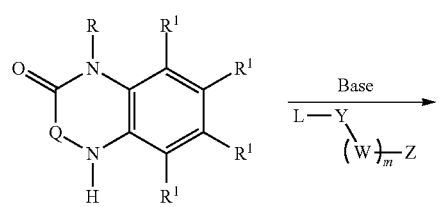

P = protecting group
L = leaving group wherein R, R¹, m, Q, W, X, Y, and Z are as defined herein.

The starting materials and reagents employed in Scheme 1 may be obtained commercially or through techniques known to one of ordinary skill in the art. Scheme 1 is an example of a method to generate compounds of Formula (I) where the exact steps and materials will depend on the functional groups present. The selection of the starting materials, reagent, substrates, base, protecting, solvent and -continued

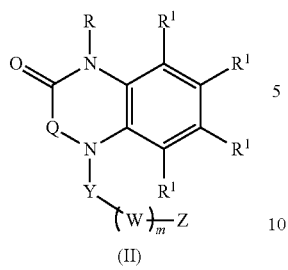

(II)

P = protecting group
L = leaving group wherein R, R¹, m, Q, W, Y, and Z are as defined herein.

The starting materials and reagents employed in Scheme 2 may be obtained commercially or through techniques known to one of ordinary skill in the art. Scheme 2 is an example of a method to generate compounds of Formula (II) where the exact steps and materials will depend on the functional groups present. The selection of the starting materials, reagent, substrates, base, protecting, solvent and leaving group can be accomplished by one of ordinary skilled in the art. Regarding a nitrogen protecting group, a non-limiting example is a t-butylcarbonate (Boc) group, which will allow protection of one nitrogen and let reaction occur at the other nitrogen. Selective removal of the protecting group is well documented in the literature and is of common knowledge to one of ordinary skill in the art. For example, removal of a Boc group can be accomplished with acid, such as trifluoroacetic acid or hydrochloric acid. For the leaving groups, some non-limiting examples are chloride, mesylate, and —O(C=O)OtBu, which will allow the desired nitrogen carbon bond to be formed. The selection of base will depend on the nature of the bond being created and functional groups present and some non-limiting examples are: triethylamine, pyridine, N,N-diisopropylethylamine, sodium hydride, potassium tert-butoxide and potassium carbonate.

In certain embodiments, compounds of Formula (III) are synthesized using methods and conditions that are known to one of ordinary skill in the art, as depicted in Scheme 3:

Scheme 3

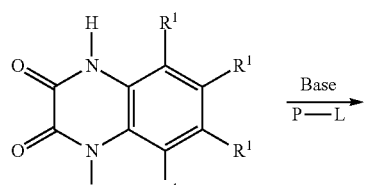

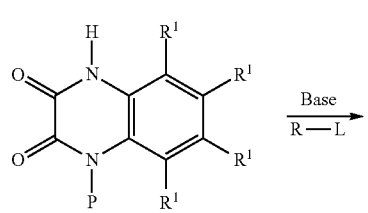

-continued

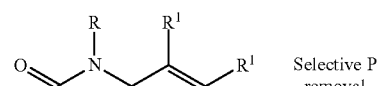

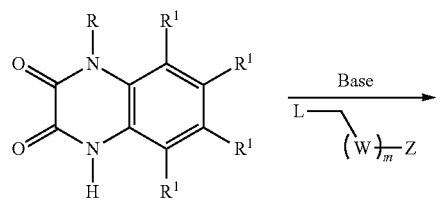

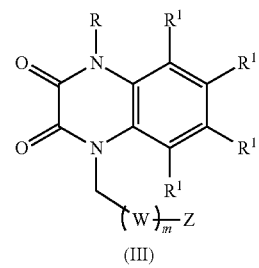

(III)

P = protecting group
L = leaving group wherein R, R¹, m, W and Z are as defined herein.

The starting materials and reagents employed in Scheme 3 may be obtained commercially or through techniques known to one of ordinary skill in the art. Scheme 3 is an example of a method to generate compounds of Formula (III) where the exact steps and materials will depend on the functional groups present. The selection of the starting materials, reagent, substrates, base, protecting, solvent and leaving group can be accomplished by one of ordinary skilled in the art. Regarding a nitrogen protecting group, a non-limiting example is a t-butylcarbonate (Boc) group, which will allow protection of one nitrogen and let reaction occur at the other nitrogen. Selective removal of the protecting group is well documented in the literature and is of common knowledge to one of ordinary skill in the art. For example, removal of a Boc group can be accomplished with acid, such as trifluoroacetic acid or hydrochloric acid. For the leaving groups, some non-limiting examples are chloride, mesylate, and —O(C=O)OtBu, which will allow the desired nitrogen carbon bond to be formed. The selection of base will depend on the nature of the bond being created and functional groups present and some non-limiting examples are: triethylamine, pyridine, N,N-diisopropylethylamine, sodium hydride, potassium tert-butoxide and potassium carbonate.

In certain embodiments, compounds of Formula (IV) are synthesized using methods and conditions that are known to one of ordinary skill in the art, as depicted in Scheme 4:

Scheme 4

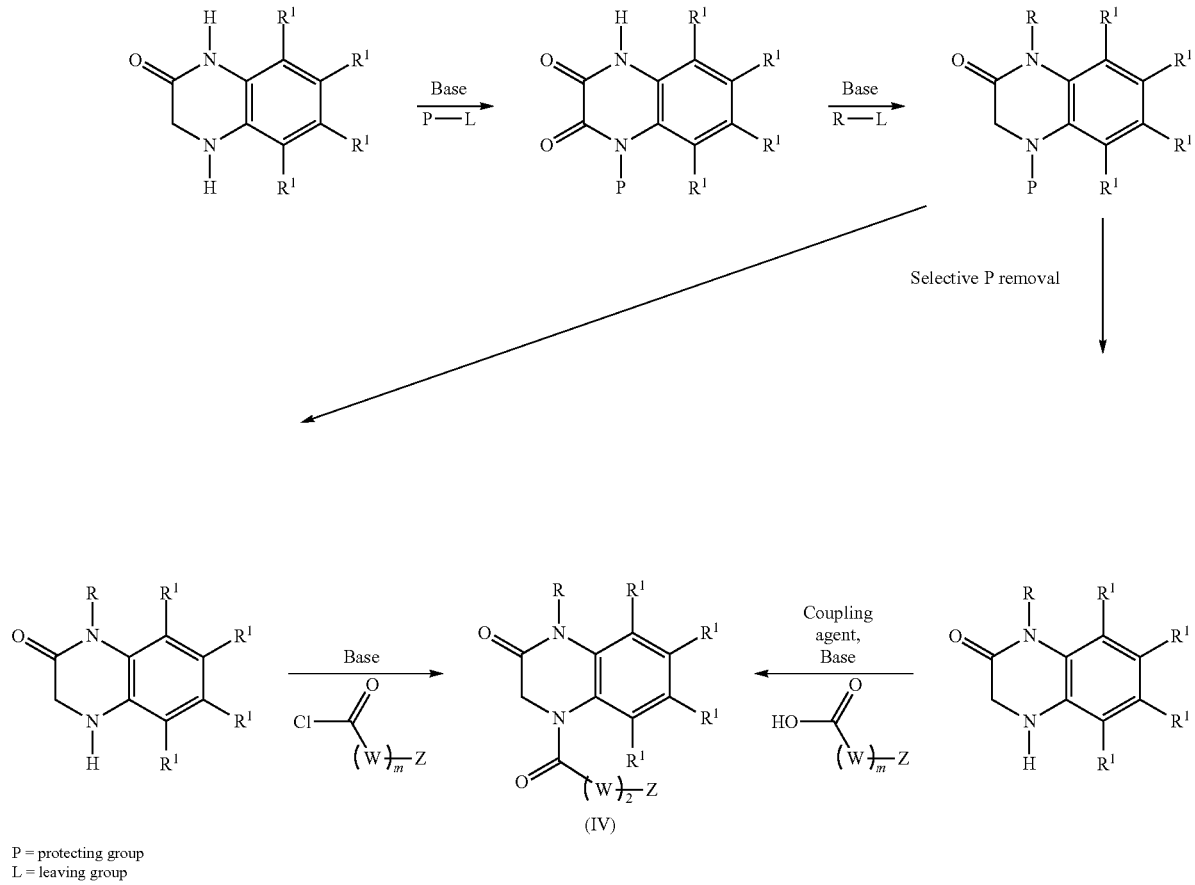

P = protecting group
L = leaving group wherein R, R¹, m, W and Z are as defined herein.

The starting materials and reagents employed in Scheme 4 may be obtained commercially or through techniques known to one of ordinary skill in the art. Scheme 4 is an example of a method to generate compounds of Formula (IV) where the exact steps and materials will depend on the functional groups present. The selection of the starting materials, reagent, substrates, base, protecting, solvent and leaving group can be accomplished by one of ordinary skilled in the art. Regarding a nitrogen protecting group, a non-limiting example is a t-butylcarbonate (Boc) group, which will allow protection of one nitrogen and let reaction occur at the other nitrogen. Selective removal of the protecting group is well documented in the literature and is of common knowledge to one of ordinary skill in the art. For example, removal of a Boc group can be accomplished with acid, such as trifluoroacetic acid or hydrochloric acid. For the leaving groups, some non-limiting examples are chloride, mesylate, and —O(C=O)OtBu, which will allow the desired nitrogen carbon bond to be formed. The selection of base will depend on the nature of the bond being created and functional groups present and some non-limiting examples are: triethylamine, pyridine, N,N-diisopropylethylamine, sodium hydride, potassium tert-butoxide and potassium carbonate.

In certain embodiments, compounds of Formula (V), (VI), and (VII) are synthesized using methods and conditions that are known to one of ordinary skill in the art, as depicted in Scheme 5:

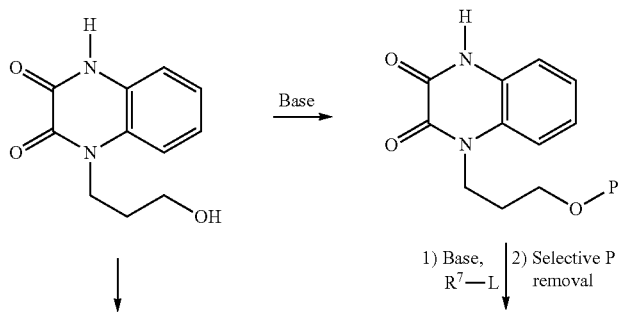

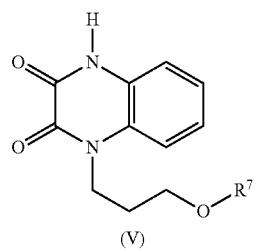 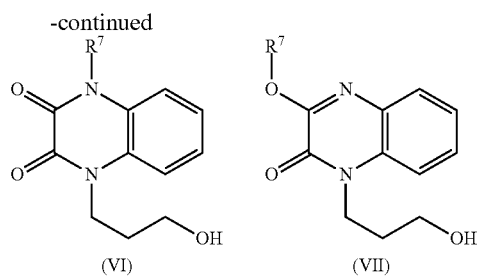

P = protecting group
L = leaving group wherein $R^7$ is defined herein.

The starting materials and reagents employed in Scheme 5 may be obtained commercially or through techniques known to one of ordinary skill in the art and documented in the examples herein. Scheme 5 is an example of methods to generate compounds of Formula (V), Formula (VI) and Formula (VII) where the exact steps and materials will depend on the functional groups present. The selection of the starting materials, reagent, substrates, base, protecting, solvent and leaving group can be accomplished by one of ordinary skilled in the art. For an oxygen protecting group, a non-limiting example is a t-butyldimethylsilyl group, which will allow protection of the alcohol oxygen. Selective removal of the protecting group is well documented in the literature and is of common knowledge to one of ordinary skill in the art. For example, removal of a t-butyldimethylsilyl group can be accomplished with fluoride, such as tetrabutylammonium fluoride or pyridinium hydrogen fluoride or KF. For the leaving groups, some non-limiting examples are chloride, mesylate, and —O(C=O)OtBu, which will allow the desired nitrogen carbon bond to be formed. The selection of base will depend on the nature of the bond being created and functional groups present and some non-limiting examples are: triethylamine, pyridine, N,N-diisopropylethylamine, sodium hydride, potassium tert-butoxide and potassium carbonate.

Schemes 1, 2, 3, 4 and 5 are meant to be by way of non-limiting examples only, and one of ordinary skill in the art will understand that alternate reagents, solvents or starting materials can be used to make compounds of Formula (I) and/or (II) and/or (III) and/or (IV) and/or (V) and/or (VI) and/or (VII) and/or other compounds contained herein.

Example 1: Synthesis of Compounds

All reagents and solvents were used as purchased from commercial sources. Moisture sensitive reactions were carried out under a nitrogen atmosphere. Reactions were monitored by TLC using pre-coated silica gel aluminum plates containing a fluorescent indicator (F-254). Detection was done with UV (254 nm). Alternatively, the progress of a reaction was monitored by LC/MS. Specifically, but without limitation, the following abbreviations were used, in addition to the other ones described herein, in the examples: Bn (benzyl); Boc (tert-butoxycarbonyl); Boc$_2$O (di-tert-butyl dicarbonate); cat. (catalytic amount); DCM (dichloromethane); dioxane (1,4-dioxane); DIPEA (N,N-diisopropylethylamine); DMAP (4-dimethylaminopyridine); DMF (N,N-dimethylformamide); EDCI (N-ethyl-N'-carbodiimide); EtOH (ethanol); ether or Et$_2$O (diethyl ether); Et$_3$N (triethylamine); HATU (1-[bis(dimethylamino)methylene]-1H-1,2,3-triazolo[4,5-b]pyridinium 3-oxide hexafluorophosphate or N-[(dimethylamino)-1H-1,2,3-triazolo-[4,5-b]pyridin-1-yl-methylene]-N-methylmethanaminium hexafluorophosphate N-oxide); hex (hexanes); MeCN (acetonitrile); MeOH (methanol); μW (microwave); MS (molecular sieves); O/N (overnight); Pd(PPh$_3$)$_4$ (tetrakis(triphenylphosphine) palladium(0)); Pd/C (palladium on carbon); Pd(OH)$_2$/C (palladium hydroxide on carbon); RT or rt (room or ambient temperature); TBS (tert-butyldimethylsilyl); TfOH (triflo-romethane sulfonic acid); THF (tetrahydrofuran); TMS (trimethylsilyl). $^1$H NMR spectra were recorded at RT with a Bruker Avanche III 600 MHz NMR spectrometer equipped with a Bruker's 5 mm PABBO probe. Chemical shifts are reported in ppm downfield from tetramethylsilane using residual solvent signals as internal reference. NMR data were processed utilizing ACD/Spectrus processor (v2016.1.1, ACD/Labs Inc.). Nomenclature for the naming of compounds, such as for Compound Examples and intermediate compounds, were performed using ACD/Name (Chemists' Version from ACD/Labs Inc.) to generate the IUPAC-style names. Naming of commercial or literature compounds utilized SciFinder, ACD/Names, and common or trivial names known to those skilled in the art.

Microwave assisted reactions were performed using an Anton Paar "Monowave 200" Microwave Synthesis Reactor with magnetron power 850 W. Unless stated otherwise the temperature was reached as fast as possible and controlled by built-in IR sensor (temperature uncertainty ±5° C.). Reaction was carried out either in 10 mL or 30 mL vials, with the default stirrer speed 600 rpm.

The LC/MS system used for monitoring the progress of reactions, assessing the purity (absorbance at 254 nm) and identity of the product consisted of Dionex ULTIMATE 3000 uHPLC module and Thermo Scientific LTQ XL mass-spectrometer with electrospray ionization and Ion-Trap type of detector (alternating positive-negative mode). Separation was performed with Thermo Scientific™ Accucore™ aQ C18 Polar Endcapped LC column (100 mm×2.1 mm; particle size 2.6 m, 80 Å). The column was maintained at 30° C. Commercial HPLC-grade methanol, acetonitrile and domestic 'millipore (Milli-Q)' water used for chromatography were modified by adding 0.1% (v/v) of formic acid. The eluent was delivered with constant flow rate of 0.4 mL/min, column was equilibrated for 5 min with the corresponding eluent prior to injection of the sample (1 μL) and one of the following separation conditions were used:

Eluent Systems:
  A—Gradient of MeOH-Water, 15% to 65% in 5 min, 65% to 95% in 2.5 min, followed by 4 min of isocratic MeOH-water 95%;
  B—Gradient of Methanol-Water, 30 to 65% in 4.75 min, then to 95% in 2.5 min, followed by 4 min of isocratic MeOH-water 95%;

C—Gradient of MeOH-Water, 10% to 45% in 5 min, 45% to 95% in 2.5 min, followed by 4 min of isocratic MeOH-water 95%; and D—Gradient of Methanol-Water, 45 to 95% in 5.25 min, followed by 5 min of isocratic MeOH-water 95%.

Compound 1

Synthesis of 1-(3-hydroxypropyl)-1,4-dihydroquinoxaline-2,3-dione, 1

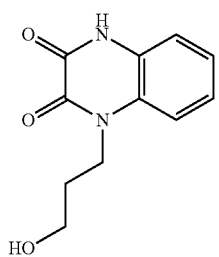

Compound 1 was synthesized as in Scheme 6.

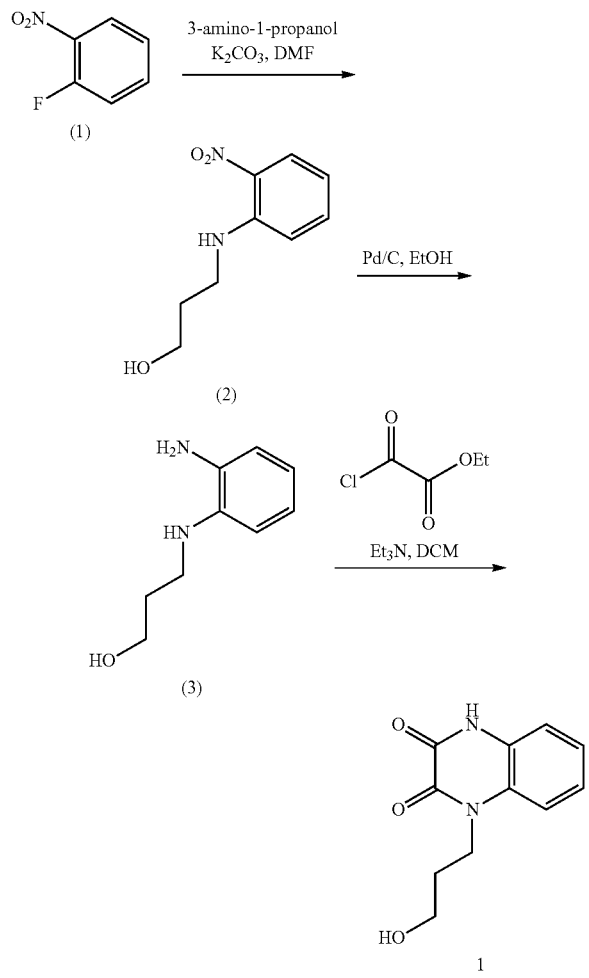

Preparation of 3-(2-nitroanilino)propan-1-ol, (2). To a solution of 1-fluoro-2-nitrobenzene (1) (60.0 g, 430 mmol) in DMF (200 mL) was added K$_2$CO$_3$ (178.0 g, 1.30 mol), and after cooling in an ice bath 3-amino-1-propanol (48.0 g, 640 mmol) via a dropping funnel. After overnight, the reaction mixture was vacuum-filtered and the solid was washed with EtOAc (2×100 mL). The solvent was removed under reduced pressure. The crude residue was dissolved in EtOAc (500 mL). The organic solution was washed thoroughly with water (3×150 mL) and brine (200 mL). The organic phase was dried over Na$_2$SO$_4$, filtered and concentrated under reduced pressure to dryness. To the residue was added hexanes (300 mL) and after 30 mins, to break the solid into fine powder, the product was collected by vacuum filtration, which provided (2) (81.4 g, 97% yield) as an orange solid.

Preparation of 3-(2-aminoanilino)propan-1-ol, (3). To a 1 L round-bottomed flask was added (2) (20.0 g, 102.0 mmol) and MeOH (300 mL). The mixture was degassed and put under a nitrogen atmosphere. Carefully 10% Pd/C (2.2 g) was added and after degassing 3 times with nitrogen, a balloon filled with hydrogen gas was added. The balloon was refilled with hydrogen gas as needed. After stirring for 6 h, the reaction mixture was filtered through a pad of Celite®, which was washed with MeOH (200 mL). The filtrate was concentrated under reduced pressure providing (3) (16.6 g, 98% yield) as a brown sticky oil. A second batch (50 g, 254.8 mmol) was done with the same procedure, which provided (3) (41.7 g, 99% yield). The material was used in the next step with out further purification.

Preparation of 1-(3-hydroxypropyl)-1,4-dihydroquinoxaline-2,3-dione, 1. To a solution of 3-(2-aminoanilino)propan-1-ol (3) (16.6 g, 100 mmol) and Et$_3$N (71.0 mL, 510 mmol) in DCM (400 mL) cooled in an ice bath was slowly added a solution of ethyl chlorooxoacetate (16.8 mL, 150 mmol) in DCM (50 mL) via a dropping funnel. After overnight, distilled water (100 mL) was added and after stirring for 30 min the mixture was filtered. A second batch with 41.7 g (251 mmol) of 3-(2-aminoanilino)propan-1-ol (3) was done using the same procedure. The two batches were combined for purification. The solids from both batches were washed with water and air dried after which they were combined and dissolved in a mixture of DCM and MeOH (1:1, 4 L). To the solution was added activated charcoal (50 g). After filtration through a pad of Celite®, the filtrate was concentrated to a volume of about 300 mL when solid precipitated from the solution. The suspension was filtered and collected solid dried providing a brown solid (13 g). The mother liquor from the first filtration was concentrated to a volume of 400 mL placed in the fridge overnight. The resulting solid was collected by gravimetric filtration and after drying provided a brown solid (20 g). The solids (13 g and 20 g) were dissolved in DCM and MeOH. It required approximately 1 L of DCM and 1 L of MeOH to fully dissolve 13 g of product. To the resulting solution was added activated charcoal and the mixture was warmed to reflux for about 30 min. Then it was filtered carefully through a pad of Celite® while the solution was still warm. The filtrate was then concentrated until precipitation appeared. The solid (33 g) was combined from the separate recrystallizations collected and the filtrates from all previous steps were also combined, concentrated under reduced pressure and dried before being re-dissolved in DCM (1.2 L) and MeOH (1.2 L). To the resulting solution was added K$_2$CO$_3$ (76.2 g, 551 mmol) and after overnight the salts were filtered through a pad of Celite® and the filtrate was absorbed to silica gel (200 g). The silica gel was dried completely under the vacuum. The silica gel with the crude product was loaded on a silica gel column and the product eluted with a gradient of MeOH/CHCl$_3$, 5 to 20%. The pure fractions were combined and treated with activated charcoal, filtered through a pad of Celite® and concentrated to a volume when solid appeared. The suspension was filtered providing an off white solid (11 g). The purified solids (33 g and 11 g) were combined and Milli-Q water (300 mL) was added. The suspension was heated to reflux for 2 h. The water was removed under reduced pressure and dried completely, which provided 1 (43.7 g, 57% yield) as a white solid.

$^1$H NMR (600 MHz, DMSO-d$_6$) δ 12.03 (br s, 1H), 7.48-7.33 (m, 1H), 7.26-7.04 (m, 3H), 4.66 (t, J=5.1 Hz, 1H), 4.27-4.07 (m, 2H), 3.52 (q, J=5.6 Hz, 2H), 1.83-1.72 (m, 2H). LC/MS: Eluent system C (retention time: 4.35 min); ESI-MS 221 [M+H]$^+$.

Compound 2

Synthesis of 1-(3-methoxypropyl)-4-methyl-1,4-dihydroquinoxaline-2,3-dione, 2

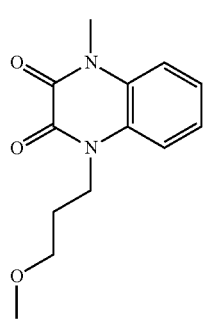

2

Compound 2 was synthesized as in Scheme 7.

Scheme 7

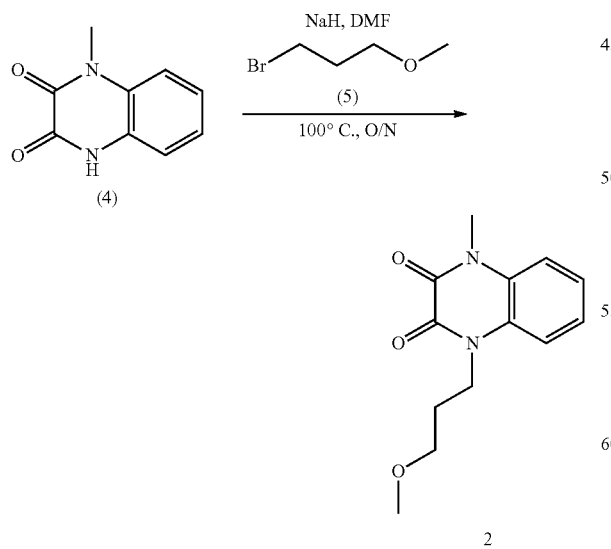

Preparation of 1-(3-methoxypropyl)-4-methyl-1,4-dihydroquinoxaline-2,3-dione, 2. To a solution of 1-methyl-1,4-dihydroquinoxaline-2,3-dione (4) (100 mg, 0.57 mmol) in DMF (5 mL) was added NaH (114 mg, 2.85 mmol, 60% in oil). After 15 min, to the mixture was added 1-bromo-3-methoxypropane (5) (0.19 mL, 2.85 mmol). The mixture was warmed in an oil bath at 100° C. After overnight, the volatiles were removed under reduced pressure. The resulting mixture was dissolved in DCM (10 mL), silica gel (5 g) was added and the solvent was removed under reduced pressure. The resulting dried silica gel with mixture absorbed was loaded on a silica gel column and the compound was eluted with a gradient of MeOH/CHCl$_3$, 0 to 5%, which generated 2 (22 mg, 16% yield) as a pale pink solid.

$^1$H NMR (600 MHz, DMSO-d$_6$) δ 7.53-7.41 (m, 2H), 7.34-7.23 (m, 2H), 4.21-4.17 (m, 2H), 3.55 (s, 3H), 3.43 (t, J=6.2 Hz, 2H), 3.25 (s, 3H), 1.94-1.79 (m, 2H). LC/MS: Eluent system A (retention time: 5.66 min); ESI-MS 249 [M+H]$^+$.

Compound 3

Synthesis of 1-(3-hydroxypropyl)-4-methyl-1,4-dihydroquinoxaline-2,3-dione, 3

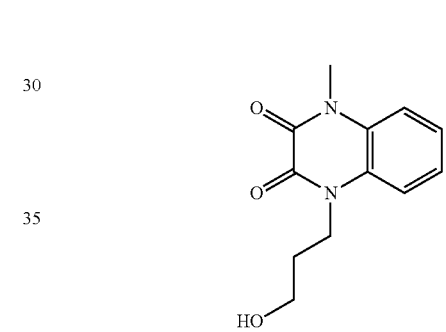

3

Compound 3 was synthesized as in Scheme 8.

Scheme 8

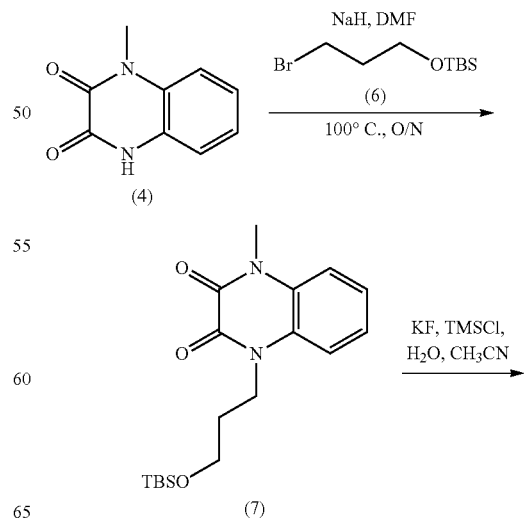

-continued

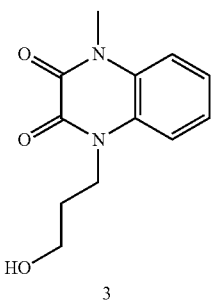

3

Compound 4

Synthesis of 1-(3-methoxypropyl)-1,4-dihydroquinoxaline-2,3-dione, 4

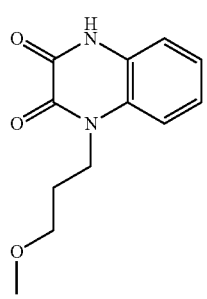

4

Compound 4 was synthesized as in Scheme 9.

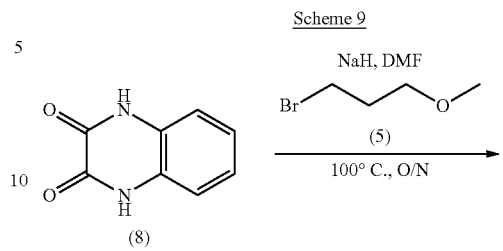

Preparation of 1-(3-{[tert-butyl(dimethyl)silyl]oxy}propyl)-4-methyl-1,4-dihydroquinoxaline-2,3-dione (7). To a solution of 1-methyl-1,4-dihydroquinoxaline-2,3-dione (4) (100 mg, 0.57 mmol) in DMF (5 mL) was added NaH (114 mg, 2.85 mmol, 60% in oil). After stirring for 15 min, to the mixture was added 3-(tert-butyldimethylsilyloxy)propyl bromide (6) (0.26 mL, 1.14 mmol). The mixture was heated in an oil bath at 100° C. After overnight, the solvent was removed under reduced pressure. The resulting material was dissolved in DCM (10 mL), silica gel (5 g) was added and the solvent was removed under reduced pressure. The resulting dried silica gel with absorbed mixture was loaded on a silica gel column and the compound was eluted with a gradient of MeOH/CHCl$_3$, 0 to 5%, which generated (7) (128 mg, 64% yield) as a white solid.

Preparation of 1-(3-hydroxypropyl)-4-methyl-1,4-dihydroquinoxaline-2,3-dione, 3. To a solution of 1-(3-{[tert-butyl(dimethyl)silyl]oxy}propyl)-4-methyl-1,4-dihydroquinoxaline-2,3-dione (7) (128 mg, 0.37 mmol) in CH$_3$CN (5 mL) was added KF (22 mg 0.37 mmol), followed by TMSCl (0.047 mL, 0.37 mmol) and 1 drop of water. After 1 h, the reaction mixture was quenched with a saturated NaHCO$_3$ aqueous solution. The mixture was extracted with DCM (3×15 mL). The combined organic phase was washed with brine (15 mL), dried over Na$_2$SO$_4$, filtered and concentrated under reduced pressure. The product was purified by column chromatography on silica gel with a gradient of MeOH/EtOAc, 0 to 10%, which generated 3 as a white solid (61 mg, 70% yield).

$^1$H NMR (600 MHz, DMSO-d$_6$) δ 7.54-7.47 (m, 1H), 7.46-7.41 (m, 1H), 7.38-7.19 (m, 2H), 4.68 (t, J=5.1 Hz, 1H), 4.23-4.17 (m, 2H), 3.55 (s, 3H), 3.54-3.51 (m, 2H), 1.83-1.75 (m, 2H). LC/MS: Eluent system A (retention time: 4.05 min); ESI-MS 235 [M+H]$^+$.

Preparation of 1-(3-methoxypropyl)-1,4-dihydroquinoxaline-2,3-dione, 4. To a solution of 1,4-dihydroquinoxaline-2,3-dione (8) (1.0 g, 6.2 mmol) in DMF (5 mL) was added NaH (74 mg, 1.86 mmol, 60% in oil). After 30 min, to the mixture was added 1-bromo-3-methoxypropane (5) (0.07 mL, 0.62 mmol). The resulting mixture was warmed to 100° C. in an oil bath. After overnight, the oil bath was removed and after cooling to ambient temperature methanol was slowly added. The volatiles were removed under reduced pressure. The resulting material was dissolved in DCM/MeOH (1:1, 20 mL), silica gel (10 g) was added and the solvent was removed under reduced pressure. The resulting dried silica gel with material absorbed was loaded on a silica gel column and the compound was eluted with a gradient of MeOH/CHCl$_3$, 0 to 20%, which generated 4 (34 mg, 23% yield) as a white solid.

$^1$H NMR (600 MHz, DMSO-d$_6$) δ 12.03 (br s, 1H), 7.44-7.34 (m, 1H), 7.26-7.09 (m, 3H), 4.21-4.10 (m, 2H), 3.42 (t, J=6.2 Hz, 2H), 3.25 (s, 3H), 1.92-1.81 (m, 2H). LC/MS: Eluent system A (retention time: 6.30 min); ESI-MS 235 [M+H]$^+$.

Compound 5

Synthesis of 1-(3-phenoxypropyl)-1,4-dihydroquinoxaline-2,3-dione, 5

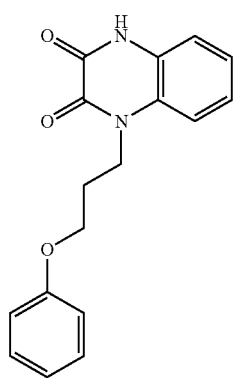

Compound 5 was synthesized as in Scheme 10.

Scheme 10

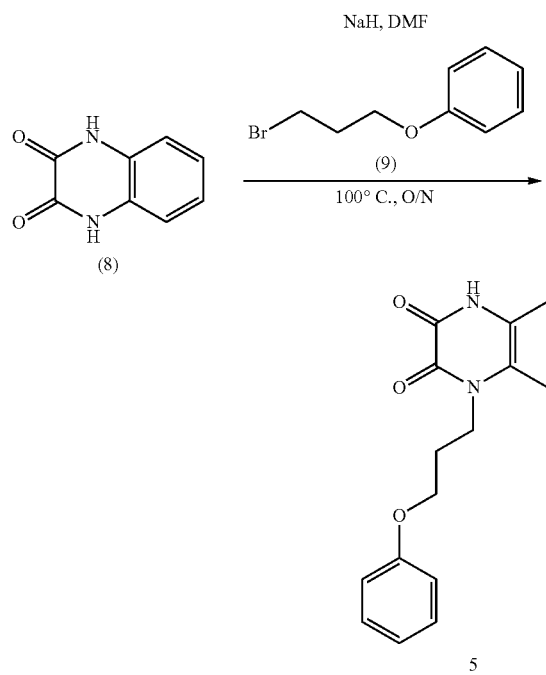

Preparation of 1-(3-phenoxypropyl)-1,4-dihydroquinoxaline-2,3-dione 5. To a solution of 1,4-dihydroquinoxaline-2,3-dione (8) (1.0 g, 6.2 mmol) in DMF (5 mL) was added NaH (74 mg, 1.86 mmol, 60% in oil). After 30 min, to the mixture was added 3-phenoxypropyl bromide (9) (0.10 mL, 0.62 mmol). The resulting mixture was warmed to 100° C. in an oil bath. After overnight, the oil bath was removed and after cooling to ambient temperature methanol was slowly added. The volatiles were removed under reduced pressure. The resulting material was dissolved in DCM/MeOH (1:1, 20 mL), silica gel (5 g) was added and the solvent was removed under reduced pressure. The resulting dried silica gel with material absorbed was loaded on a silica gel column and the compound was eluted with a gradient of MeOH/CHCl$_3$, 0 to 10%, which generated 5 (103 mg, 56% yield) as a white solid.

$^1$H NMR (600 MHz, DMSO-d$_6$) δ 12.04 (brs, 1H), 7.46-7.41 (m, 1H), 7.32-7.27 (m, 2H), 7.23-7.14 (m, 3H), 6.97-6.91 (m, 3H), 4.32-4.25 (m, 2H), 4.09 (t, J=6.2 Hz, 2H), 2.12-2.05 (m, 2H). LC/MS: Eluent system A (retention time: 7.85 min); ESI-MS 297 [M+H]$^+$.

Compound 6

Synthesis of 3-oxo-3-(3-oxo-3,4-dihydroquinoxalin-1(2H)-yl)propyl acetate, 6

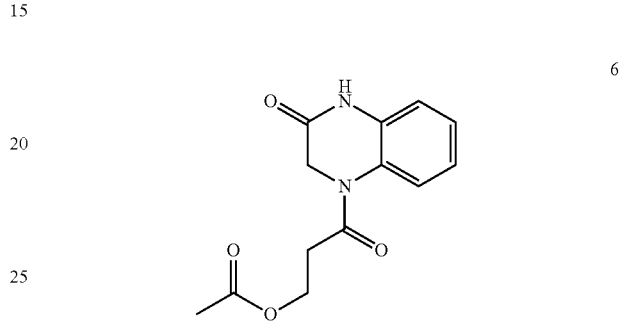

Compound 6 was synthesized as in Scheme 11.

Scheme 11

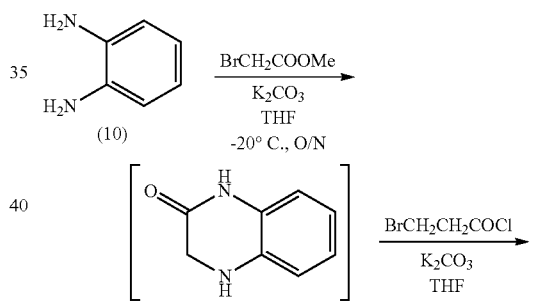

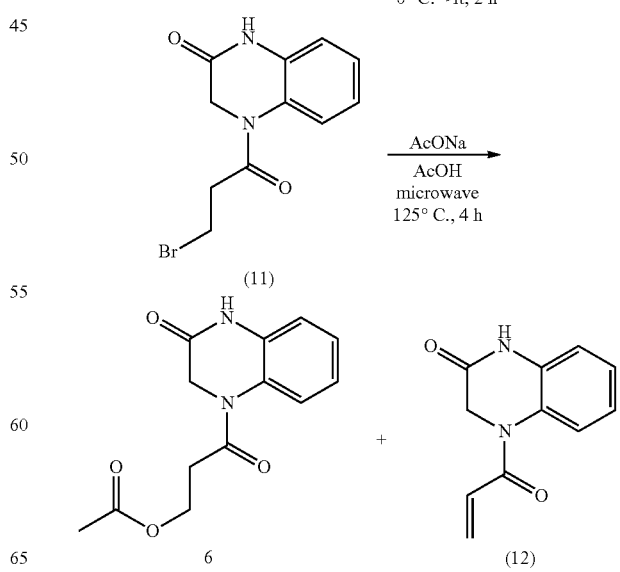

Preparation of 4-(3-bromopropanoyl)-3,4-dihydroquinoxalin-2(1H)-one, (11). A solution of methyl bromoacetate (15 g, 0.098 mol) in THF (30 mL) was cooled in a −78° C. bath and to this was added a precooled to the same temperature solution of o-phenylenediamine (10) (10.0 g, 0.0925 mol) in THF (50 mL), containing potassium carbonate (15.0 g, 0.108 mol). After thoroughly stirring the mixture, it was left at −20° C. in the freezer. After overnight, the mixture was warmed to ambient temperature. After 1 h, the reaction flask was placed in the ice-salt bath and once internal temperature reached −5° C. the ice-cold solution of 3-bromopropanoyl chloride (17.1 g, 0.099 mol) in THF (15 mL) was added slowly so that the temperature of the reaction mixture didn't raise above 10° C. After 30 minutes, the ice-salt bath was removed and after one hour at room temperature the mixture was partitioned between ethyl acetate (200 mL) and water (100 mL). The organic layer was dried over sodium sulfate, filtered, and concentrated under reduced pressure. The product was purified by column chromatography on silica gel (eluted with hexane-DCM-ethyl acetate 2:1:0-1:1:2), which provided (11) (9.4 g, 36% over two steps) as a brownish powder.

Preparation of 3-oxo-3-(3-oxo-3,4-dihydroquinoxalin-1(2H)-yl)propyl acetate, 6. A solution of 4-(3-bromopropanoyl)-3,4-dihydroquinoxalin-2(1H)-one (11) (660 mg, 2.33 mmol), sodium acetate (300 mg, 3.66 mmol) in glacial acetic acid (8 mL) in a 30 mL microwave vial was heated under microwave irradiation for 4 hours with the temperature set at 125° C. Another portion of sodium acetate (300 mg, 3.66 mmol) was then added and the mixture was heated for additional 4 hours at 125° C. The mixture was concentrated under reduced pressure, partitioned between water and chloroform and the organic layer was separated and concentrated. A DCM solution of the resulting residue was loaded on silica gel. Purification was accomplished by silica gel column chromatography (eluted with hexanes-ethyl acetate 35%→70%) provided two products: 4-acryloyl-3,4-dihydroquinoxalin-2(1H)-one (12) (85 mg, 18% yield) as a by-product and the target 6 (150 mg, 25% yield) as a white powder.

$^1$H NMR (600 MHz, DMSO-d$_6$) δ 10.71 (s, 1H), 7.49 (br s, 1H), 7.22 (br s, 1H), 7.08-7.01 (m, 2H), 4.35 (s, 2H), 4.26-4.18 (m, 2H), 2.88 (br s, 2H), 1.95 (s, 3H). LC/MS: Eluent system C (retention time: 6.17 min); ESI-MS 263 [M+H]$^+$ and 261 [M−H]$^-$.

Compound 7

Synthesis of 4-(3-((2-hydroxyethyl)amino)propanoyl)-3,4-dihydroquinoxalin-2(1H)-one, 7

Compound 7 was synthesized as in Scheme 12.

Scheme 12

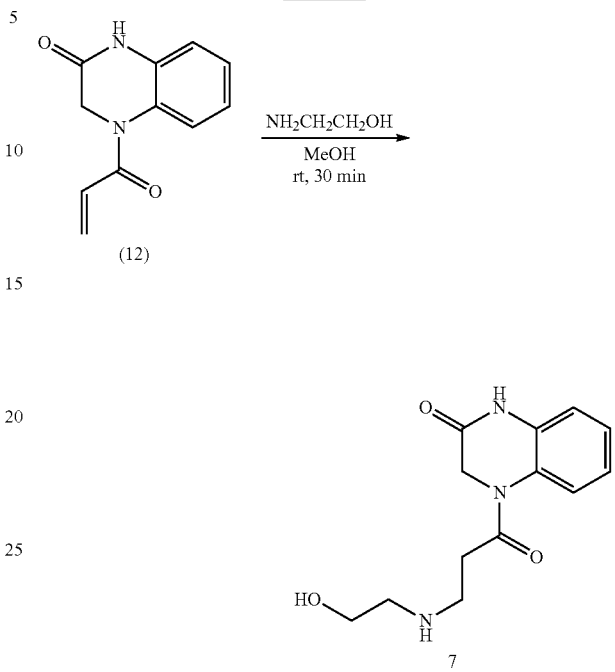

Preparation of 4-(3-((2-hydroxyethyl)amino)propanoyl)-3,4-dihydroquinoxalin-2(1H)-one, 7. To a solution of 4-acryloyl-3,4-dihydroquinoxalin-2(1H)-one (12) (40 mg, 0.2 mmol) in methanol (5 mL) was added ethanolamine (0.50 g, 8.2 mmol). After 30 min, the mixture was concentrated under pressure and the product purified by silica gel column chromatography (eluted with ethyl acetate-methanol 2%→50%), which after trituration with ether provided 7 (16 mg, 30% yield) as a white powder.

$^1$H NMR (600 MHz, DMSO-d6) δ 10.68 (br s, 1H), 7.50 (br s, 1H), 7.23-7.17 (m, 1H), 7.08-7.00 (m, 2H), 4.42 (s, 1H), 4.34 (s, 2H), 2.77-2.71 (m, 2H), 2.67-2.62 (m, 2H), 2.52-2.44 (m, 4H). LC/MS: Eluent system C (retention time: 1.16 min); ESI-MS 264 [M+H]$^+$ and 262 [M−H]$^-$.

Compound 8

Synthesis of 4-(3-(dimethylamino)propanoyl)-3,4-dihydroquinoxalin-2(1H)-one, 8

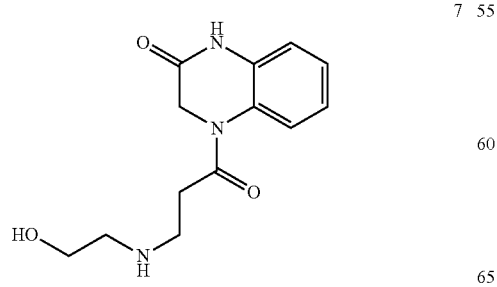

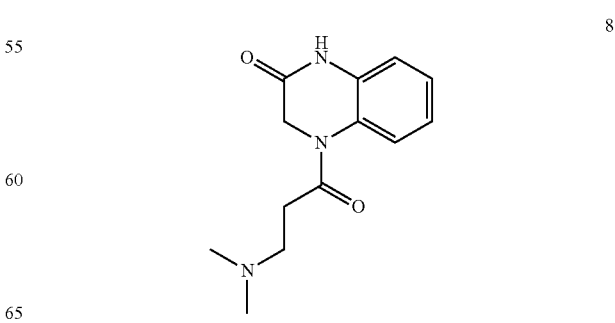

Compound 8 was synthesized as in Scheme 13.

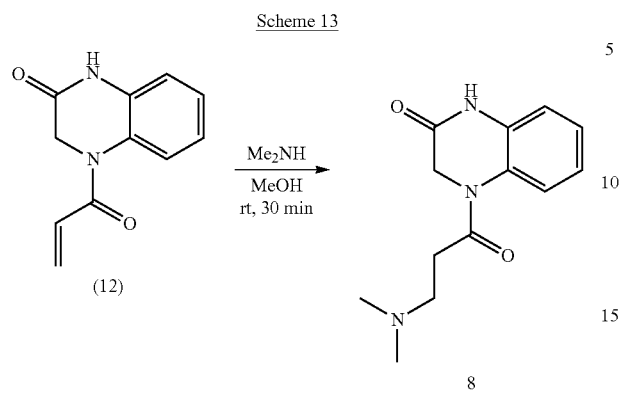

Preparation of 4-(3-(dimethylamino)propanoyl)-3,4-dihydroquinoxalin-2(1H)-one, 8. To a solution of 4-acryloyl-3,4-dihydroquinoxalin-2(1H)-one (12) (40 mg, 0.2 mmol) in methanol (5 mL) was added a 2N solution of dimethylamine in THF (2 mL, 4 mmol). After 30 min, the mixture was concentrated under reduced pressure and the product was purified by silica gel column chromatography (eluted with ethyl acetate-methanol 2%→50%), which produced 8 (30 mg, 61% yield) as a yellow-brown glass like sticky liquid.

$^1$H NMR (600 MHz, DMSO-d6) δ 10.60 (br s, 1H), 7.65-7.36 (m, 1H), 7.28-6.97 (m, 3H), 4.34 (s, 2H), 2.77-2.40 (m, 4H), 2.03 (br s, 6H). LC/MS: Eluent system C (retention time: 1.09 min); ESI-MS 248 [M+H]$^+$.

Compound 9

Synthesis of 1-(2-hydroxyethyl)-1,4-dihydroquinoxaline-2,3-dione, 9

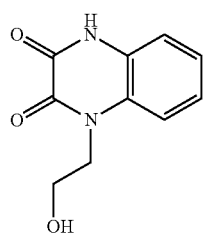

Compound 9 was synthesized as in Scheme 14.

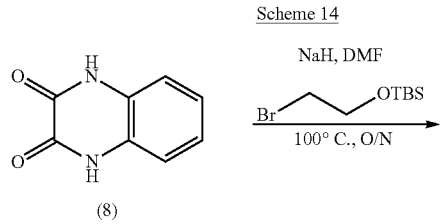

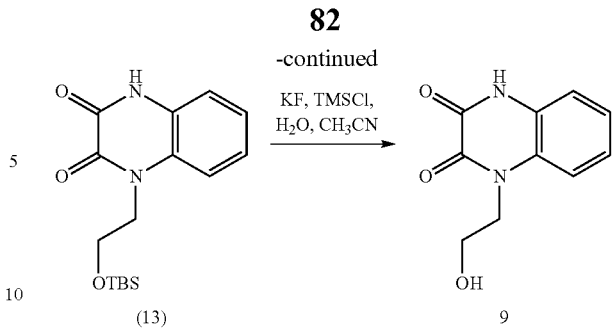

Preparation of 1-(2-{[tert-butyl(dimethyl)silyl]oxy}ethyl)-1,4-dihydroquinoxaline-2,3-dione (13). To a solution of 1,4-dihydroquinoxaline-2,3-dione (8) (1.0 g, 6.2 mmol) in DMF (10 mL) was added NaH (248 mg, 6.2 mmol, 60% in oil). After 30 min, to the mixture was added 2-(tert-butyldimethylsilyloxy)ethyl bromide (0.13 mL, 0.62 mmol). The resulting mixture was heated in an oil bath at 100° C. After overnight, the solvent was removed under reduced pressure. The crude material was dissolved in DCM/MeOH (1:1, 20 mL), silica gel (10 g) was added and the volatiles were removed under reduced pressure. The resulting dried silica gel with the mixture absorbed was loaded on silica gel column and the product was eluted with a gradient of MeOH/CHCl$_3$, 0 to 10%, which generated (13) (122 mg, 61% yield) as a white solid.

Preparation of 1-(2-hydroxyethyl)-1,4-dihydroquinoxaline-2,3-dione, 9. To a solution of 1-(2-{[tert-butyl(dimethyl)silyl]oxy}ethyl)-1,4-dihydroquinoxaline-2,3-dione (13) (122 mg, 0.38 mmol) in CH$_3$CN (10 mL) was added KF (22 mg, 0.38 mmol), followed by TMSCl (0.048 mL, 0.38 mmol) and 1 drop of water. After 1 h, the reaction mixture was quenched with a saturated NaHCO$_3$ aqueous solution. The resulting mixture was extracted with DCM (3×15 mL). The combined organic phase was washed with brine (15 mL), dried over Na$_2$SO$_4$, filtered and concentrated under reduced pressure. The product was purified by column chromatography on silica gel with a gradient of MeOH/CHCl$_3$, 0 to 20%, which generated 9 as a white solid (65 mg, 83% yield).

$^1$H NMR (600 MHz, DMSO-d$_6$) δ 12.14 (br s, 1H), 7.62-7.52 (m, 1H), 7.36-7.21 (m, 3H), 4.99 (t, J=6.0 Hz, 1H), 4.32 (t, J=6.2 Hz, 2H), 3.78 (q, J=6.0 Hz, 2H). LC/MS: Eluent system C (retention time: 3.11 min); ESI-MS 207 [M+H]$^+$.

Compound 10

Synthesis of 4-(3-hydroxypropanoyl)-3,4-dihydroquinoxalin-2(1H)-one, 10

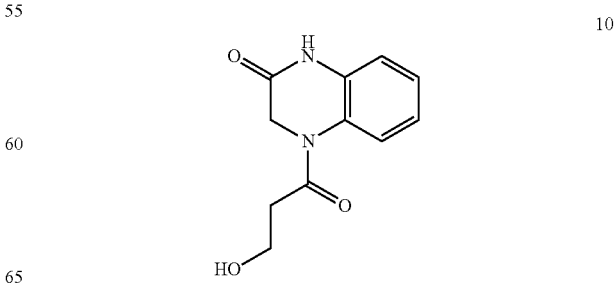

Compound 10 was synthesized as in Scheme 15

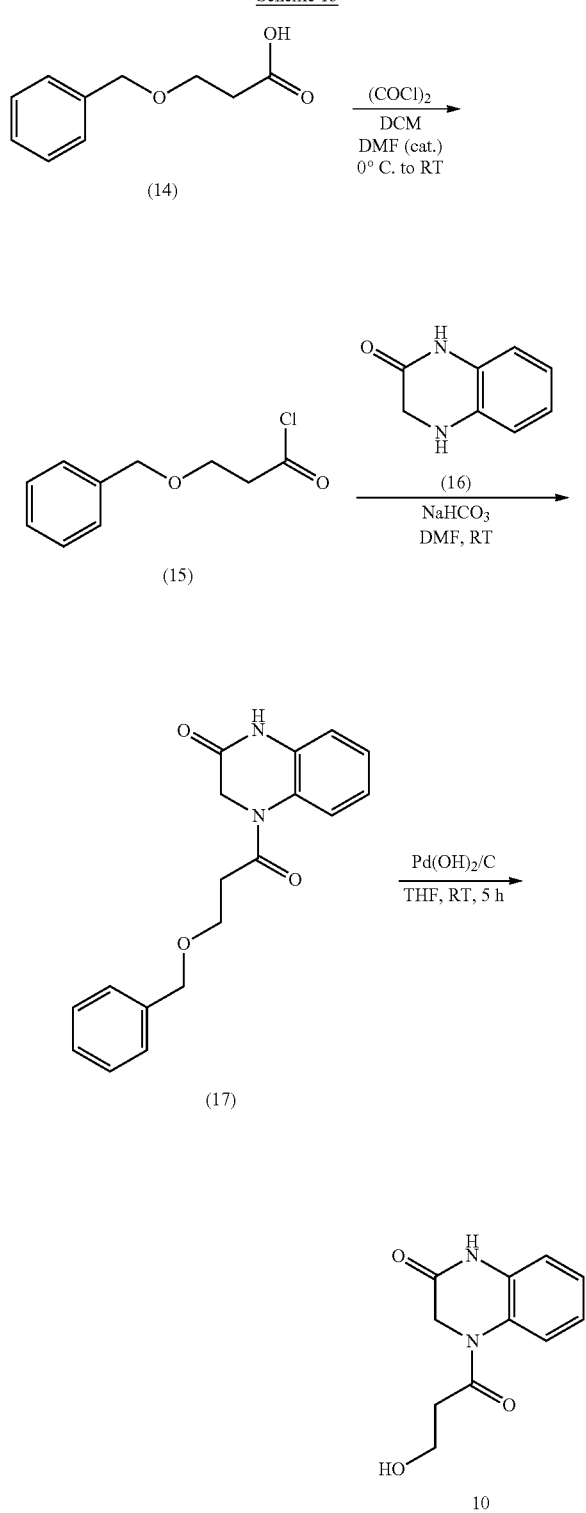

Preparation of 3-(benzyloxy)propanoyl chloride, (15). An oven-dried, 1.0 L round-bottomed flask equipped with rubber septum containing thermometer, nitrogen inlet and outlet, cooling bath, and magnetic stirrer, was charged with 3-(benzyloxy)propanoic acid (14) (27.5 g, 0.153 mol) and anhydrous DCM (500 mL). The solution was cooled to 0-5° C. (internal temperature) using an ice-water bath. Oxalyl chloride (25.8 mL, 0.305 mol) was then added dropwise over 10 min under nitrogen atmosphere. After 15 min at 0-5° C., anhydrous DMF (0.75 mL) was added dropwise over 15 min. After 15 min, the ice bath was removed and the reaction warmed to room temperature. After 1 h at ambient temperature, the mixture was concentrated under reduced pressure using a 30° C. water bath, it was then co-evaporated with anhydrous DCM (3×100 mL), and dried under reduced pressure using a 35° C. water bath for 1.0 h, which generated (15) (30.32 g, quantitative yield) as a pinkish-orange color solid. This was used in the next step without further purification.

Preparation of 4-[3-(benzyloxy)propanoyl]-3,4-dihydroquinoxalin-2(1H)-one, (17). To 3-(benzyloxy)propanoyl chloride (15) (30.32 g, 0.153 mol) in a 1.0 L round-bottomed flask, was added solid 3,4-dihydroquinoxalin-2(1H)-one (16) (20.35 g, 0.137 mol) and anhydrous DMF (300 mL). After 15 min, anhydrous NaHCO$_3$ (15.4 g, 0.183 mol) was added in one portion. After overnight, a saturated aqueous NaHCO$_3$ solution (100 mL) was added and saturated brine solution (500 mL), the resulting mixture was extracted with CHCl$_3$ (3×750 mL). The combined organics were dried over anhydrous Mg$_2$SO$_4$, filtered, and concentrated under reduced pressure using a 50° C. water bath. The resulting residue was dissolved in CHCl$_3$ (200 mL) and adsorbed on silica gel (50 g). The product was then purified by Biotage® (330 g Silicycle column) eluting with a gradient of 0% to 6%, MeOH:CHCl$_3$. The resulting tan color solid was dissolved in CHCl$_3$:MeOH (90:10, 500 mL) and activated charcoal (30 g) was added. After 1 h, the charcoal was removed by vacuum filtration through a bed of Celite®, and the bed was washed with CHCl$_3$:MeOH (90:10, 3×200 mL). The combined filtrates were concentrated under reduced pressure that afforded (17) as an off white solid (37.6 g, 79% yield).

Preparation of 4-(3-hydroxypropanoyl)-3,4-dihydroquinoxalin-2(1H)-one, 10. To a solution of 4-[3-(benzyloxy)propanoyl]-3,4-dihydroquinoxalin-2(1H)-one (17) (32.6 g, 0.105 moles) in THF (300.0 mL) was added 10% Pd(OH)$_2$/C (3.26 g). Two balloons were filled with hydrogen gas and affixed onto the round-bottomed flask. After 5 h, the resulting mixture was filtered using vacuum filtration through a bed of Celite®, and the bed was washed thoroughly with CHCl$_3$:MeOH (80:20, 5×250 mL). The combined filtrates were concentrated under reduced pressure. Similarly, another batch of hydrogenation was carried with 5.0 g (16.11 mmol) of (17) and 0.5 g of 10% Pd(OH)$_2$/C in 50 mL THF. The crude from the two batches were combined and adsorbed on silica gel (50 g) using CHCl$_3$:MeOH (80:20, 200 mL). The product was purified by Biotage® (330 g silicycle HP column) eluting with a gradient of 0% to 20%, MeOH:CHCl$_3$. To the resulting solid was added 300 mL water and the resulting mixture was refluxed for 1 h and then after cooling to ambient temperature was concentrated under reduced pressure with a water bath at 50° C., which afforded 10 as an off-white solid (23.6 g, 88% yield).

$^1$H NMR (600 MHz, DMSO-d$_6$) δ 10.69 (s, 1H), 7.53 (br s, 1H), 7.24-7.18 (m, 1H), 7.06-7.01 (m, 2H), 4.64 (t, J=5.2 Hz, 1H), 4.35 (s, 2H), 3.67 (q, J=6.0 Hz, 2H), 2.66 (br. t, J=5.8 Hz, 2H). LC/MS: Eluent system C (retention time: 4.17 min); ESI-MS: 221 [M+H]$^+$.

Compounds 11 and 12

Synthesis of 1-(3-hydroxypropyl)-4-methoxy-1,3-dihydro-2H-1,5-benzodiazepin-2-one, 11 and 1-(3-hydroxypropyl)-1H-1,5-benzodiazepine-2,4(3H,5H)-dione, 12

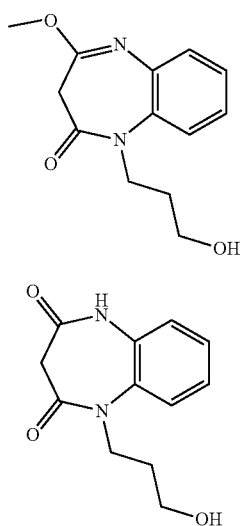

Compounds 11 and 12 were synthesized as in Scheme 16.

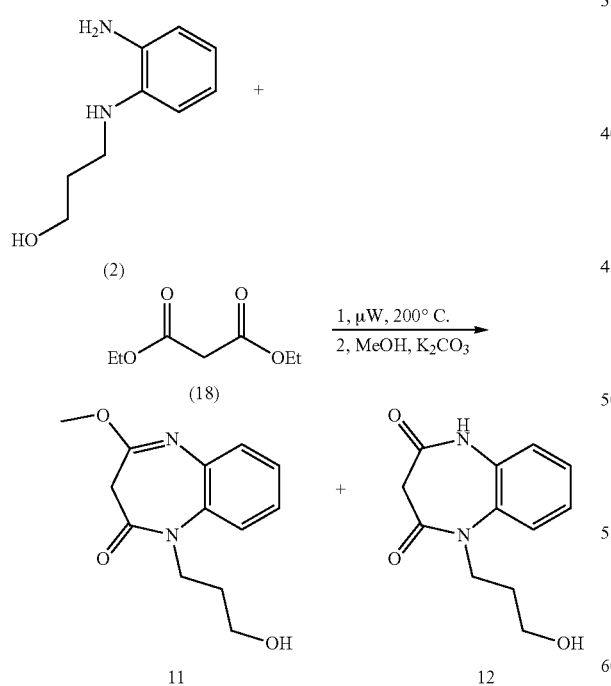

Preparation of 1-(3-hydroxypropyl)-4-methoxy-1,3-dihydro-2H-1,5-benzodiazepin-2-one, 11 and 1-(3-hydroxypropyl)-1H-1,5-benzodiazepine-2,4(3H,5H)-dione, 12. A mixture of 3-(2-aminoanilino)propan-1-ol (2), (100 mg, 0.60 mmol) and diethyl malonate (18) (1.0 mL, 6.62 mmol) were put in a dry 10 mL microwave vial and the vial was positioned in a microwave reactor that was then set 200° C. After 30 min, the reaction mixture was cooled to ambient temperature and methanol (3 mL) and $K_2CO_3$ (300 mg, 2.17 mmol) were added. After overnight, the mixture was vacuum filtered and the solid was washed with $CHCl_3$: MeOH (9:1, 3×10 mL). The combined filtrates were concentrated under reduced pressure. The mixture was adsorbed on silica gel (5 g) using $CHCl_3$ (5 mL) and purified by column purification on silica gel (Biotage®, 12 g silicycle column, eluted with chloroform-methanol: 0% to 2%), which afforded 11 as an off-white solid (33.9 mg, 23% yield).

$^1$H NMR (600 MHz, DMSO-$d_6$) δ 7.57 (d, J=7.9 Hz, 1H), 7.55 (d, J=7.9 Hz, 1H) 7.24-7.22 (m, 1H), 7.19-7.17 (m, 1H), 4.71 (t, J=4.9 Hz, 1H), 4.26 (t, J=7.2 Hz, 2H), 4.13 (s, 2H), 3.67 (s, 3H), 3.40-3.38 (m, 2H), 1.92-1.81 (m, 2H). LC/MS: Eluent system C (retention time: 2.75 min); ESI-MS: 249 [M+H]$^+$.

Further elution of the column with a gradient of 2% to 10% methanol in chloroform produced 12, which was triturated with EtOAc and hexanes to afford pure 12 as a white solid (17.8 mg, 13% yield).

$^1$H NMR (600 MHz, DMSO-$d_6$) δ 10.39 (s, 1H), 7.58-7.52 (m, 1H), 7.30-7.23 (m, 2H), 7.21-7.15 (m, 1H), 4.44 (t, J=5.1 Hz, 1H), 4.27-4.17 (m, 1H), 3.76-3.64 (m, 1H), 3.40-3.36 (m, 1H), 3.31-3.21 (m, 2H), 3.01-2.88 (m, 1H), 1.64-1.43 (m, 2H). LC/MS: Eluent system C (retention time: 4.40 min); ESI-MS: 235 [M+H]$^+$.

Compound 13

Synthesis of 1-(3-hydroxypropyl)-6-(pyridin-3-yl)-1,4-dihydroquinoxaline-2,3-dione, 13

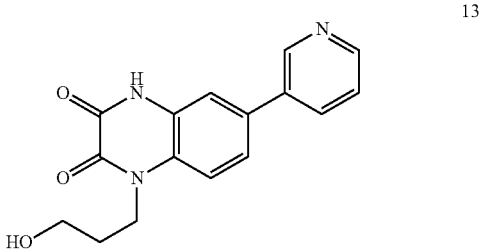 [SMILES: O=c1[nH]c2cc(-c3cccnc3)ccc2n(CCCO)c1=O]

Compound 13 was synthesized as in Scheme 17.

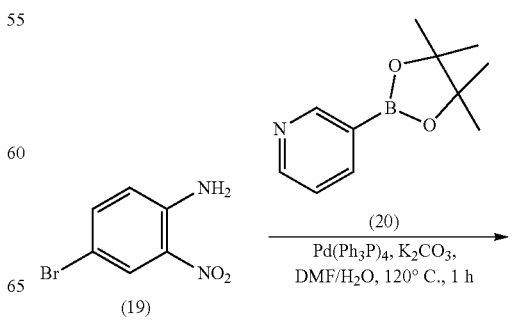

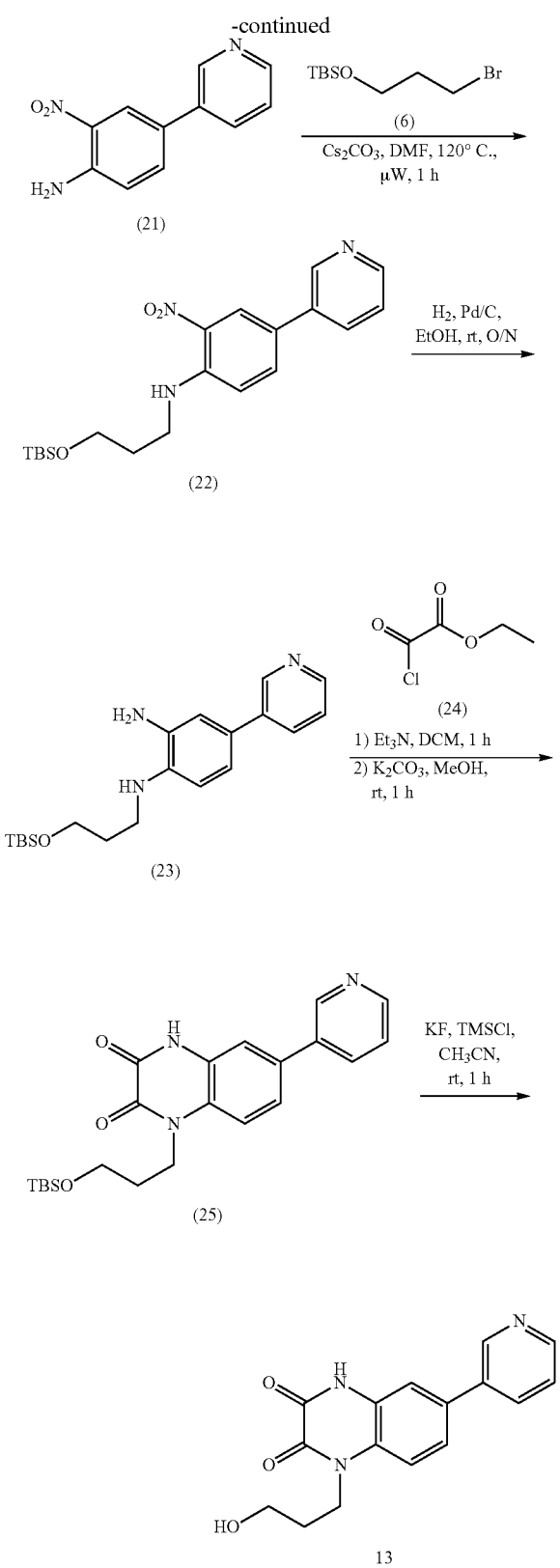

Preparation of 2-nitro-4-(pyridin-3-yl)aniline, (21). A mixture of 4-bromo-2-nitroaniline (19) (400 mg, 1.84 mmol), 4,4,5,5-tetramethyl-2-phenyl-1,3,2-dioxaborolane (20) (450 mg, 2.19 mmol), water (1 mL), $K_2CO_3$ (304.1 mg, 2.2 mmol) and DMF (10 mL) was purged with $N_2$ for 5 min. To this mixture was added $Pd(PPh_3)_4$ (106.3 mg, 0.092 mmol) and the resulting mixture was heated in an oil bath at 120° C. After 1 h, the mixture was concentrated under reduced pressure and the residue was then mixed with chloroform (50 mL), filtered and concentrated. The product was purified by column chromatography on silica gel (eluted with hexanes-ethyl acetate 0-50%), which generated (21) (310 mg, 78% yield) as a gum. Preparation of N-(3-{[tert-butyl(dimethyl)silyl]oxy}propyl)-2-nitro-4-(pyridin-3-yl) aniline, (22). A mixture of 2-nitro-4-(pyridin-3-yl)aniline (21) (200.0 mg, 0.93 mmol), (3-bromopropoxy)(tert-butyl) dimethylsilane (6) (471.0 mg, 1.86 mmol), $Cs_2CO_3$ (303.0 mg, 0.93 mmol) in DMF (5 mL) was irradiated in a microwave reactor for 1 h at 120° C. The mixture was concentrated under reduced pressure and the product was purified by column chromatography on silica gel (eluted with 0-50% ethyl acetate in hexanes), which generated (22) (116.3 mg, 32% yield) as a gum. Preparation of $N^1$-(3-{[tert-butyl(dimethyl)silyl]oxy}propyl)-4-(pyridin-3-yl)benzene-1,2-diamine, (23). A solution of N-(3-{[tert-butyl(dimethyl)silyl]oxy}propyl)-2-nitro-4-(pyridin-3-yl)aniline (22) (116.3 mg, 0.30 mmol) in ethanol (25 mL) was purged with nitrogen for 5 min and 10% Pd/C (116.0 mg) was added. The mixture was placed under a positive hydrogen pressure from a hydrogen filled balloon. After 18 h, the mixture was filtered through a pad of Celite®, the pad was washed with ethanol (10 mL), concentrated under reduced pressure, which provided (23) (100.0 mg, 93%) as a gum. This material was used in the next step without further purification.

Preparation of 1-(3-{[tert-butyl(dimethyl)silyl]oxy}propyl)-6-(pyridin-3-yl)-1,4-dihydroquinoxaline-2,3-dione, (25). To a solution of $N^1$-(3-{[tert-butyl(dimethyl)silyl]oxy}propyl)-4-(pyridin-3-yl)benzene-1,2-diamine (23) (100.0 mg, 0.279 mmol) and triethylamine (141.6 mg, 1.39 mmol) in DCM (25 mL) cooled in an ice-bath was slowly added ethyl chloro(oxo)acetate (24) (78.5 mg, 0.56 mmol). The ice-bath was removed and the mixture warmed to ambient temperature. After 1 h, the mixture was concentrated under reduced pressure. The resulting residue was diluted with methanol (25 mL) and $K_2CO_3$ (193.5 mg, 1.40 mmol) was added. After 2 h, the resulting mixture was concentrated, mixed with chloroform (50 mL) filtered, concentrated under reduced pressure and the product was purified by silica gel column chromatography (eluted with 0 to 5% methanol in chloroform), which produced (25) (39.0 mg, 34% yield) as a gum.

Preparation of 1-(3-hydroxypropyl)-6-(pyridin-3-yl)-1,4-dihydroquinoxaline-2,3-dione, 13. To a solution of 1-(3-{[tert-butyl(dimethyl)silyl]oxy}propyl)-6-(pyridin-3-yl)-1,4-dihydroquinoxaline-2,3-dione (25) (39.0 mg, 0.095 mmol) in acetonitrile (5 mL) was added KF (5.8 mg, 0.099 mmol) followed by TMSCl (10.8 mg, 0.099 mmol). After 1 h, the mixture was concentrated under reduced pressure and the product purified by silica gel column chromatography (eluted with 0 to 5% methanol in chloroform), which produced 13 (8.0 mg, 28% yield) as a white solid.

$^1$H NMR (600 MHz, DMSO-$d_6$) δ 12.13 (s, 1H), 8.88 (br s, 1H), 8.61 (br s, 1H), 8.03 (d, J=8.1 Hz, 1H), 7.59-7.52 (m, 3H), 7.47 (d, J=2.1 Hz, 1H), 4.69 (br s, 1H), 4.23-4.15 (m, 2H), 3.58-3.51 (m, 2H), 1.85-1.78 (m, 2H). LC/MS: Eluent system C (retention time: 3.85 min); ESI-MS 298 [M+H]$^+$.

Compound 14

Synthesis of N,N-dimethyl-3-oxo-3-(3-oxo-3,4-dihydroquinoxalin-1(2H)-yl)propanamide, 14

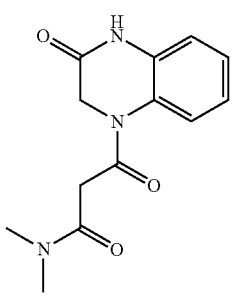

14

Compound 14 was synthesized as in Scheme 18.

Scheme 18

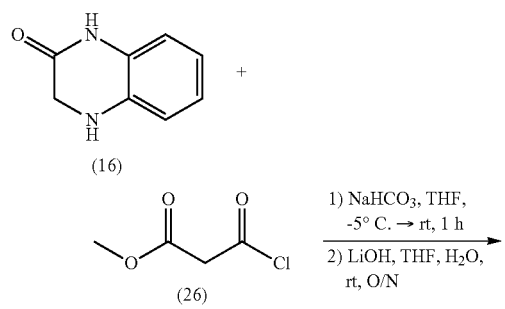

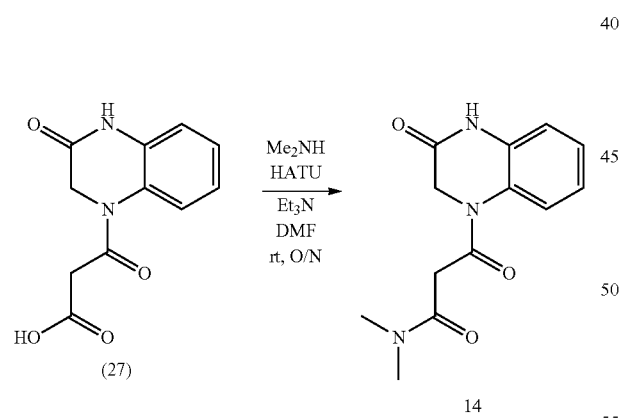

Preparation of 3-oxo-3-(3-oxo-3,4-dihydroquinoxalin-1(2H)-yl)propanoic acid, (27). To a solution of 3,4-dihydro-1H-quinoxalin-2-one (16) (100 mg, 0.67 mmol) in THF at −5° C. was added sodium bicarbonate (100 mg, 1.2 mmol) followed by methyl malonyl chloride (26) (100 mg, 0.73 mmol), after which the ice-salt bath was removed. After 1 h, the mixture was concentrated under reduced pressure and the resulting residue was partitioned between ethyl acetate (3×15 mL) and 1M HCl solution (10 mL). The organic layer was dried over sodium sulfate, filtered and concentrated under reduced pressure which generated a clear oil (250 mg). The oil was dissolved in THF (15 mL) and treated with a 1M solution of LiOH in water (8 mL). After overnight, the mixture was washed with chloroform, then the pH of aqueous layer was adjusted to 1.8 (pH meter) with a 1M solution of sodium bisulfate and the product was extracted with ethyl acetate-tert-butanol solution (8:1). The ethyl acetate-tert-butanol layer was dried over sodium sulfate, filtered and concentrated under reduced pressure, which provided (27) (196 mg) as a brown oil. This material was used in the next step without further purification.

Preparation of N,N-dimethyl-3-oxo-3-(3-oxo-3,4-dihydroquinoxalin-1(2H)-yl)propanamide 14. In a sealable tube, a DMF (5 mL) solution of 3-oxo-3-(3-oxo-3,4-dihydroquinoxalin-1(2H)-yl)propanoic acid (27) (50 mg, approximately ¼ of the obtained amount) was mixed with HATU (190 mg, 0.50 mmol) and a 2M THF solution of dimethylamine (2.0 mL, 4.0 mmol) and the tube was sealed. After overnight, the mixture was concentrated under reduced pressure and the product was purified by silica gel column chromatography (eluent with chloroform-methanol 0%→9%), which provided 14 (11.1 mg, 14% yield over 3 steps) as a pink solid.

$^1$H NMR (600 MHz, DMSO-d6) δ 10.70 (br s, 1H), 7.50 (br s, 1H), 7.22 (br s, 1H), 7.07-6.97 (m, 2H), 4.42-4.15 (m, 2H), 3.87-3.63 (m, 2H), 2.89 (br s, 3H), 2.75 (br s, 3H). LC/MS: Eluent system C (retention time: 4.55 min); ESI-MS 262 [M+H]$^+$ and 260 [M−H]$^-$.

Compound 15

Synthesis of 4-(3-hydroxypropanoyl)-4,5-dihydro-1H-benzo[e][1,4]diazepin-2(3H)-one, 15

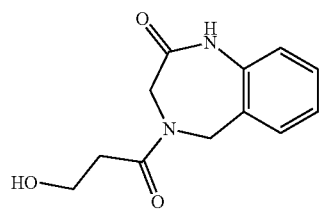

15

Compound 15 was synthesized as in Scheme 19.

Scheme 19

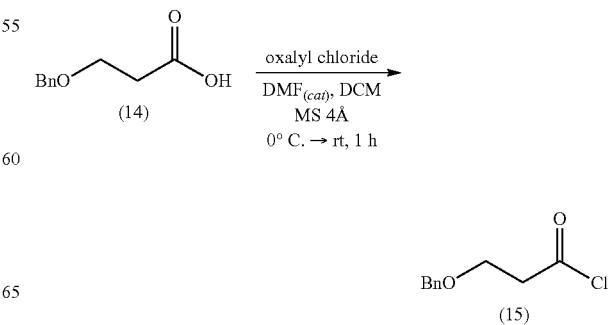

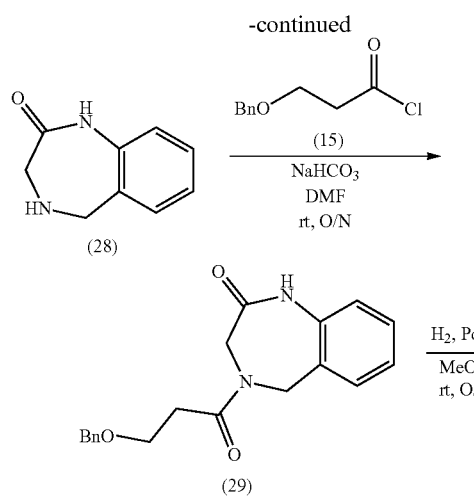

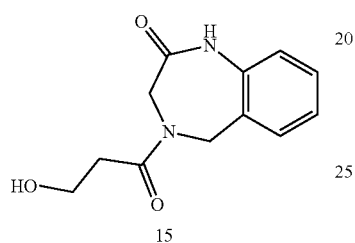

Preparation of 3-(benzyloxy)propanoyl chloride, (15). To a solution of 3-(benzyloxy)propanoic acid (14) (430 mg, 2.39 mmol) in anhydrous DCM (12 mL) containing three drops of DMF and 1.8 g of powdered molecular sieves 4 Å, cooled in an ice bath, was added oxalyl chloride (1.2 g, 9.4 mmol) in two portions over 3 min. After 30 minutes, the ice bath was removed. One hour after warming to room temperature, the mixture was concentrated under reduced pressure, which provided 2.3 g of the target acyl chloride adsorbed on the molecular sieves surface, which was assumed to contain 20 wt % of (15).

Preparation of 4-(3-(benzyloxy)propanoyl)-4,5-dihydro-1H-benzo[e][1,4]diazepin-2(3H)-one, (29). An aliquot of 3-(benzyloxy)propanoyl chloride (15) adsorbed on the molecular sieves powder (430 mg, 0.43 mmol) was added to the solution of 4,5-dihydro-1H-benzo[e][1,4]diazepin-2(3H)-one (28) (60 mg, 0.37 mmol) in DMF (5 mL) followed 30 minutes later by the addition of sodium bicarbonate (100 mg, 1.2 mmol). After overnight, the mixture was filtered through a Celite® plug, the plug was washed with DCM. A few drops of acetic acid were added to the filtrate and the mixture was concentrated under reduced pressure. The residue was loaded on silica gel column as a solution in minimal amount of DCM and the product eluted with a hexane-ethyl acetate 30%→80% gradient, which provided (29) (90 mg, 75% yield) as an off-white powder.

Preparation of 4-(3-hydroxypropanoyl)-4,5-dihydro-1H-benzo[e][1,4]diazepin-2(3H)-one, 15. To a solution of 4-(3-(benzyloxy)propanoyl)-4,5-dihydro-1H-benzo[e][1,4]diazepin-2(3H)-one (29) (90 mg, 0.27 mmol) in methanol (15 mL) was added palladium on carbon (10% by weight, 55% wet, 60 mg, 0.025 mmol), the atmosphere in the flask was substituted with hydrogen by connecting the flask to a vacuum line for 5 min with subsequent purging with a hydrogen gas (repeated 3 times) and the suspension was stirred under positive hydrogen pressure (balloon). After overnight, the mixture was diluted with DCM (15 mL) and filtered through a Celite® plug. The catalyst and plug was washed with DCM (2×15 mL), and the filtrate was concentrated under reduced pressure. The product was purified by a silica gel column chromatography (eluted with ethyl acetate-methanol 2%→12%), which after trituration with ether and drying provided 15 (29 mg, 46% yield) as an off-white powder.

$^1$H NMR (600 MHz, DMSO-d6) δ (two sets of signals in ratio 0.6:0.4) 10.14-10.01 (two singlets, 1H), 7.36-7.23 (m, 2H), 7.13-6.98 (m, 2H), 4.69 (s, 1.2H), 4.56 (s, 0.8H), 4.55-4.52 (m, 1H), 4.34 (s, 1.2H), 4.31 (s, 0.8H), 3.63-3.57 (m, 2H), 2.52-2.45 (m, 2H). LC/MS: Eluent system C (retention time: 4.08 min); ESI-MS 235 [M+H]$^+$ and 233 [M−H]$^−$.

Compound 16

Synthesis of 1-(3-hydroxypropanoyl)-3,4-dihydro-1H-benzo[e][1,4]diazepin-5(2H)-one, 16

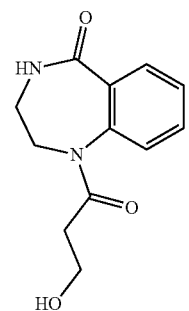

Compound 16 was synthesized as in Scheme 20.

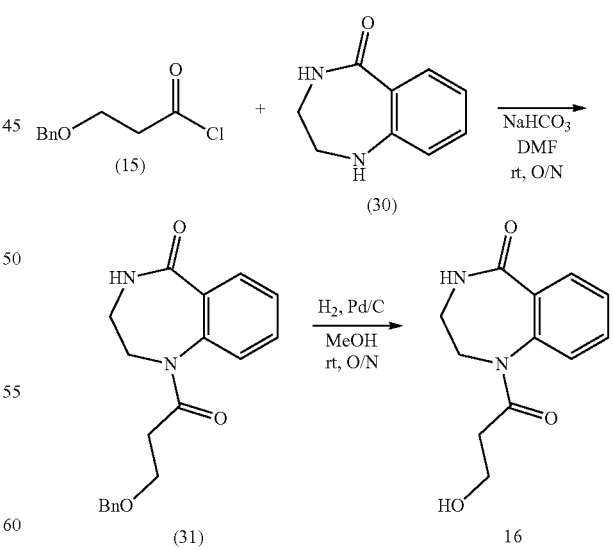

Preparation of 1-(3-(benzyloxy)propanoyl)-3,4-dihydro-1H-benzo[e][1,4]diazepin-5(2H)-one, (31). Treatment of 3,4-dihydro-1H-benzo[e][1,4]diazepin-5(2H)-one (30) (60 mg, 0.37 mmol) with the 3-(benzyloxy)propanoyl chloride (15) (1.2 equivalents) as described for (29) in Scheme 19 provided after the column chromatography (eluted with hexane-ethyl acetate 30%→100%) compound (31) (50 mg, 41% yield) as a white powder.

Preparation of 1-(3-hydroxypropanoyl)-3,4-dihydro-1H-benzo[e][1,4]diazepin-5(2H)-one, 16. Hydrogenolysis of 1-(3-(benzyloxy)propanoyl)-3,4-dihydro-1H-benzo[e][1,4]diazepin-5(2H)-one (31) (50 mg, 0.15 mmol) as described for 15 in Scheme 19, after purification by a silica gel column chromatography (eluted with ethyl acetate-methanol 2%→12%) provided compound 16 (12 mg, 34% yield) as a grey powder.

$^1$H NMR (600 MHz, DMSO-d6) δ 8.23 (t, J=5.3 Hz, 1H), 7.65-7.58 (m, 2H), 7.53 (dd, J=7.3, 7.5 Hz, 1H), 7.41 (d, J=7.5 Hz, 1H), 4.53-4.44 (m, 2H), 3.59-3.53 (m, 1H), 3.51-3.44 (m, 1H), 3.25-3.19 (m, 1H), 3.12 (dd, J=3.6, 12.7 Hz, 1H), 2.95-2.87 (m, 1H), 2.32-2.26 (m, 1H), 1.91-1.85 (m, 1H). LC/MS: Eluent system C (retention time: 3.29 min); ESI-MS 235 [M+H]$^+$.

Compound 17

Synthesis of 5-(3-hydroxypropanoyl)-4,5-dihydro-1H-benzo[b][1,4]diazepin-2(3H)-one, 17

4,5-dihydro-1H-benzo[b][1,4]diazepin-2(3H)-one (32) (60 mg, 0.37 mmol) with the 3-(benzyloxy)propanoyl chloride (15) (1.2 equivalents) as described for (29) in Scheme 19 provided after silica gel column chromatography (eluted with hexane-ethyl acetate 30%→100%) compound (33) (70 mg, 58% yield) as an off-white powder.

Preparation of 5-(3-hydroxypropanoyl)-4,5-dihydro-1H-benzo[b][1,4]diazepin-2(3H)-one, 17. Hydrogenolysis of 5-(3-(benzyloxy)propanoyl)-4,5-dihydro-1H-benzo[b][1,4]diazepin-2(3H)-one (33) (70 mg, 0.21 mmol) as described for 15 in Scheme 19, provided after purification by a column chromatography (eluent ethyl acetate-methanol 2%→12%) compound 17 (26 mg, 74% yield) as a grey powder.

$^1$H NMR (600 MHz, DMSO-d6) δ 9.77 (s, 1H), 7.45-7.35 (m, 2H), 7.27-7.11 (m, 2H), 4.71 (br s, 1H), 4.47 (br s, 1H), 3.60-3.45 (m, 2H), 3.44-3.30 (m, 2H), 2.33-2.23 (m, 2H), 1.90-1.83 (m, 1H). LC/MS: Eluent system C (retention time: 4.22 min); ESI-MS 235.2 [M+H]$^+$ and 233.0 [M–H]$^-$.

Compound 18

Synthesis of 6,7-difluoro-4-(3-hydroxypropanoyl)-3,4-dihydroquinoxalin-2(1H)-one, 18

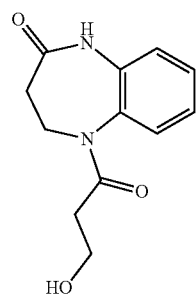

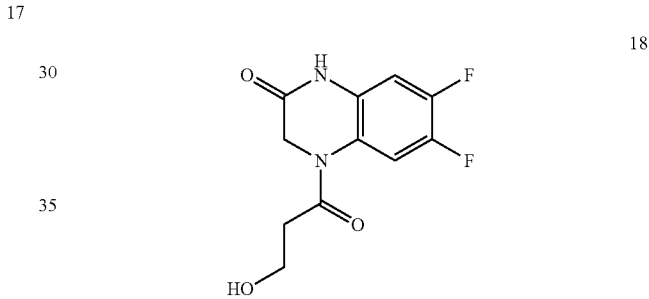

Compound 17 was synthesized as in Scheme 21.

Compound 18 was synthesized as in Scheme 22.

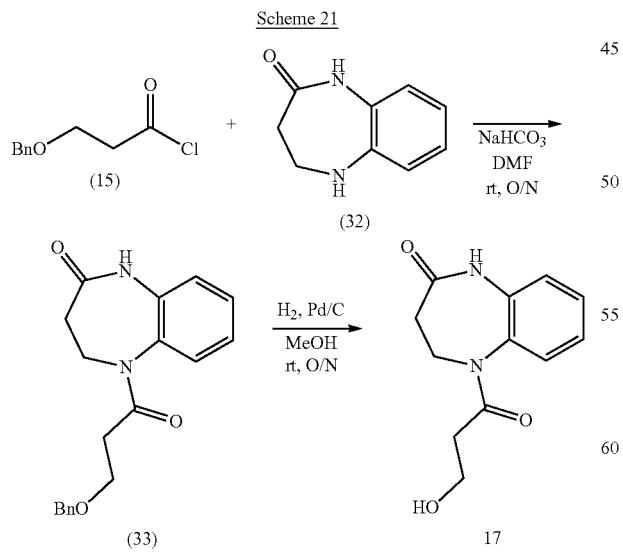

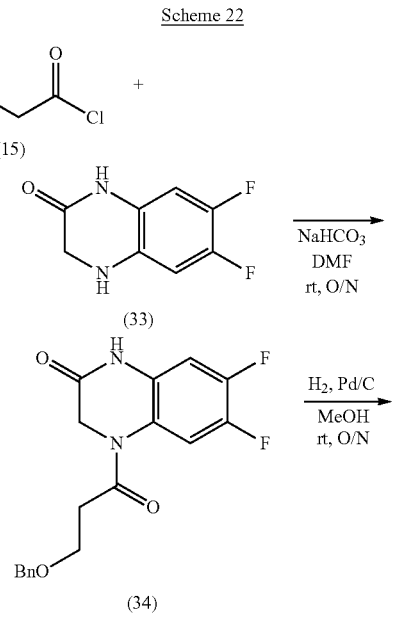

Preparation of 5-(3-(benzyloxy)propanoyl)-4,5-dihydro-1H-benzo[b][1,4]diazepin-2(3H)-one, (33). Treatment of

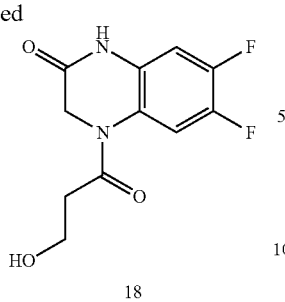

18

Preparation of 4-(3-(benzyloxy)propanoyl)-6,7-difluoro-3,4-dihydroquinoxalin-2(1H)-one, (34). Treatment of 6,7-difluoro-3,4-dihydroquinoxalin-2(1H)-one (33) (90 mg, 0.49 mmol) with the 3-(benzyloxy)propanoyl chloride (15) (20 wt % adsorbed on molecular sieves, 430 mg, 0.45 mmol) as described for (29) in Scheme 19 provided after the silica gel column chromatography (eluted with 20%→80% ethyl acetate in hexanes) compound (34) (120 mg, 77% yield) as an off-white powder.

Preparation of 6,7-difluoro-4-(3-hydroxypropanoyl)-3,4-dihydroquinoxalin-2(1H)-one, 18. Hydrogenolysis of 4-(3-(benzyloxy)propanoyl)-6,7-difluoro-3,4-dihydroquinoxalin-2(1H)-one (34) (120 mg, 0.34 mmol) as described for 15 in Scheme 19 provided after purification by a silica gel column chromatography (eluted with ethyl acetate-methanol 2%) compound 18 (48 mg, 54% yield) as a white powder.

$^1$H NMR (600 MHz, DMSO-d6) δ 10.75 (s, 1H), 7.80 (dd, J=8.7, 11.2 Hz, 1H), 6.99 (dd, J=8.2, 10.6 Hz, 1H), 4.69 (t, J=5.0 Hz, 1H), 4.35 (s, 2H), 3.72-3.65 (m, 2H), 2.71-2.65 (m, 2H). LC/MS: Eluent system C (retention time: 5.21 min); ESI-MS 257 [M+H]$^+$ and 255 [M−H]$^−$.

Compound 19

3,4-dihydro-4-(3,3,3-trifluoro-1-oxopropyl)-2(1H)-quinoxalinone, 19

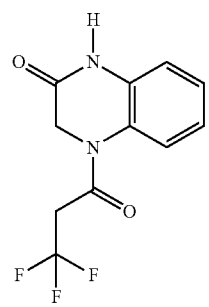

19

Compound 3,4-dihydro-4-(3,3,3-trifluoro-1-oxopropyl)-2(1H)-quinoxalinone, 19 is commercially available (CAS #1455652-24-0) or it can be generated by one skilled in the art using chemistry similar to that reported herein.

Compound 20

Synthesis of 4-(3-hydroxybutanoyl)-3,4-dihydroquinoxalin-2(1H)-one, 20

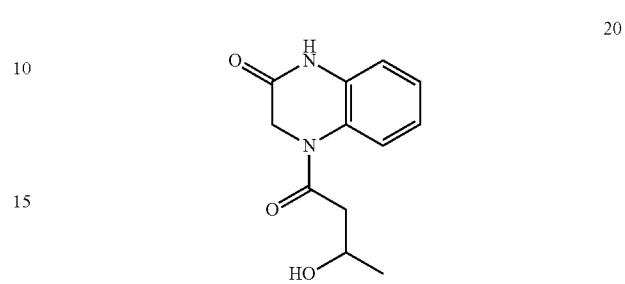

20

Compound 20 was synthesized as in Scheme 23.

Scheme 23

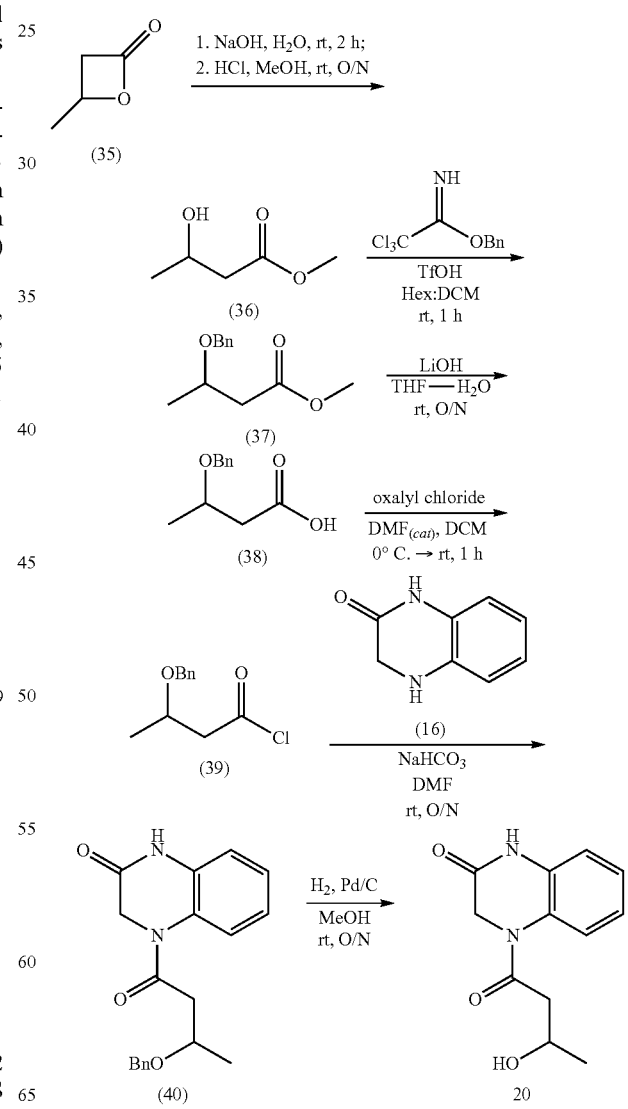

Preparation of methyl 3-hydroxybutanoate, (36). An emulsion of β-butyrolactone (1.0 g, 11.6 mmol) in aqueous solution (15 mL) of sodium hydroxide (40 mg, 1 mmol) was stirred for 2 h upon which it was concentrated under reduced pressure. Methanol (5 mL) was added to the residue, followed by concentrated hydrochloric acid (0.2 mL, 2.3 mmol). After overnight at ambient temperature, the mixture was concentrated under reduced pressure and the residue was partitioned between ethyl acetate and 2% aqueous sodium bicarbonate solution. The separated organic layer was dried over sodium sulfate, filtered and concentrated under reduced pressure, which provided (36) (550 mg, maximum 4.7 mmol). This material was used in the next step without further purification.

Preparation of methyl 3-(benzyloxy)butanoate, (37). Methyl 3-hydroxybutanoate (36) (550 mg, maximum 4.7 mmol) was dissolved in DCM (4 mL) and then hexane (4 mL) was added to the solution followed by the benzyl 2,2,2-trichloroacetamidate (2.5 g, 9.9 mmol) and trifluoromethanesulfonic acid (0.4 g, 2.7 mmol). After overnight at ambient temperature, the reaction mixture was diluted with ethyl acetate (10 mL), washed with 5% sodium bicarbonate solution, then dried over anhydrous sodium sulfate, filtered and concentrated under reduced pressure, which provided (37) (2.6 g). This material was used in the next step without further purification.

Preparation of 3-(benzyloxy)butanoic acid, (38). Methyl 3-(benzyloxy)butanoate (37) (2.6 g) dissolved in THF (10 mL) was mixed with a 1M solution of LiOH (8 mL). After overnight, the resulting mixture was washed with chloroform (30 mL) and then a 1M solution of sodium bisulfate was added to the separated aqueous layer to adjust pH of the solution to 2. The resulting suspension was extracted with ethyl acetate (3×20 mL). The combined organic layer was dried with sodium sulfate, filtered and concentrated under reduced pressure, which provided (38) (1.3 g that was approximately 60% pure based on the LC/MS analysis @254 nm). LC/MS: Eluent system B (retention time: 5.24 min); ESI-MS 195 [M+H]+ and 193 [M−H]−. This material was used in the next step without further purification.

Preparation of 3-(benzyloxy)butanoyl chloride (39). 3-(Benzyloxy)butanoic acid (38) (550 mg, 1.5 mmol) was converted into a corresponding acid chloride (39) following the procedure described for (15) in Scheme 19. The product (39) was used directly in the next step without further purification.

Preparation of 4-(3-(benzyloxy)butanoyl)-3,4-dihydroquinoxalin-2(1H)-one, (40). As described for (29) in Scheme 19, 3-(benzyloxy)butanoyl chloride (39) (1.5 mmol) was reacted with 3,4-dihydro-1H-quinoxalin-2-one (16) (150 mg, 1.0 mmol) in DMF (8 mL) in the presence of sodium bicarbonate (160 mg, 2 mmol). Purification of the product by silica gel column chromatography (eluted with hexane-ethyl acetate 20%-80%) provided (40) (70 mg, 22% yield) as white powder.

Preparation of 4-(3-hydroxybutanoyl)-3,4-dihydroquinoxalin-2(1H)-one, 20. Hydrogenolysis of 4-(3-(benzyloxy)butanoyl)-3,4-dihydroquinoxalin-2(1H)-one (40) (70 mg, 0.21 mmol) following the procedure described for 15 in Scheme 19 provided after silica gel column chromatography (eluted with hexane-ethyl acetate 35%-100%) compound 20 (17 mg, 33% yield) as white powder.
¹H NMR (600 MHz, DMSO-d6) δ 10.67 (s, 1H), 7.54 (br s, 1H), 7.23-7.18 (m, 1H), 7.05 (t, J=7.6 Hz, 1H), 7.02 (d, J=7.9 Hz, 1H), 4.71 (d, J=4.7 Hz, 1H), 4.38 (d, J=16.2 Hz, 1H), 4.32 (d, J=16.2 Hz, 1H), 4.10-4.04 (m, 1H), 2.71-2.66 (m, 1H), 2.51-2.46 (m, 1H), 1.05 (br s, 3H). LC/MS: Eluent system C (retention time: 5.37 min); ESI-MS 235 [M+H]+.

Compound 21

Synthesis of 4-(3-hydroxypropanoyl)-6,7-dimethyl-3,4-dihydroquinoxalin-2(1H)-one, 21

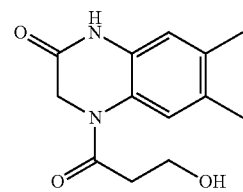

Compound 21 was synthesized as in Scheme 24.

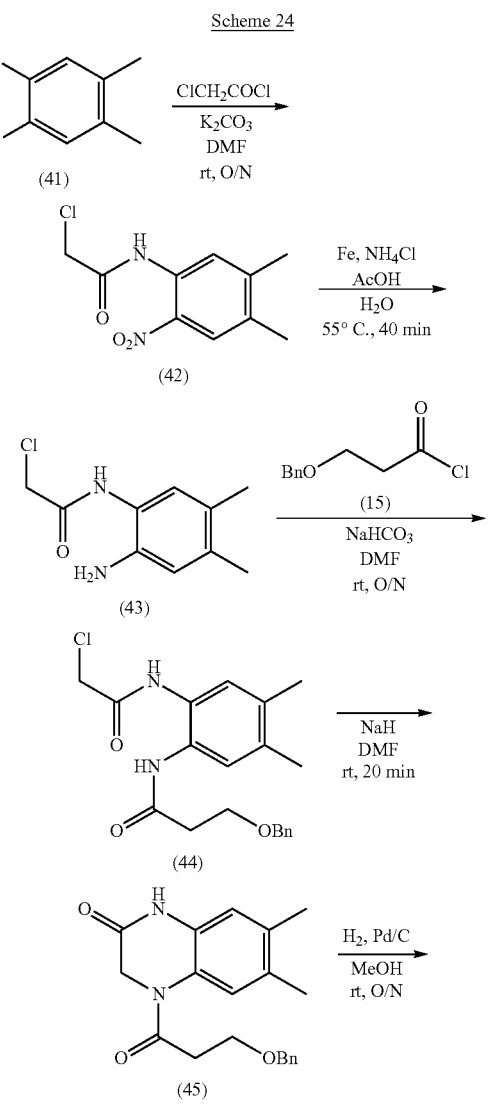

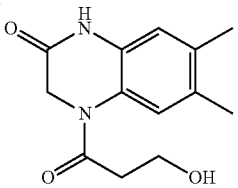

21

Preparation of 2-chloro-N-(4,5-dimethyl-2-nitrophenyl)acetamide, (42). To a stirred solution of 4,5-dimethyl-2-nitroaniline (41) (500 mg, 3.01 mmol) in DMF (10 mL) was added potassium carbonate (690 mg, 5 mmol) and chloroacetyl chloride (760 mg, 6.7 mmol). After overnight, the volatile components were removed under reduced pressure and the resulting residue was partitioned between chloroform and 1M hydrochloric acid. The organic layer was separated, dried over sodium sulfate, filtered and concentrated under reduced pressure. Recrystallization of residue from methanol provided (42) (340 mg, 47% yield) as a fluffy orange needles.

Preparation of N-(2-amino-4,5-dimethylphenyl)-2-chloroacetamide, (43). A suspension of iron powder (363 mg, 6.5 mmol) in an aqueous solution (10 mL) of ammonium chloride (35 mg, 0.65 mmol) and acetic acid (75 mg, 1.25 mmol) was stirred in a bath at 55° C. for 15 minutes, and then a solution of 2-chloro-N-(4,5-dimethyl-2-nitrophenyl)acetamide (42) (150 mg, 0.62 mmol) in DMF (3 mL) was added in one portion. After 40 minutes, to the mixture was added a saturated solution of sodium bicarbonate (5 mL) and resulting suspension was filtered through a Celite® plug. Ethyl acetate (30 mL) was used to wash the Celite® and the combined filtrate was stirred vigorously for 5 min and then the layers were separated. The organic layer was dried over sodium sulfate, filtered and concentrated under reduced pressure which provided (43) (117 mg, 89% yield).

Preparation of 3-(benzyloxy)-N-(2-(2-chloroacetamido)-4,5-dimethylphenyl)propenamide, (44). Following the procedure to generate (29) in Scheme 19 N-(2-amino-4,5-dimethylphenyl)-2-chloroacetamide (43) (117 mg, 0.55 mmol) was treated with the 3-(benzyloxy)propanoyl chloride (15), which provided after the purification by silica gel column chromatography (eluent hexane-ethyl acetate 20%-100%) compound (44) (120 mg, 58% yield) as a white solid.

Preparation of 4-(3-(benzyloxy)propanoyl)-6,7-dimethyl-3,4-dihydroquinoxalin-2(1H)-one, (45). To a solution of 3-(benzyloxy)-N-(2-(2-chloroacetamido)-4,5-dimethylphenyl)propenamide (44) (120 mg, 0.32 mmol) in DMF (3 mL) was added sodium hydride (120 mg, 3.0 mmol, 60% dispersion in oil). After 20 minutes, the mixture was treated with 1M hydrochloric acid (5 mL) and the resulting mixture was extracted with chloroform (3×15 mL). The combined organic layers were drying over sodium sulfate, filtered and concentrating under reduced pressure produced (45) which was used without further purification in the next step.

Preparation of 4-(3-hydroxypropanoyl)-6,7-dimethyl-3,4-dihydroquinoxalin-2(1H)-one, 21. Hydrogenolysis of 4-(3-(benzyloxy)propanoyl)-6,7-dimethyl-3,4-dihydroquinoxalin-2(1H)-one (45) as describe in the synthesis of 15 in Scheme 19 and after purification by silica gel column chromatography (eluted with hexane-ethyl acetate 35%-100%) provided 21 (22 mg, 28% yield over two steps) as an off-white powder.

$^1$H NMR (600 MHz, DMSO-d6) δ 10.53 (s, 1H), 7.29 (br s, 1H), 6.78 (s, 1H), 4.60 (t, J=5.3 Hz, 1H), 4.29 (s, 2H), 3.74-3.62 (m, 2H), 2.65 (t, J=6.1 Hz, 2H), 2.20 (s, 3H), 2.18 (s, 3H). LC/MS: Eluent system C (retention time: 7.07 min); ESI-MS 249 [M+H]$^+$ and 247 [M−H]$^-$ and Eluent system A (retention time: 5.65 min); ESI-MS 249 [M+H]$^+$ and 247 [M−H]$^-$.

Compound 22

Synthesis of 4-(3-hydroxycyclobutanecarbonyl)-3,4-dihydroquinoxalin-2(1H)-one, 22

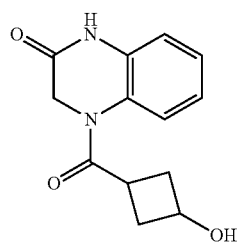

22

Compound 22 was synthesized as in Scheme 25

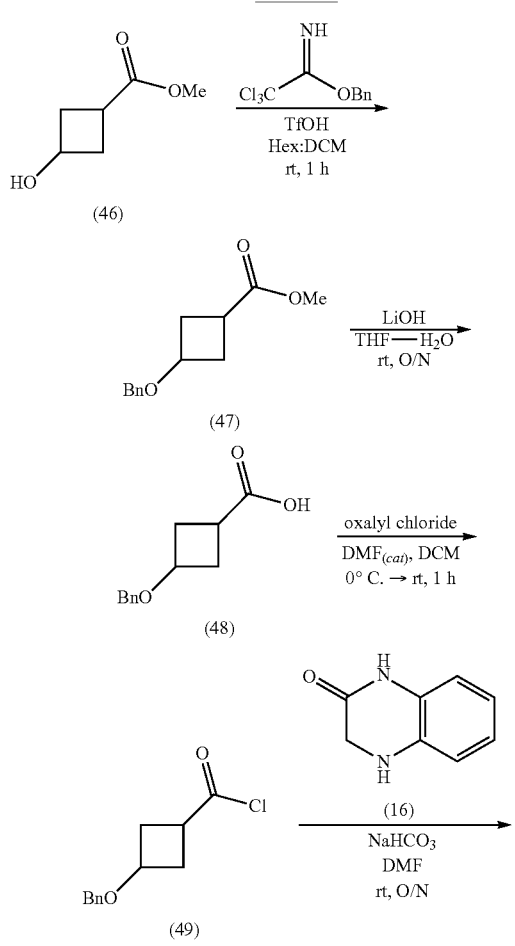

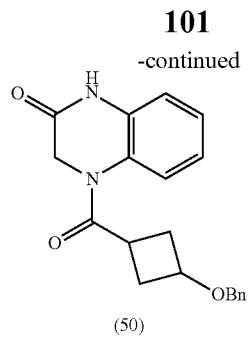

(50)

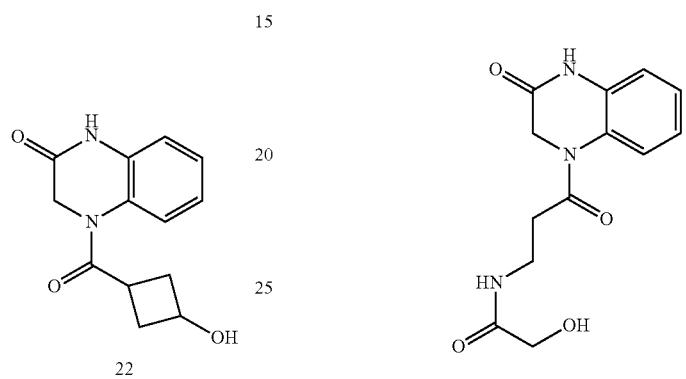

Preparation of methyl 3-(benzyloxy)cyclobutanecarboxylate, (47). Treatment of methyl 3-hydroxycyclobutanecarboxylate (46) (0.50 g, 3.8 mmol) with the benzyl 2,2,2-trichloroacetamidate (2.5 g, 9.9 mmol) and trifluoromethanesulfonic acid (0.28 g, 2.7 mmol) following the procedure for (37) in Scheme 23 provided after evaporation provided (47) (3.3 g). The material was used in the next step without further purification.

Preparation of 3-(benzyloxy)cyclobutanecarboxylic acid (48). Saponification of the methyl 3-(benzyloxy)cyclobutanecarboxylate (47) (3.3 g, maximum of 3.8 mmol) following the procedure for (38) in Scheme 23 after purification by silica gel column chromatography (eluent of hexane-ethyl acetate 0%→100%) provided (48) (750 mg). The material was used in the next step without further purification.

Preparation of 3-(benzyloxy)cyclobutanecarbonyl chloride (49). Conversion of the 3-(benzyloxy)cyclobutanecarboxylic acid (48) (400 mg, 2 mmol) into (49) was achieved by following the procedure for (15) in Scheme 19. The residue obtained was used immediately in the next step.

Preparation of 4-(3-(benzyloxy)cyclobutanecarbonyl)-3,4-dihydroquinoxalin-2(1H)-one, (50). Treatment of 3-(benzyloxy)cyclobutanecarbonyl chloride (49) (2 mmol) with 3,4-dihydro-1H-quinoxalin-2-one (16) (150 mg, 1.0 mmol) following the procedure for (29) in Scheme 19 provided after purification by column chromatography (eluent of hexane-ethyl acetate 20%→80%) compound (50) (143 mg, 42% yield over two steps).

Preparation of 4-(3-hydroxycyclobutanecarbonyl)-3,4-dihydroquinoxalin-2(1H)-one, 22. Hydrogenolysis of 4-(3-(benzyloxy)cyclobutanecarbonyl)-3,4-dihydroquinoxalin-2(1H)-one (50) (143 mg, 0.42 mmol) following the procedure for 15 in Scheme 19 followed by purification with silica gel column chromatography (eluent ethyl acetate-methanol 1%→5%) provided 22 (90 mg, 86% yield) as a colorless solidified foam.

$^1$H NMR (600 MHz, DMSO-d6) δ 10.67 (s, 1H), 7.40-7.15 (m, 2H), 7.07-7.03 (m, 1H), 7.01 (d, J=7.8 Hz, 1H), 5.10 (d, J=6.7 Hz, 1H), 4.30 (br s, 2H), 3.88 (br s, 1H), 2.99-2.92 (m, 1H), 2.39-2.13 (m, 2H), 1.99-1.92 (m, 2H). LC/MS: Eluent system C (retention time: 5.49 min); ESI-MS 247 [M+H]$^+$.

Compound 23

Synthesis of 2-hydroxy-N-(3-oxo-3-(3-oxo-3,4-dihydroquinoxalin-1(2H)-yl)propyl)acetamide, 23

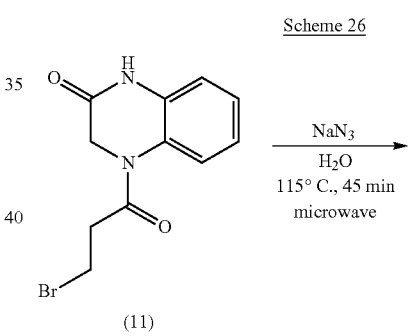

Compound 23 was synthesized as in Scheme 26.

Scheme 26

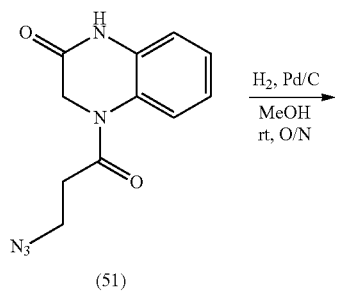

103

-continued

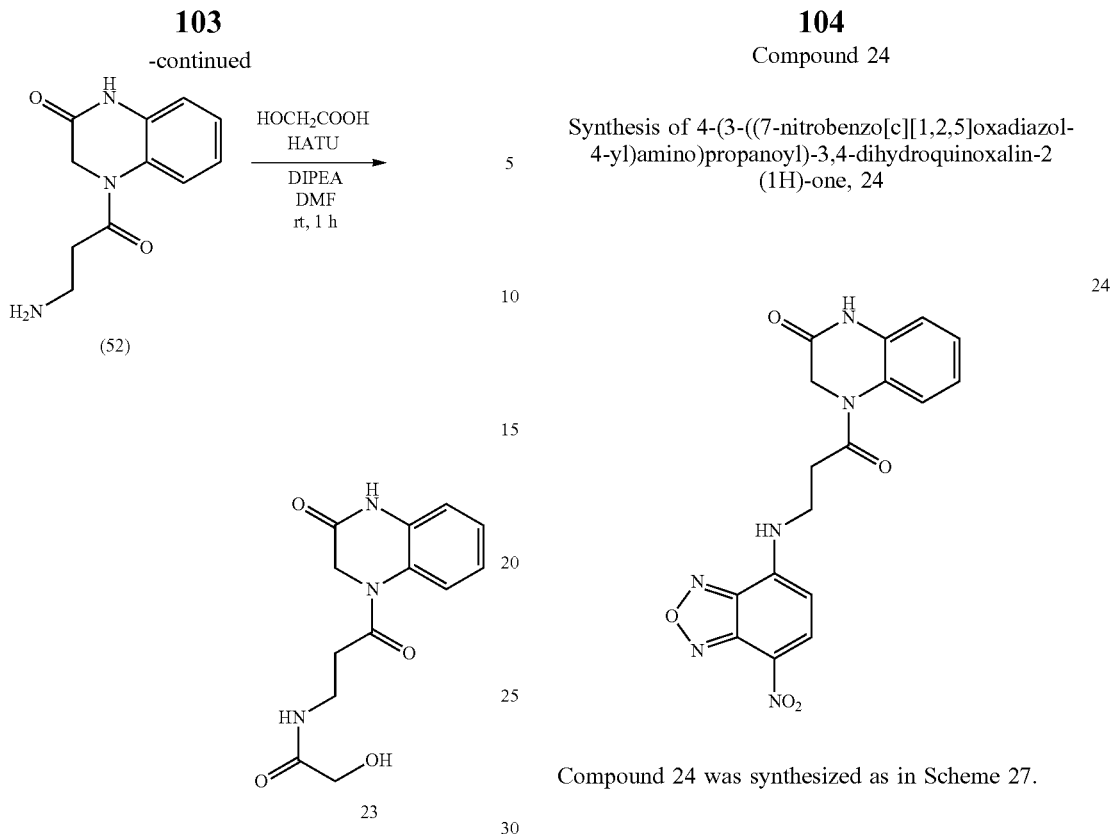

Compound 24

Synthesis of 4-(3-((7-nitrobenzo[c][1,2,5]oxadiazol-4-yl)amino)propanoyl)-3,4-dihydroquinoxalin-2(1H)-one, 24

Preparation of 4-(3-azidopropanoyl)-3,4-dihydroquinoxalin-2(1H)-one (51). A mixture of 4-(3-bromopropanoyl)-3,4-dihydroquinoxalin-2(1H)-one (11) (500 mg, 1.77 mmol) and sodium azide (620 mg, 9.5 mmol) in water (10 mL) was heated at 115° C. using microwave irradiation for 45 minutes. After cooling to ambient temperature, the mixture was extracted with ethyl acetate (2×20 mL). The combined organic layer was dried over sodium sulfate, filtered and concentrated under reduced pressure, which provided (51) (250 mg, 57% yield) as a white powder.

Preparation of 4-(3-aminopropanoyl)-3,4-dihydroquinoxalin-2(1H)-one, (52). Hydrogenolysis of 4-(3-azidopropanoyl)-3,4-dihydroquinoxalin-2(1H)-one (51) (250 mg, 1.02 mmol) as described for 15 in Scheme 19 provided (52) in quantitative yield (240 mg). This material was used without further purification.

Preparation of 2-hydroxy-N-(3-oxo-3-(3-oxo-3,4-dihydroquinoxalin-1(2H)-yl)propyl)acetamide, 23. To a solution of 4-(3-aminopropanoyl)-3,4-dihydroquinoxalin-2(1H)-one (52) (160 mg, 0.73 mmol), 2-hydroxyacetic acid (250 mg, 3.3 mmol) in DMF (8 mL) was added HATU (380 mg, 1 mmol) followed by DIPEA (500 mg, 3.9 mmol). After 1 h, the mixture was concentrated under reduced pressure and the product purified by column chromatography (eluted with ethyl acetate-methanol 1%→8%) provided 23 (186 mg, 92% yield) as a white crystalline powder.

$^1$H NMR (600 MHz, DMSO-d6) δ 10.69 (s, 1H), 7.77 (t, J=6.0 Hz, 1H), 7.67 (br s, 1H), 7.20 (br s, 1H), 7.07-7.00 (m, 2H), 5.46 (br s, 1H), 4.34 (br s, 2H), 3.75 (d, J=5.3 Hz, 2H), 2.71 (br s, 2H), 1.29-1.23 (m, 2H). LC/MS: Eluent system C (retention time: 4.03 min); ESI-MS 278 [M+H]$^+$ and 276 [M−H]$^−$.

Compound 24 was synthesized as in Scheme 27.

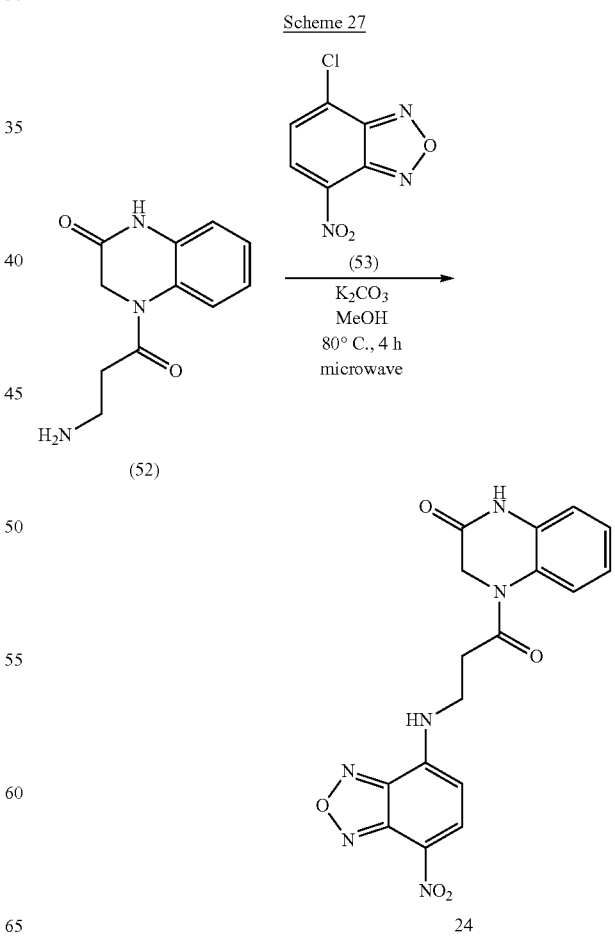

Preparation of 4-(3-((7-nitrobenzo[c][1,2,5]oxadiazol-4-yl)amino)propanoyl)-3,4-dihydroquinoxalin-2(1H)-one, 24. A solution of the 4-(3-aminopropanoyl)-3,4-dihydroquinoxalin-2(1H)-one (52) (80 mg, 0.36 mmol) in methanol (10 mL) was added into a 30 mL microwave vial equipped with a magnetic stir bar and containing 4-chloro-7-nitrobenzofurazan (53) (80 mg, 0.4 mmol) and potassium carbonate (100 mg, 0.72 mmol). The mixture was subjected to microwave irradiation with the temperature set at 80° C. for 4 h. The resulting mixture was filtered, and the filter washed with ethyl acetate, and the combined filtrate was concentrated under reduced pressure. The product was purified by silica gel column chromatography (eluted with ethyl acetate) provided 24 (21.8 mg, 16% yield) as a yellow powder.

$^1$H NMR (600 MHz, DMSO-d6) δ 10.65 (s, 1H), 9.38 (br s, 1H), 8.48 (br s, 1H), 7.50 (br s, 1H), 7.17 (br s, 1H), 7.06-6.99 (m, 1H), 6.96 (d, J=7.8 Hz, 1H), 6.38 (br s, 1H), 4.35 (s, 2H), 3.72 (br s, 2H), 3.04 (br s, 2H). LC/MS: Eluent system C (retention time: 7.69 min); ESI-MS 383 [M+H]$^+$ and 381.0 [M−H]$^−$. Eluent system B (retention time: 4.38 min); ESI-MS 383 [M+H]$^+$ and 381.0 [M−H]$^−$.

Compound 25

3,4-dihydro-β,3-dioxo-1(2H)-quinoxalinepropanenitrile, 25

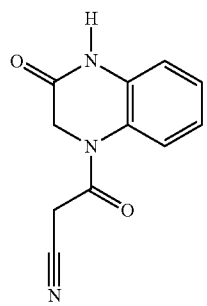

Compound 3,4-dihydro-β,3-dioxo-1(2H)-quinoxalinepropanenitrile, 25 is commercially available (CAS #1042790-95-3) or it can be generated by one skilled in the art using chemistry similar to that reported herein.

Compound 26

N-[3-(3,4-dihydro-3-oxo-1(2H)-quinoxalinyl)-3-oxopropyl]-acetamide, 26

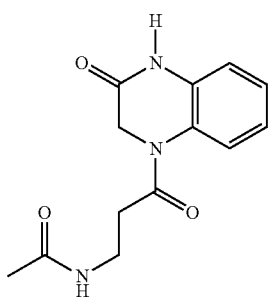

Compound N-[3-(3,4-dihydro-3-oxo-1(2H)-quinoxalinyl)-3-oxopropyl]-acetamide, 26 is commercially available (CAS #1281336-03-5) or it can be generated by one skilled in the art using chemistry similar to that reported herein.

Compound 27

Synthesis of 1-(3-hydroxypropyl)-6-methyl-1,4-dihydroquinoxaline-2,3-dione, 27

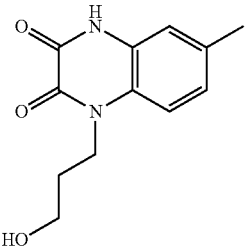

Compound 27 was synthesized as in Scheme 28.

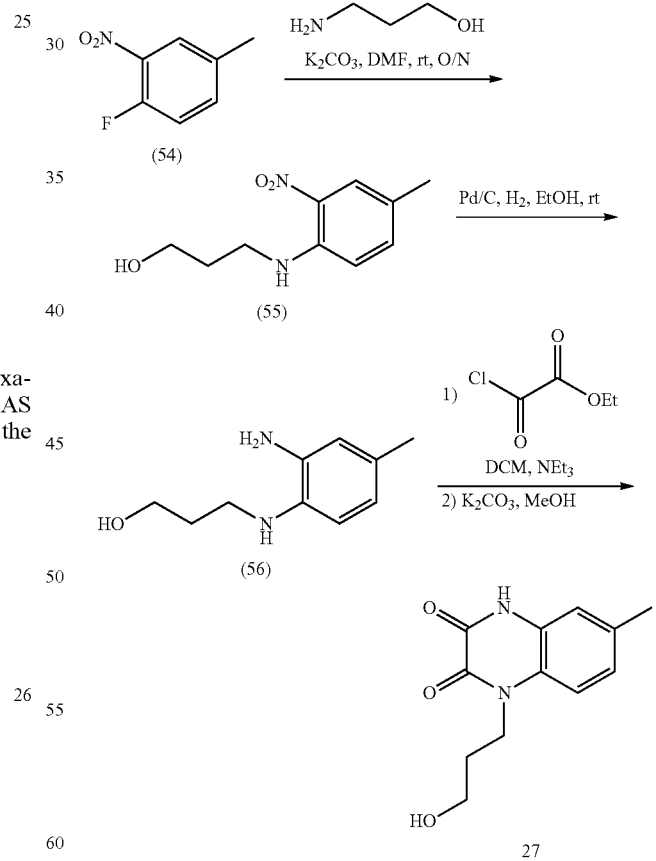

Preparation of 3-(4-methyl-2-nitroanilino)propan-1-ol, (55). A mixture of 1-fluoro-4-methyl-2-nitrobenzene (54) (0.25 g, 1.6 mmol), 3-aminopropan-1-ol (242.0 mg, 3.22 mmol) and K$_2$CO$_3$ (276.0 mg, 1.99 mmol) in DMF (5 mL) was stirred at room temperature. After overnight, the mixture was concentrated under reduced pressure, diluted with chloroform (5 mL), adsorbed onto silica gel (1 g) and the product purified by column chromatography on silica gel (eluted with 0-5% methanol in chloroform), which generated (55) (0.32 g, 95% yield) as a white solid.

Preparation of 3-(2-amino-4-methylanilino)propan-1-ol, (56). A solution of 3-(4-methyl-2-nitroanilino)propan-1-ol (55) (0.32 g, 1.5 mmol) in ethanol (50 mL) was purged with nitrogen for 5 min and 10% Pd/C (0.32 g) was added. The mixture was stirred under positive hydrogen pressure (balloon) at room temperature for 18 h. The mixture was then filtered through a pad of Celite®, the pad was washed with ethanol (15 mL) and the combined filtrate was concentrated under reduced pressure. The product was purified by chromatography on silica gel (eluted with 0-10% methanol in chloroform), which provided (56) (0.16 g, 59% yield) as a gum.

Preparation of 1-(3-hydroxypropyl)-6-methyl-1,4-dihydroquinoxaline-2,3-dione, 27. To a solution of 3-(2-amino-4-methylanilino)propan-1-ol (56) (0.16 g, 0.89 mmol) and triethylamine (0.51 g, 5.0 mmol) cooled in an ice bath, was slowly added ethyl chloro(oxo)acetate (0.37 g, 2.7 mmol). The ice bath was removed, and after 18 h at ambient temperature, the mixture was concentrated under reduced pressure. The resulting residue was diluted with methanol (5 mL) and $K_2CO_3$ (0.14 g, 1.0 mmol) was added. After 18 h, the mixture was concentrated under reduced pressure. The residue was adsorbed onto silica gel (1 g) and the product was purified by column chromatography on silica gel (eluted with 0-5% methanol in chloroform), which generated 27 (31.0 mg, 15% yield) as a white solid.

$^1$H NMR (600 MHz, DMSO-$d_6$) δ 11.98 (br s, 1H), 7.30 (d, J=8.6 Hz, 1H), 7.02 (dd, J=1.0, 8.6 Hz, 1H), 6.99 (d, J=1.0 Hz, 1H), 4.64 (t, J=5.1 Hz, 1H), 4.15-4.10 (m, 2H), 3.53-3.49 (m, 2H), 2.30 (s, 3H), 1.79-1.74 (m, 2H). LC/MS: Eluent system C (retention time: 6.10 min); ESI-MS 235 [M+H]$^+$.

Compound 28

Synthesis of 1-(3-hydroxypropyl)-7-(pyridin-3-yl)-1,4-dihydroquinoxaline-2,3-dione, 28

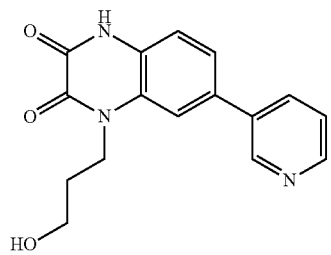

28

Compound 28 was synthesized as in Scheme 29.

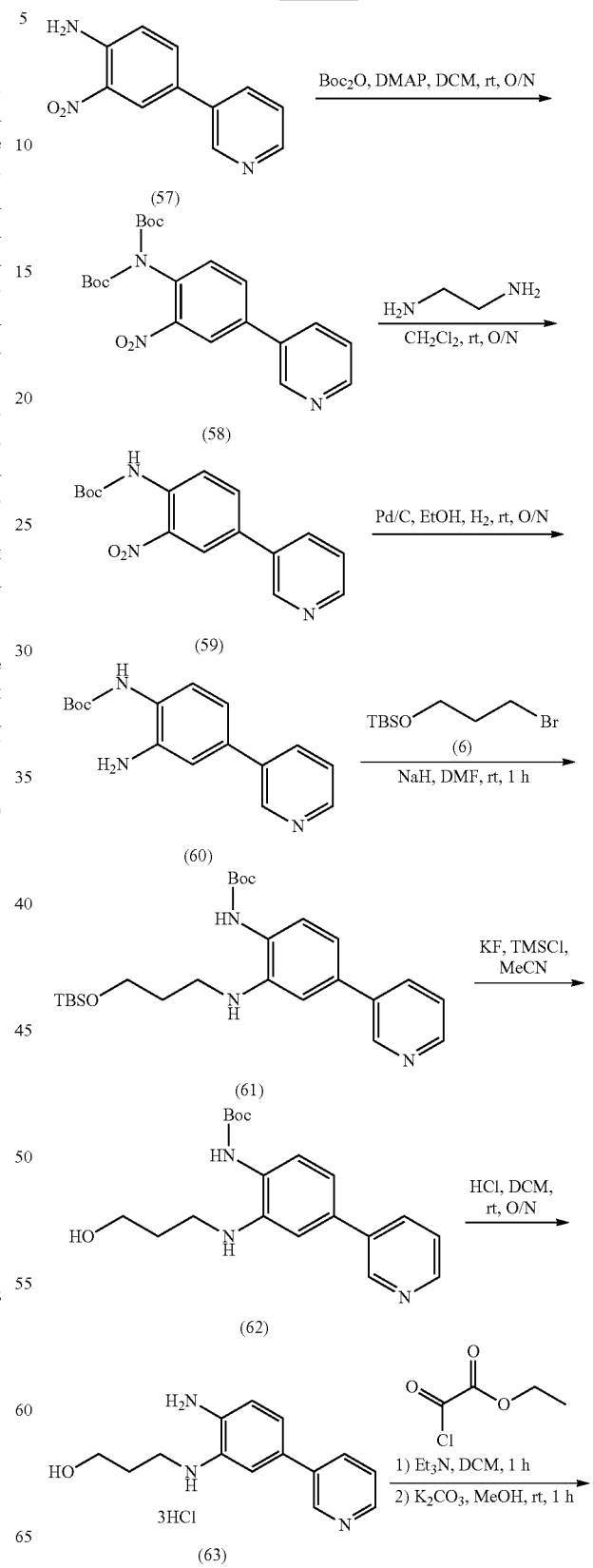

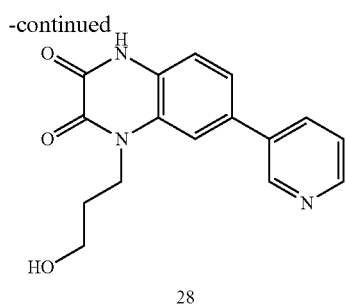

28

Preparation of di-tert-butyl [2-nitro-4-(pyridin-3-yl)phenyl]-2-imidodicarbonate, (58). A mixture of 2-nitro-4-(pyridin-3-yl)aniline (57) (220.0 mg, 1.02 mmol), Boc$_2$O (0.54 g, 2.5 mmol), DMAP (24.0 mg, 0.2 mmol) and DCM (25 mL) was stirred overnight at room temperature. After which it was concentrated under reduced pressure, which generated (58) (0.42 g, 98% yield) as a gum. This material was used in the next step without further purification.

Preparation of tert-butyl [2-nitro-4-(pyridin-3-yl)phenyl] carbamate, (59). To a solution di-tert-butyl [2-nitro-4-(pyridin-3-yl)phenyl]-2-imidodicarbonate (58) (0.42 g, 1.0 mmol) in DCM (25 mL) was added 1,2-diaminoethane (0.25 mL, 3.75 mmol). After overnight, it was then concentrated under reduced pressure and the product was purified by column chromatography on silica gel (eluted with 0 to 50% ethyl acetate in hexanes), which generated (59) (0.29 g, 90% yield) as a gum. This material was used in the next step without further purification.

Preparation of tert-butyl [2-amino-4-(pyridin-3-yl)phenyl]carbamate, (60). A solution of tert-butyl [2-nitro-4-(pyridin-3-yl)phenyl]carbamate (59) (0.29 g, 0.91 mmol) in ethanol (50 mL) was purged with nitrogen for 5 min and 10% Pd/C (0.029 g) was added. The mixture was stirred under positive hydrogen pressure (balloon) at room temperature for 18 h, after which it was filtered through a pad of Celite®, and concentrated under reduced pressure which provided (60) (0.25 g, 96% yield) as a gum. This material was used in the next step without further purification.

Preparation of tert-butyl {2-[(3-{[tert-butyl(dimethyl)silyl]oxy}propyl)amino]-4-(pyridin-3-yl)phenyl}carbamate, (61). To a solution of tert-butyl [2-amino-4-(pyridin-3-yl)phenyl]carbamate (60) (0.25 g, 0.88 mmol) in DMF (5 mL) was added NaH (108 mg, 2.7 mmol, 60% in oil). After 10 min, (3-bromopropoxy)(tert-butyl)dimethylsilane (6) (228.0 mg, 0.9 mmol) was added. After 1 h, the mixture was concentrated under reduced pressure and the product purified by column chromatography on silica gel (eluted with 0-50% ethyl acetate in hexanes), which generated (61) (0.34 g, 85% yield) as a gum.

Preparation of tert-butyl {2-[(3-{hydroxy}propyl)amino]-4-(pyridin-3-yl)phenyl}carbamate (62). To a solution of tert-butyl {2-[(3-{[tert-butyl(dimethyl)silyl]oxy}propyl) amino]-4-(pyridin-3-yl)phenyl}carbamate (61) (0.34 g, 0.75 mmol) in acetonitrile (5 mL) was added KF (87.0 mg, 1.5 mmol) followed by TMSCl (271.0 mg, 2.5 mmol). After 1 h, the mixture was concentrated under reduced pressure and the product was purified by column chromatography on silica gel (eluted with 0-5% methanol in chloroform), which produced (62) (178.5 mg, 70% yield) as a gum.

Preparation of 3-[2-amino-5-(pyridin-3-yl)anilino]propan-1-ol-hydrochloride, (63). To a solution of tert-butyl {2-[(3-{hydroxy}propyl)amino]-4-(pyridin-3-yl) phenyl}carbamate (62) (178.5 mg, 0.52 mmol) in DCM was added HCl (1 mL, 4M in dioxane). After overnight, the mixture was concentrated under reduced pressure and the residue was suspended in ether (10 mL) which after filtering and drying produced (63) (176 mg, 99% yield) as an off-white solid.

Preparation of 1-(3-hydroxypropyl)-7-(pyridin-3-yl)-1,4-dihydroquinoxaline-2,3-dione, 28. To a solution of 3-[2-amino-5-(pyridin-3-yl)anilino]propan-1-ol-hydrochloride (63) (0.176 g, 0.499 mmol) and triethylamine (1.0 g, 10.0 mmol) in DCM (20 mL) cooled in an ice bath was slowly added ethyl chloro(oxo)acetate (0.20 g, 1.5 mmol). The ice bath was then removed and after 1 h at ambient temperature the mixture was concentrated under reduced pressure. The resulting residue was diluted with methanol (5 mL), and K$_2$CO$_3$ (0.21 g, 1.5 mmol) was added. After 18 h, the mixture was concentrated under reduced pressure and then adsorbed onto silica gel (1 g). The product was purified by column chromatography on silica gel (eluted with 0-5% methanol in chloroform), which provided 28 (59.0 mg, 40% yield) as a white solid.

$^1$H NMR (600 MHz, DMSO-d$_6$) δ 12.14 (s, 1H), 8.87 (br s, 1H), 8.61 (br. s, 1H), 8.07 (d, J=7.5 Hz, 1H), 7.59-7.53 (m, 3H), 7.47 (d, J=1.9 Hz, 1H), 4.69 (br s, 1H), 4.23-4.10 (m, 2H), 3.58-3.50 (m, 2H), 1.84-1.79 (m, 2H). LC/MS: Eluent system C (retention time: 3.85 min); ESI-MS 298 [M+H]$^+$.

Compound 29

Synthesis of 1-(3-hydroxypropyl)-6,7-dimethyl-1,4-dihydroquinoxaline-2,3-dione, 29

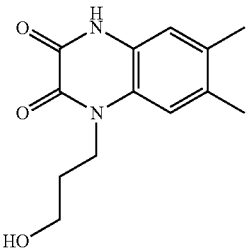

29

Compound 29 was synthesized as in Scheme 30.

Scheme 30

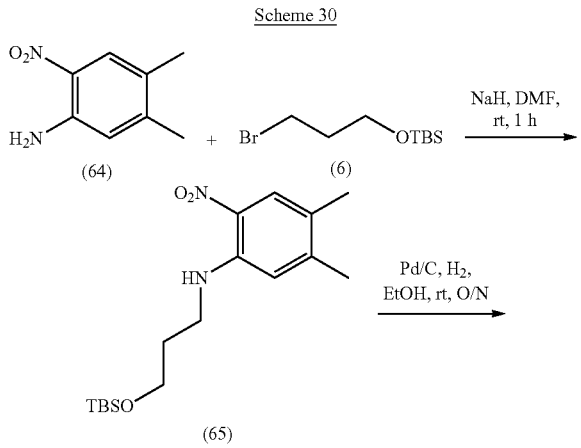

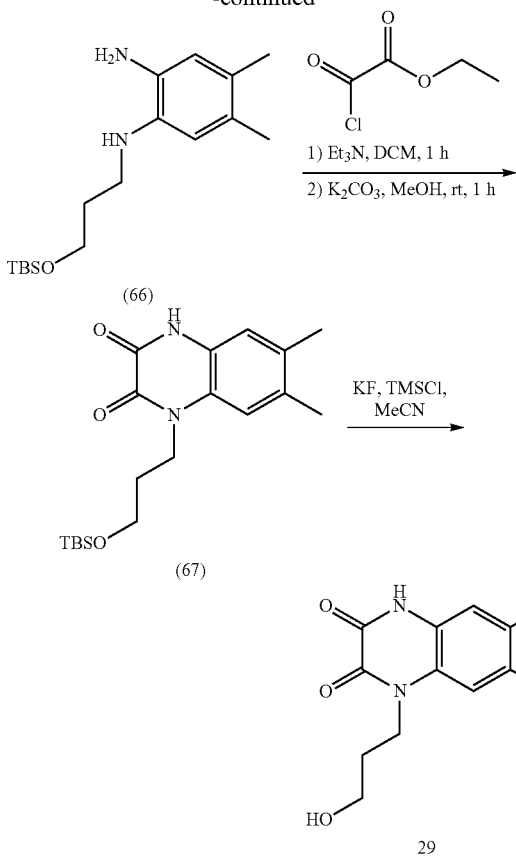

Preparation of N-(3-{[tert-butyl(dimethyl)silyl]oxy}propyl)-4,5-dimethyl-2-nitroaniline, (65). To a solution of 4,5-dimethyl-2-nitroaniline (64) (200 mg, 1.21 mmol) in DMF (5 mL) was added NaH (96.0 mg, 2.42 mmol, 60% in oil). After 10 min, (3-bromopropoxy)(tert-butyl)dimethylsilane (6) (455.8 mg, 1.799 mmol) was added dropwise. After 1 h, the mixture was concentrated under reduced pressure and the product was purified by column chromatography on silica gel (eluted with 0-50% ethyl acetate in hexanes), which provided (65) (0.37 g, 90% yield) as a gum.

Preparation of $N^1$-(3-{[tert-butyl(dimethyl)silyl]oxy}propyl)-4,5-dimethylbenzene-1,2-diamine, (66). A solution of N-(3-{[tert-butyl(dimethyl)silyl]oxy}propyl)-4,5-dimethyl-2-nitroaniline (3) (0.37 g, 1.1 mmol) in ethanol (50 mL) was purged with nitrogen for 5 min and 10% Pd/C (0.37 g) was added. The mixture was stirred under positive hydrogen pressure (balloon) at room temperature. After 18 h, the mixture was filtered through a pad of Celite®, the pad was washed with ethanol (15 mL) and concentrated under reduced pressure. The product was purified by chromatography on silica gel (eluted with gradient of 0-10% MeOH-chloroform), which provided (66) (0.26 g, 77% yield) as a gum.

Preparation of 1-(3-{[tert-butyl(dimethyl)silyl]oxy}propyl)-6,7-dimethyl-1,4-dihydroquinoxaline-2,3-dione, (67). To a solution of $N^1$-(3-{[tert-butyl(dimethyl)silyl]oxy}propyl)-4,5-dimethylbenzene-1,2-diamine (66) (0.26 g, 0.85 mmol) and triethylamine (0.51 g, 5.0 mmol) in DCM (20 mL) cooled in an ice bath was slowly added ethyl chloro(oxo)acetate (0.37 g, 2.7 mmol). The ice bath was removed and after 18 h at ambient temperature the mixture was concentrated under reduced pressure. The residue was then diluted with methanol (5 mL) and $K_2CO_3$ (138.0 mg, 0.99 mmol) was added. After 18 h, the mixture was concentrated under reduced pressure and the residue was mixed with chloroform (15 mL) and adsorbed onto silica gel (1 g). The product was purified by column chromatography on silica gel (eluted with 0-5% methanol in chloroform), which provided (67) (0.18 g, 60% yield) as a white solid.

Preparation of 1-(3-hydroxypropyl)-6,7-dimethyl-1,4-dihydroquinoxaline-2,3-dione, 29. To a solution of 1-(3-{[tert-butyl(dimethyl)silyl]oxy}propyl)-6,7-dimethyl-1,4-dihydroquinoxaline-2,3-dione (67) (0.18 g, 0.49 mmol) in acetonitrile (5 mL) was added KF (87.0 mg, 1.5 mmol) followed by TMSCl (217 mg, 2.0 mmol). After 1 h, the mixture was concentrated under reduced pressure. The product was purified by column chromatography on silica gel (eluted with 0-5% methanol in chloroform), which provided 29 (53.0 mg, 42% yield) as a white solid.

$^1$H NMR (600 MHz, DMSO-$d_6$) δ 11.84 (s, 1H), 7.14 (s, 1H), 6.88 (s, 1H), 4.57 (t, J=5.2 Hz, 1H), 4.09-4.02 (m, 2H), 3.48-3.42 (m, 2H), 2.19 (s, 3H), 2.13 (s, 3H), 1.74-1.67 (m, 2H). LC/MS: Eluent system A (retention time: 5.74 min); ESI-MS 249 [M+H]$^+$.

Compound 30

Synthesis of 5-fluoro-1-(3-hydroxypropyl)-1,4-dihydroquinoxaline-2,3-dione, 30

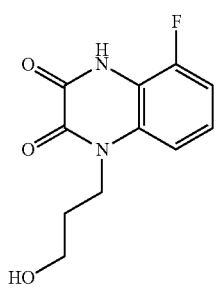

Compound 30 was synthesized as in Scheme 31.

Scheme 31

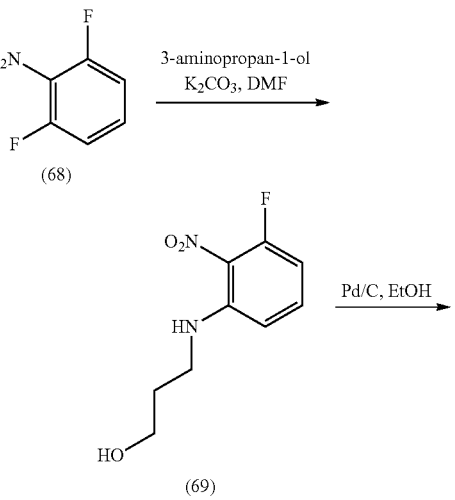

-continued

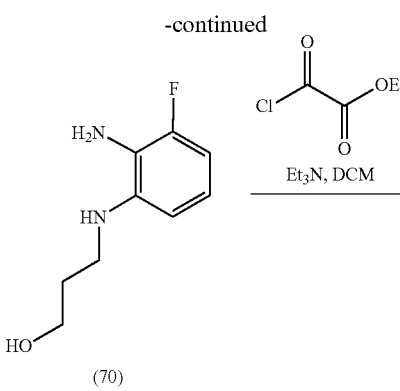

(70)

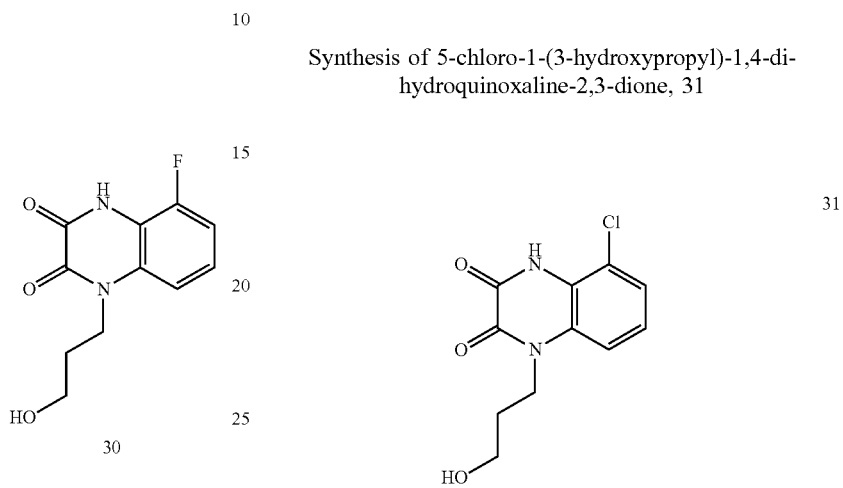

Preparation of 3-(3-fluoro-2-nitroanilino)propan-1-ol, (69). To a solution of 1,3-difluoro-2-nitrobenzene (68) (300 mg, 1.9 mmol) in DMF (10 mL) was added 3-aminopropan-1-ol (140 mg, 1.9 mmol) and K$_2$CO$_3$ (788 mg, 5.7 mmol). After 3 h, the mixture was concentrated under reduced pressure. The resulting residue was dissolved in DCM (75 mL) and was washed with water (2×25 mL) and brine (25 mL). The organic phase was dried over Na$_2$SO$_4$, filtered and concentrated under reduced pressure, which generated (69) (370 mg, 91% yield) as an orange solid. This material was used in the next step without further purification.

Preparation of 3-(2-amino-3-fluoroanilino)propan-1-ol, (70). To a solution of 3-(3-fluoro-2-nitroanilino)propan-1-ol (69) (370 mg, 1.6 mmol) in EtOH (10 mL) was added 10% Pd/C (35 mg). The reaction mixture was charged with H$_2$ gas before it was degassed 3 times. The reaction mixture was stirred for 4 h under a H$_2$ atmosphere (balloon). The mixture was then filtered through a pad of Celite®. The filtrate was concentrated under reduced pressure and dried which provided (70) (300 mg, 99% yield) as a white solid. This material was used in the next step without further purification.

Preparation of 5-fluoro-1-(3-hydroxypropyl)-1,4-dihydroquinoxaline-2,3-dione, 30. To a solution of 3-(2-amino-3-fluoroanilino)propan-1-ol (70) (300 mg, 1.6 mmol) in DCM (20 mL) cooled in an ice bath was added Et$_3$N (1.3 mL, 9.5 mmol), followed by slow addition of ethyl chlorooxoacetate (0.3 mL, 2.9 mmol). The ice bath was then removed. After overnight at ambient temperature, the mixture was concentrated under reduced pressure. The residue was dissolved in MeOH (40 mL) and to this solution was added K$_2$CO$_3$ (150 mg, 1.1 mmol). After 4 h at room temperature, the solid was removed by vacuum filtration and the filtrate was concentrated under reduced pressure. The product was purified by column chromatography on silica gel with a gradient of MeOH/CHCl$_3$, 0 to 20%, which generated 30 (129 mg, 33% yield) as a white solid.

$^1$H NMR (600 MHz, DMSO-d$_6$) δ 12.05 (br s, 1H), 7.28-7.23 (m, 1H), 7.22-7.16 (m, 1H), 7.15-7.07 (m, 1H), 4.66 (t, J=5.3 Hz, 1H), 4.17-4.10 (m, 2H), 3.52 (q, J=6.0 Hz, 2H), 1.82-1.73 (m, 2H). $^{19}$F NMR (565 MHz, DMSO-d$_6$) δ −129.67−−129.69 (m, 1F). LC/MS: Eluent system C (retention time: 4.34 min); ESI-MS 239 [M+H]$^+$.

Compound 31

Synthesis of 5-chloro-1-(3-hydroxypropyl)-1,4-dihydroquinoxaline-2,3-dione, 31

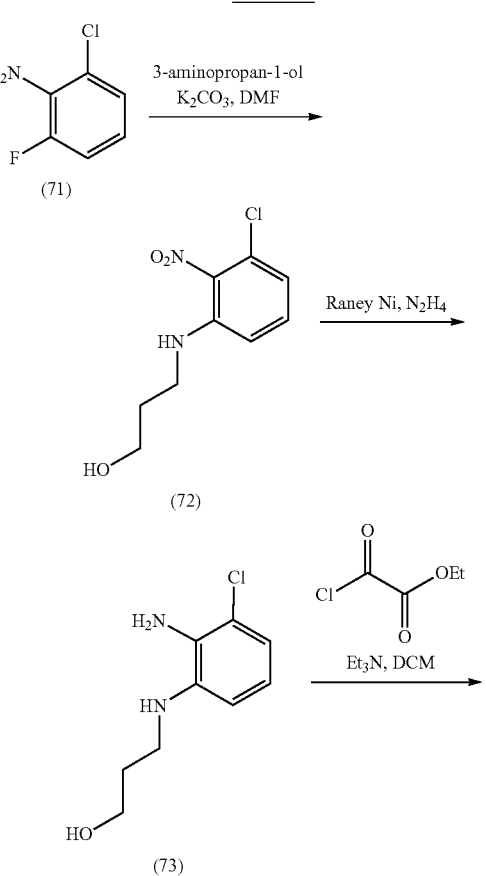

Compound 31 was synthesized as in Scheme 32.

115
-continued

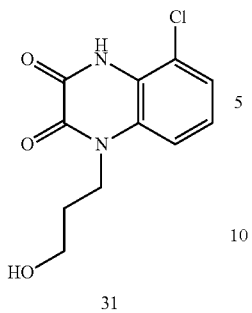
31

116
Compound 32

Synthesis of 6,7-dichloro-1-(3-hydroxypropyl)-1,4-dihydroquinoxaline-2,3-dione, 32

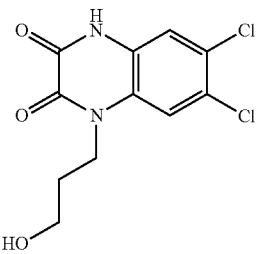
32

Compound 32 was synthesized as in Scheme 33.

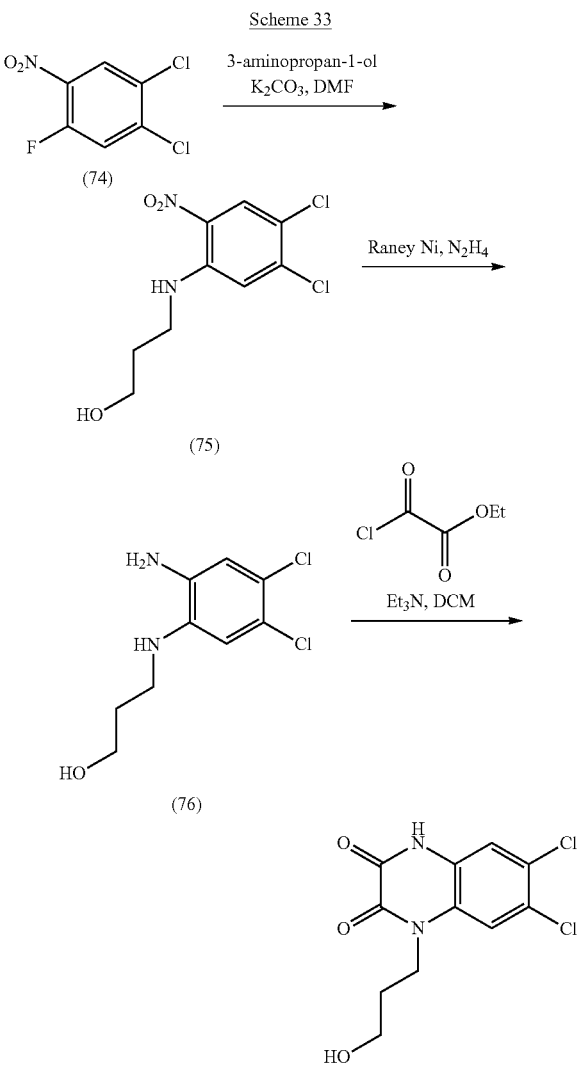

Preparation of 3-(3-chloro-2-nitroanilino)propan-1-ol, (72). To a solution of 1-chloro-3-fluoro-2-nitrobenzene (71) (350 mg, 2.0 mmol) in DMF (10 mL) was added 3-aminopropan-1-ol (225 mg, 3.0 mmol) and $K_2CO_3$ (829 mg, 6.0 mmol). After 3 h, the mixture was concentrated under reduced pressure. The resulting residue was dissolved in DCM (75 mL) and washed with water (2×25 mL) and brine (25 mL). The separated organic phase was dried over $Na_2SO_4$, filtered and concentrated under reduced pressure, which provided (72) (440 mg, 95% yield) as an orange oil and was used in next step without further purification.

Preparation of 3-(2-amino-3-chloroanilino)propan-1-ol, (73). To a solution of 3-(3-chloro-2-nitroanilino)propan-1-ol (72) (220 mg, 0.95 mmol) in MeOH (10 mL) was added $N_2H_4 \cdot H_2O$ (100 mg, 2.0 mmol), followed by Raney Ni (10 mg). The reaction mixture was warmed in a 40° C. oil bath for 1 h. After which, the mixture was filtered through a pad of Celite®. The filtrate was concentrated under reduced pressure which provided (73) (180 mg, 94% yield) as a white solid. It was used in the next step without further purification.

Preparation of 5-chloro-1-(3-hydroxypropyl)-1,4-dihydroquinoxaline-2,3-dione 31. To a solution of 3-(2-amino-3-chloroanilino)propan-1-ol (73) (180 mg, 0.89 mmol) in DCM (15 mL) cooled in an ice bath was added $Et_3N$ (0.6 mL, 1.35 mmol) followed by slow addition of ethyl chlorooxoacetate (0.15 mL, 1.35 mmol). After overnight, the solvent was removed under reduced pressure and the resulting residue was dissolved in MeOH (10 mL). To this solution was added $K_2CO_3$ (100 mg, 0.72 mmol). After 4 h, the solid was removed by filtration and the filtrate was concentrated under reduced pressure. The product was purified by column chromatography on silica gel with a gradient of $MeOH/CHCl_3$, 0 to 20%, which generated 31 (103 mg, 45% yield) as a white solid.

$^1$H NMR (600 MHz, DMSO-$d_6$) δ 11.40 (br s, 1H), 7.43-7.38 (m, 1H), 7.34-7.28 (m, 1H), 7.21 (t, J=8.2 Hz, 1H), 4.66 (t, J=5.1 Hz, 1H), 4.20-4.12 (m, 2H), 3.53 (q, J=6.0 Hz, 2H), 1.85-1.74 (m, 2H). LC/MS: Eluent system C (retention time: 5.62 min); ESI-MS 255 [M+H]$^+$.

Preparation of 3-(4,5-dichloro-2-nitroanilino)propan-1-ol, (75). To a solution of 1,2-dichloro-4-fluoro-5-nitrobenzene (74) (300 mg, 1.4 mmol) in DMF (10 mL) was added 3-aminopropan-1-ol (161 mg, 2.1 mmol) and K$_2$CO$_3$ (580 mg, 4.2 mmol). After 3 h, the solvent was removed under reduced pressure. The residue was dissolved in DCM (75 mL) and washed with water (2×25 mL) and brine (25 mL). The organic phase was dried over Na$_2$SO$_4$, filtered and concentrated under reduced pressure. This provided the product (75) (350 mg, 94% yield) as an orange solid and it was used in the next step without further purification.

Preparation of 3-(2-amino-4,5-dichloroanilino)propan-1-ol (76). To a solution of 3-(4,5-dichloro-2-nitroanilino)propan-1-ol (75) (200 mg, 0.75 mmol) in MeOH (10 mL) was added hydrazine·hydrate (100 mg, 2.0 mmol), followed by Raney Ni (10 mg). The resulting mixture was warmed in an oil bath at 40° C. for 1 h. After which the mixture was filtered through a pad of Celite®. The filtrate was concentrated under reduced pressure, which provided (76) (170 mg, 96% yield) as an off-white solid. It was used in the next step without further purification.

Preparation of 6,7-dichloro-1-(3-hydroxypropyl)-1,4-dihydroquinoxaline-2,3-dione, 32. To a solution of 3-(2-amino-4,5-dichloroanilino)propan-1-ol (76) (170 mg, 0.72 mmol) in DCM (15 mL) cooled in an ice-bath was added Et$_3$N (0.5 mL, 3.6 mmol), followed by slow addition of ethyl chlorooxoacetate (0.12 mL, 1.08 mmol). The ice bath was removed. After overnight at room temperature, the mixture was concentrated under reduced pressure and the residue was dissolved in MeOH (10 mL) and K$_2$CO$_3$ (100 mg, 0.72 mmol) was added. After 4 h, the mixture was filtered and the filtrate was concentrated under reduced pressure. The product was purified by column chromatography on silica gel with a gradient of MeOH/CHCl$_3$, 0 to 20%, which generated 32 (25 mg, 12% yield) as a white solid.

$^1$H NMR (600 MHz, DMSO-d$_6$) δ 12.14 (br s, 1H), 7.68 (s, 1H), 7.31 (s, 1H), 4.67 (t, J=5.1 Hz, 1H), 4.13-4.09 (m, 2H), 3.51 (q, J=6.0 Hz, 2H), 1.80-1.72 (m, 2H). LC/MS: Eluent system C (retention time: 7.75 min); ESI-MS 289 [M+H]$^+$.

Compound 33

Synthesis of 6-chloro-1-(3-hydroxypropyl)-1,4-dihydroquinoxaline-2,3-dione, 33

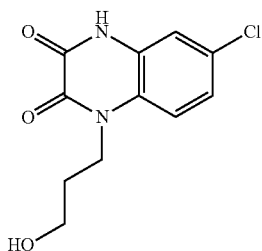

33

Compound 33 was synthesized as in Scheme 34.

Scheme 34

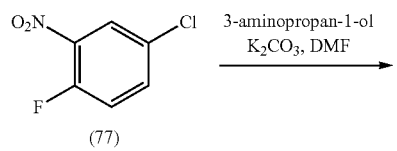

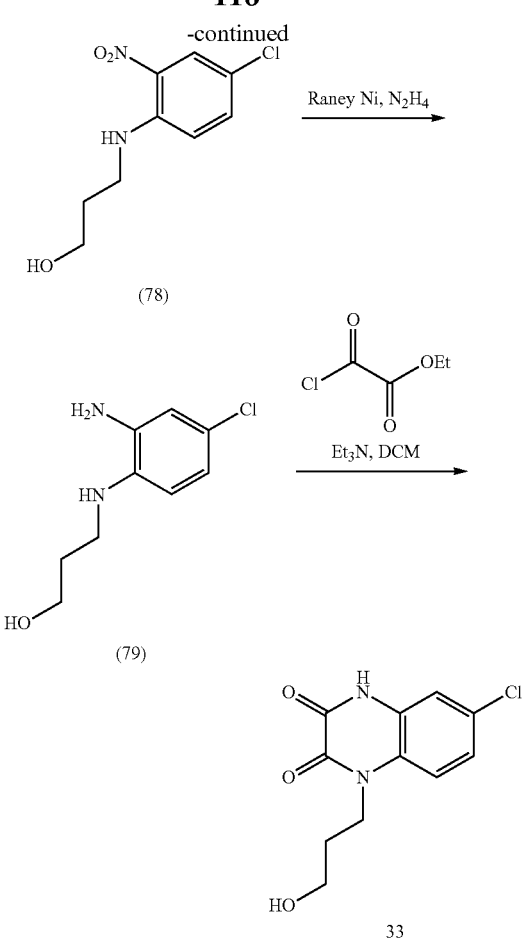

Preparation of 3-(4-chloro-2-nitroanilino)propan-1-ol (78). To a solution of 4-chloro-1-fluoro-2-nitrobenzene (77) (350 mg, 2.0 mmol) in DMF (10 mL) was added 3-aminopropan-1-ol (225 mg, 3.0 mmol) and K$_2$CO$_3$ (829 mg, 6.0 mmol). After 3 h, the solvent was removed under reduced pressure. The resulting residue was dissolved in DCM (75 mL) and the mixture was washed with water (2×25 mL) and brine (25 mL). The separated organic phase was dried over Na$_2$SO$_4$, filtered and concentrated under reduced pressure, which provided (23) (310 mg, 67% yield) as an orange solid and it was used in the next step without further purification.

Preparation of 3-(2-amino-4-chloroanilino)propan-1-ol (79). To a solution of 3-(4-chloro-2-nitroanilino)propan-1-ol (78) (200 mg, 0.87 mmol) in MeOH (10 mL) was added N$_2$H$_4$·H$_2$O (100 mg, 2.0 mmol), followed by Raney Ni (10 mg). The reaction mixture was warmed in an oil bath at 40° C. for 1 h. The mixture was then filtered through a pad of Celite®. The filtrate was concentrated under reduced pressure, which provided (79) (165 mg, 95% yield) as an off-white solid. It was used in next step without further purification.

Preparation of 6-chloro-1-(3-hydroxypropyl)-1,4-dihydroquinoxaline-2,3-dione 33. To a solution of 3-(2-amino-4-chloroanilino)propan-1-ol (79) (165 mg, 0.82 mmol) in DCM (15 mL) cooled in an ice-bath was added Et$_3$N (0.57 mL, 4.1 mmol), followed by slow addition of ethyl chlorooxoacetate (15) (0.14 mL, 1.23 mmol). The ice bath was then removed. After overnight at ambient temperature, the mixture was concentrated under reduced pressure and the resulting residue was dissolved in MeOH (10 mL) and $K_2CO_3$ (100 mg, 0.72 mmol) was added. After 4 h, the mixture was filtered and the filtrate was concentrated under reduced pressure. The product was purified by column chromatography on silica gel with a gradient of MeOH/$CHCl_3$, 0 to 20%, which generated 33 (18 mg, 9% yield) as a white solid.

$^1$H NMR (600 MHz, DMSO-$d_6$) δ 12.10 (s, 1H), 7.42 (d, J=8.7 Hz, 1H), 7.24 (dd, J=2.4, 8.8 Hz, 1H), 7.20 (d, J=2.4 Hz, 1H), 4.66 (t, J=5.1 Hz, 1H), 4.17-4.08 (m, 2H), 3.55-3.48 (m, 2H), 1.82-1.70 (m, 2H). LC/MS: Eluent system C (retention time: 6.29 min); ESI-MS 255 [M+H]$^+$.

Compound 34

Synthesis of 1-(3-hydroxypropyl)-6-(trifluoromethyl)-1,4-dihydroquinoxaline-2,3-dione, 34

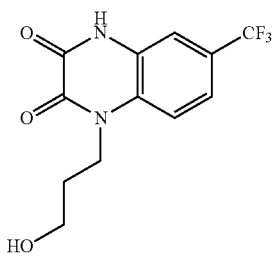

34

Compound 34 was synthesized as in scheme 35

Scheme 35

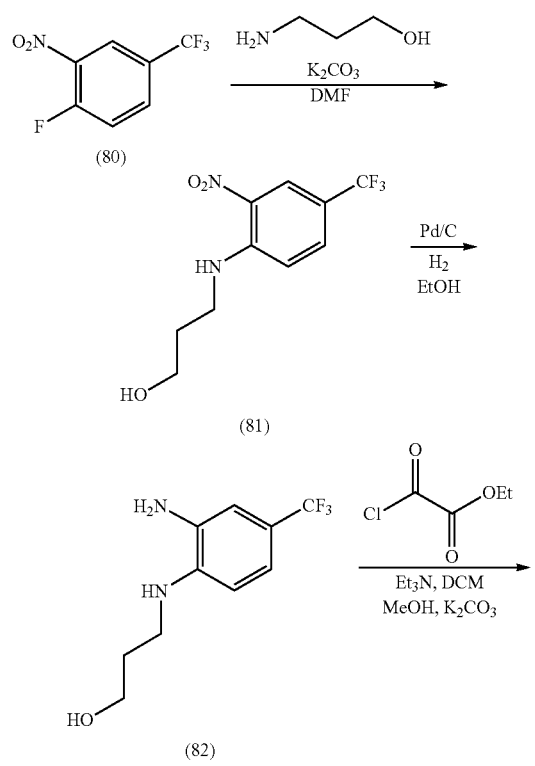

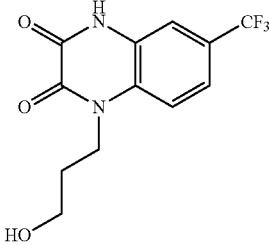

34

Preparation of 3-[2-nitro-4-(trifluoromethyl)anilino]propan-1-ol, (81). A mixture of 1-fluoro-2-nitro-4-(trifluoromethyl)benzene (80) (500.0 mg, 2.39 mmol), 3-aminopropan-1-ol (360 mg, 4.78 mmol) and $K_2CO_3$ (991 mg, 7.17 mmol) in N,N-dimethyl formamide (10 mL) was stirred overnight at room temperature. Then 25 mL water was added and the mixture was extracted with $CHCl_3$ (3×25 mL). The combined organic layer was washed with saturated brine solution (1×25 mL), dried over anhydrous $Na_2SO_4$, filtered, and concentrated under reduced pressure, which generated (81) (620 mg, 98% yield) as a yellow color liquid. This material was used in the next step without further purification.

Preparation of 3-[2-amino-4-(trifluoromethyl)anilino]propan-1-ol, (82). To a solution of 3-[2-nitro-4-(trifluoromethyl)anilino]propan-1-ol (81) (620.0 mg, 2.35 mmol) in absolute ethanol (10 mL) was added 10% Pd/C (60 mg). A balloon filled with hydrogen gas was attached onto the round-bottomed flask. After overnight, the mixture was filtered through a bed of Celite® and the bed was washed with ethanol (2×10 mL). Concentration of combined filtrates under reduced pressure produced (82) (540 mg, 98% yield) as a pale brown color solid.

Preparation of 1-(3-hydroxypropyl)-6-(trifluoromethyl)-1,4-dihydroquinoxaline-2,3-dione, 34. To a solution of 3-[2-amino-4-(trifluoromethyl)anilino]propan-1-ol (82) (320.0 mg, 1.37 mmol) and $Et_3N$ (0.95 mL, 6.83 mmol) in DCM (10.0 mL), was added ethyl chlorooxoacetate (280.0 mg, 2.05 mmol) dropwise. After overnight at room temperature, the mixture was concentrated under reduced pressure. To the residue was added MeOH (10 mL) and $K_2CO_3$ (2.0 g, 14.47 mmol). After 24 h, the mixture was vacuum filtered and the collected solid was washed $CHCl_3$:MeOH (9:1, 3×10 mL). The combined filtrates were concentrated under reduced pressure. The residue was adsorbed on silica gel (5 g) using $CHCl_3$:MeOH (90:10, 10 mL) and the product was purified by column chromatography on silica gel (Biotage®, 12 g silicycle column, eluted with gradient of 0% to 20% MeOH in $CHCl_3$), which afforded 34 (108.4 mg, 28% yield) as an off-white solid.

$^1$H NMR (600 MHz, DMSO-$d_6$) δ 12.03 (brs, 1H), 7.60 (d, J=8.8 Hz, 1H), 7.52 (dd, J=1.6, 8.8 Hz, 1H), 7.48 (s, 1H), 4.67 (t, J=5.1 Hz, 1H), 4.18-4.15 (m, 2H), 3.52 (q, J=6.0 Hz, 2H), 1.82-1.75 (m, 2H). $^{19}$F NMR (565 MHz, DMSO-$d_6$) δ −60.45 (s, 3F). LC/MS: Eluent system A (retention time: 5.73 min); ESI-MS: 289 [M+H]$^+$.

Compound 35

Synthesis of 1-(3-hydroxypropyl)-7-(trifluoromethyl)-1,4-dihydroquinoxaline-2,3-dione, 35

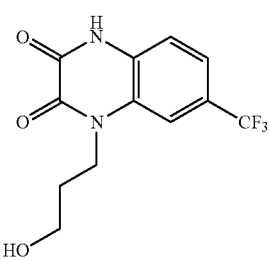

Compound 35 was synthesized as in scheme 36.

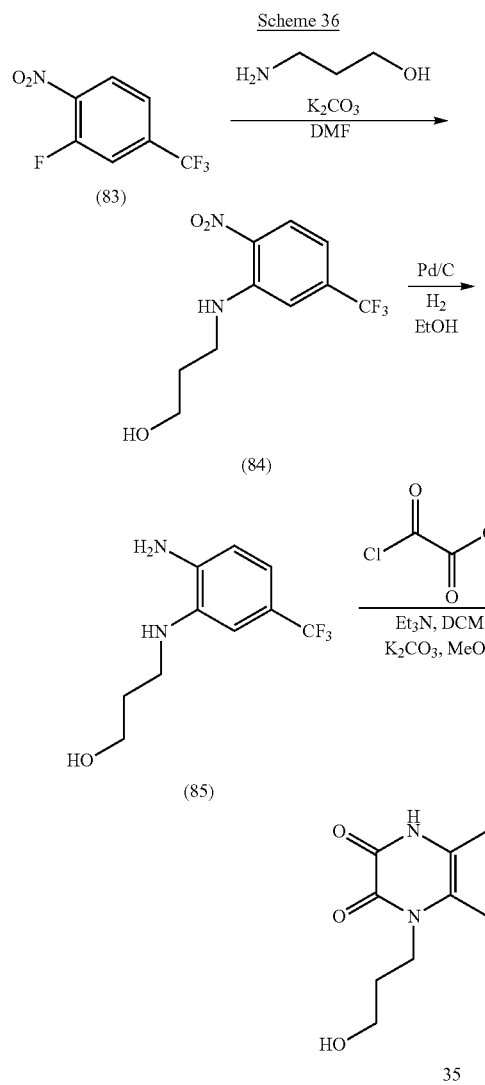

Preparation of 3-[2-nitro-5-(trifluoromethyl)anilino]propan-1-ol (84). Following a similar procedure as described for (81) in Scheme 35 with 2-fluoro-1-nitro-4-(trifluoromethyl)benzene (83) (500 mg, 2.39 mmol), 3-aminopropan-1-ol (360 mg, 4.78 mmol) and $K_2CO_3$ (991 mg, 7.17 mmol) in N,N-dimethylformamide (10 mL), afforded (84) (595 mg, 94% yield) as a yellow color solid. This material was used in the next step without further purification.

Preparation of 3-[2-amino-5-(trifluoromethyl)anilino]propan-1-ol (85). Following a similar procedure as described for (82) in Scheme 35 with 3-[2-nitro-5-(trifluoromethyl)anilino]propan-1-ol (84) (595 mg, 2.25 mmol), absolute ethanol (10 mL), and 10% Pd/C (60 mg), afforded (85) (480 mg, 91% yield) as a pale brown color solid.

Preparation of 1-(3-hydroxypropyl)-6-(trifluoromethyl)-1,4-dihydroquinoxaline-2,3-dione, 35. Following a similar procedure as described for 34 in Scheme 35 with 3-[2-amino-5-(trifluoromethyl)anilino]propan-1-ol (85) (330 mg, 1.41 mmol), $Et_3N$ (0.98 mL, 7.05 mmol), ethyl chlorooxoacetate (290 mg, 2.11 mmol) in DCM (10 mL), followed by MeOH (10.0 mL) and $K_2CO_3$ (2.0 g, 14.47 mmol). The resulting residue was adsorbed on silica gel (5 g) using $CHCl_3$:MeOH (90:10, 10 mL) and the product purified by column chromatography on silica gel (Biotage®, 12 g silicycle column, eluted with gradient of 0% to 20% MeOH in $CHCl_3$), which afforded 35 (136.1 mg, 34% yield) as an off-white solid.

$^1$H NMR (600 MHz, DMSO-$d_6$) δ 12.30 (brs, 1H), 7.70 (s, 1H), 7.53 (dd, J=1.0, 8.4 Hz, 1H), 7.34 (d, J=8.3 Hz, 1H), 4.71 (t, J=4.5 Hz, 1H), 4.20-4.17 (m, 2H), 3.51 (q, J=5.8 Hz, 2H), 1.82-1.74 (m, 2H). $^{19}$F NMR (565 MHz, DMSO-$d_6$) δ −59.9 (s, 3F). LC/MS: Eluent system A retention time: 5.65 min); ESI-MS: 289 [M+H]$^+$.

Compound 36

Synthesis of 7-chloro-6-fluoro-1-(3-hydroxypropyl)-1,4-dihydroquinoxaline-2,3-dione, 36

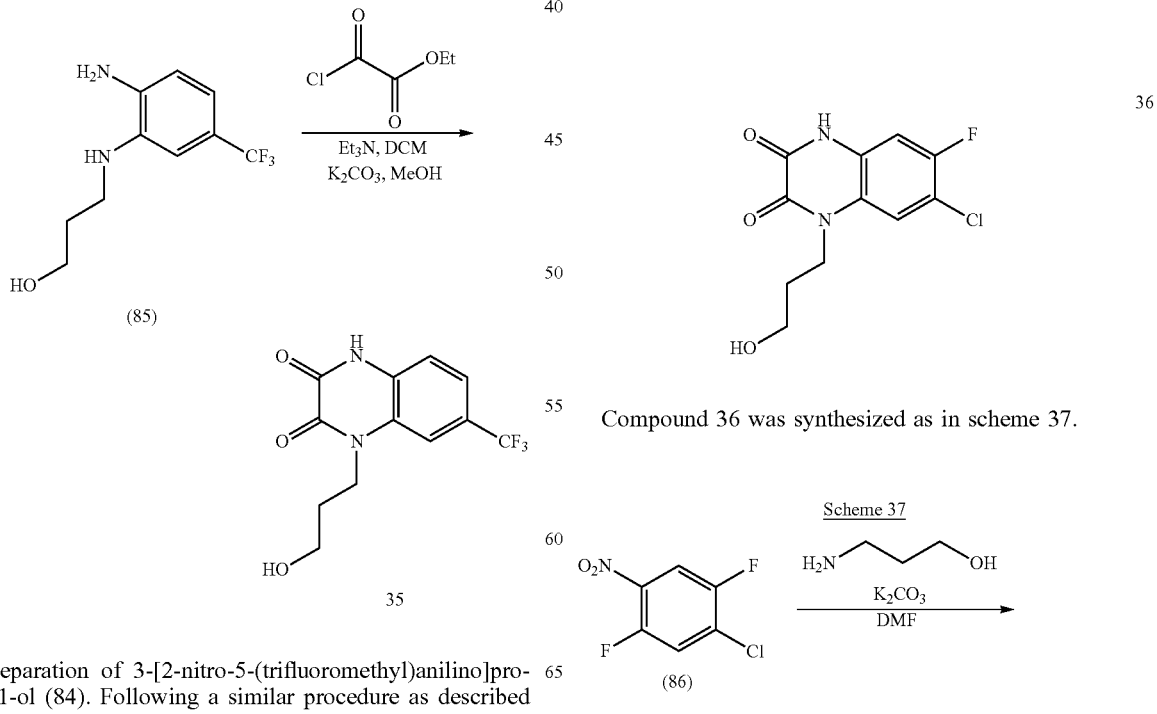

Compound 36 was synthesized as in scheme 37.

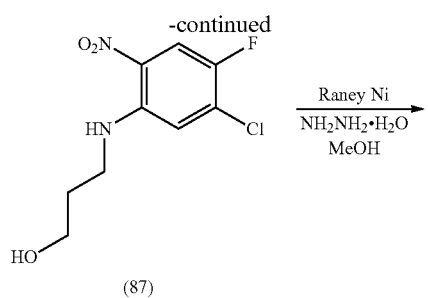

(87)

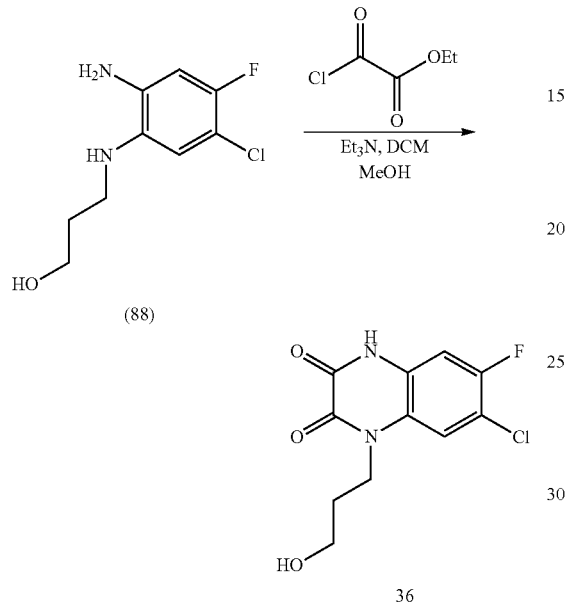

Preparation of 3-(5-chloro-4-fluoro-2-nitroanilino)propan-1-ol (87). Following a similar procedure as described for (81) in Scheme 35 with 1-chloro-2,5-difluoro-4-nitrobenzene (86) (500 mg, 2.58 mmol), 3-aminopropan-1-ol (388 mg, 5.17 mmol), and K$_2$CO$_3$ (1.07 g, 7.75 mmol) in N,N-dimethylformamide (10 mL) produced (87) (620 mg, 97% yield) as a yellow solid. This material was used in the next step without further purification.

Preparation of 3-(2-amino-5-chloro-4-fluoroanilino)propan-1-ol (88). To a solution of 3-(5-chloro-4-fluoro-2-nitroanilino)propan-1-ol (87) (200 mg, 0.80 mmol) in methanol (10 mL) was added Raney nickel (20 mg) and hydrazine hydrate (1.0 mL). After effervescences stopped at room temperature, a water condenser was attached and the mixture was heated to reflux in an oil bath. After 1 h, the reaction mixture was cooled to room temperature and filtered through a bed of Celite® and the Celite® bed was washed with methanol (2×10 mL). The combined filtrates were concentrated under reduced pressure, which generated (88) (175.9 mg, quantitative yield) as a pale brown color solid. This material was used in the next step without further purification.

Preparation of 7-chloro-6-fluoro-1-(3-hydroxypropyl)-1,4-dihydroquinoxaline-2,3-dione, 36. Following a similar procedure as described for 34 in Scheme 35 with 3-(2-amino-5-chloro-4-fluoroanilino)propan-1-ol (88) (175.9 mg, 0.80 mmol), Et$_3$N (0.56 mL, 4.02 mmol), and ethyl chlorooxoacetate (164.8 mg, 1.21 mmol) in DCM (10 mL), followed by MeOH (10 mL) and K$_2$CO$_3$ (2.0 g, 14.47 mmol). The resulting mixture was adsorbed on silica gel (5 g) using CHCl$_3$:MeOH (90:10, 10 mL) and the product purified by column chromatography on silica gel (Biotage®, 12 g silicycle column, eluted with gradient of 0 to 20% MeOH in CHCl$_3$), which afforded 36 (76.3 mg, 35% yield) as a yellowish brown solid.

$^1$H NMR (600 MHz, DMSO-d$_6$) δ 12.10 (brs, 1H), 7.63 (d, J=6.8 Hz, 1H), 7.14 (d, J=9.6 Hz, 1H), 4.68 (t, J=4.9 Hz, 1H), 4.12-4.10 (m, 2H), 3.51 (q, J=5.7 Hz, 2H), 1.80-1.73 (m, 2H). $^{19}$F NMR (565 MHz, DMSO-d$_6$) δ -122.5 (s, 1F). LC/MS: Eluent system A (retention time: 5.15 min); ESI-MS: 273 [M+H]$^+$.

Compounds 37 and 38

Synthesis of 4-(2-hydroxycyclopentanecarbonyl)-3,4-dihydroquinoxalin-2(1H)-one, 37 and 38

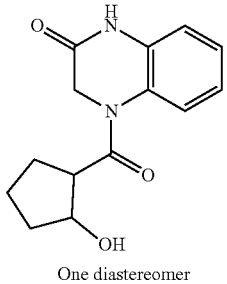

One diastereomer

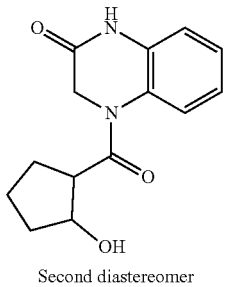

Second diastereomer

Compounds 37 and 38 were synthesized as in Scheme 38.

Scheme 38

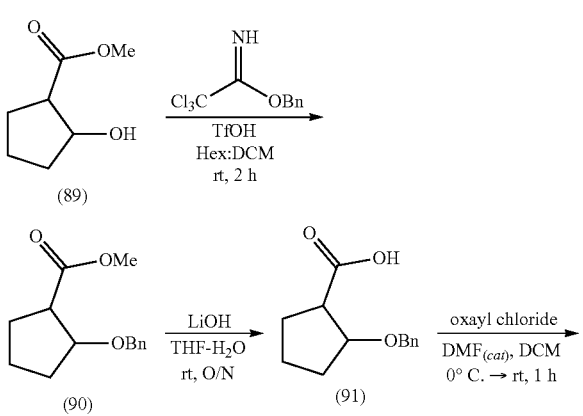

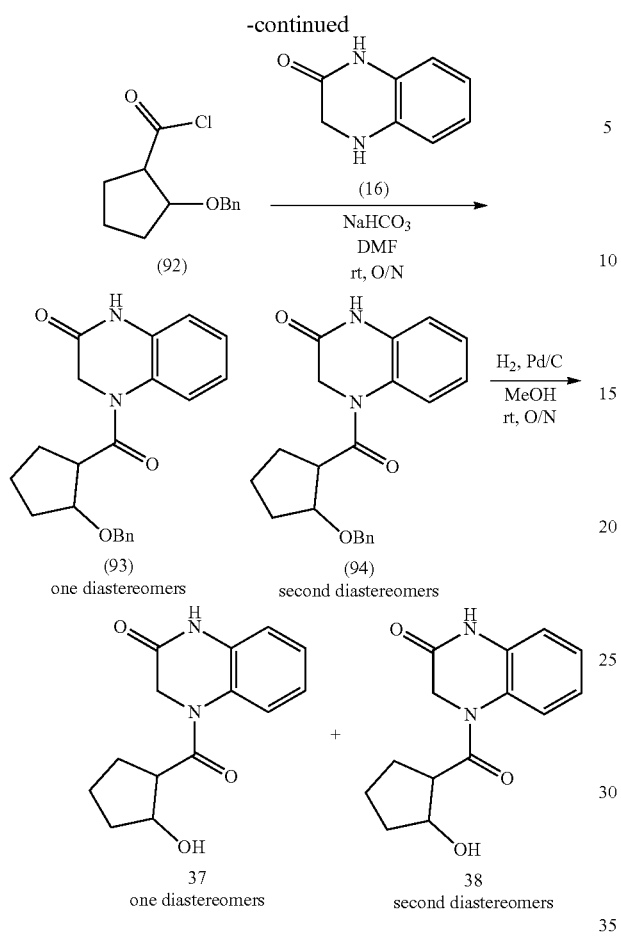

Preparation of methyl 2-(benzyloxy)cyclopentanecarboxylate, (90). Benzylation of methyl 2-hydroxycyclopentanecarboxylate (89) (0.5 g, 3.47 mmol) in the presence of benzyl-2,2,2-trichloroacetamidate (2.3 g, 9.1 mmol) and trifluoromethanesulfonic acid (0.2 g, 1.3 mmol) was accomplished by following a similar procedure to that for (37) in Scheme 23, which provided (90) (2.81 g).

Preparation of 2-(benzyloxy)cyclopentanecarboxylic acid (91). Saponification of the crude methyl 2-(benzyloxy) cyclopentanecarboxylate (90) (2.81 g) following a similar procedure as for (38) in Scheme 23, which provided after purification by silica gel column chromatography (elute with gradient of 0%→100% ethyl acetate in hexanes) compound (91) (1.7 g) as a colorless oil. This was used in the next step without further purification.

Preparation of 2-(benzyloxy)cyclopentanecarbonyl chloride, (92). Following the procedure for (15) in Scheme 19 with 2-(benzyloxy)cyclopentanecarboxylic acid (91) (0.6 g, maximum 1.2 mmol) provided (92) along with molecular sieves powder.

Preparation of 4-(2-(benzyloxy)cyclopentanecarbonyl)-3, 4-dihydroquinoxalin-2(1H)-one, (93) and (94). Following the procedure for (29) in Scheme 19 with 2-(benzyloxy) cyclopentanecarbonyl chloride (92) (0.6 g, maximum 1.2 mmol) and 3,4-dihydro-1H-quinoxalin-2-one (16) (160 mg, 1.09 mmol), provided after purification by silica gel column chromatography (eluted with gradient of 20%→80% ethyl acetate in hexanes) two fractions containing enriched (>80% de) diastereomers (93) (98 mg, 26% yield) and (94) (30 mg, 8% yield).

Preparation of diastereomers of 4-(2-hydroxycyclopentanecarbonyl)-3,4-dihydroquinoxalin-2(1H)-one 37 and 38. Two diastereomers of 4-(2-(benzyloxy)cyclopentanecarbonyl)-3,4-dihydroquinoxalin-2(1H)-one (93) (98 mg, 0.28 mmol) and (94) (30 mg, 0.08 mmol) were treated separately as described for 15 in Scheme 19. Purification of the separate samples by silica gel column chromatography (eluent ethyl acetate-methanol 0%→4%) provided 37 (60 mg, 82% yield) and 38 (14 mg, 67% yield), both as white powders.

For Compound 37:
$^1$H NMR (600 MHz, DMSO-d6) δ 10.68 (s, 1H), 7.47 (br s, 1H), 7.21 (s, 1H), 7.09-6.99 (m, 2H), 4.97 (d, J=5.0 Hz, 1H), 4.40-4.30 (m, 2H), 4.23 (quintet, J=5.6 Hz, 1H), 3.17 (d, J=5.3 Hz, 2H), 3.09-3.04 (m, 1H), 1.90-1.80 (m, 2H), 1.66-1.58 (m, 2H). LC/MS: Eluent system C (retention time: 6.74 min); ESI-MS 261 [M+H]$^+$.

For Compound 38:
$^1$H NMR (600 MHz, DMSO-d6) δ 10.60 (s, 1H), 7.60 (d, J=7.8 Hz, 1H), 7.17 (br s, 1H), 7.05-6.98 (m, 2H), 4.72 (d, J=4.5 Hz, 1H), 4.33 (br s, 2H), 3.30 (q, J=6.9 Hz, 1H), 2.10 (br s, 1H), 1.77-1.68 (m, 2H), 1.65-1.59 (m, 2H), 1.58-1.52 (m, 1H), 1.43-1.35 (m, 1H). LC/MS: Eluent system C (retention time: 7.02 min); ESI-MS 261 [M+H]$^+$.

Compound 39

Synthesis of 4-oxo-4-(3-oxo-3,4-dihydroquinoxalin-1(2H)-yl)butanenitrile, 39

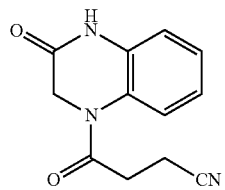

39

Compound 39 was synthesized as in Scheme 39.

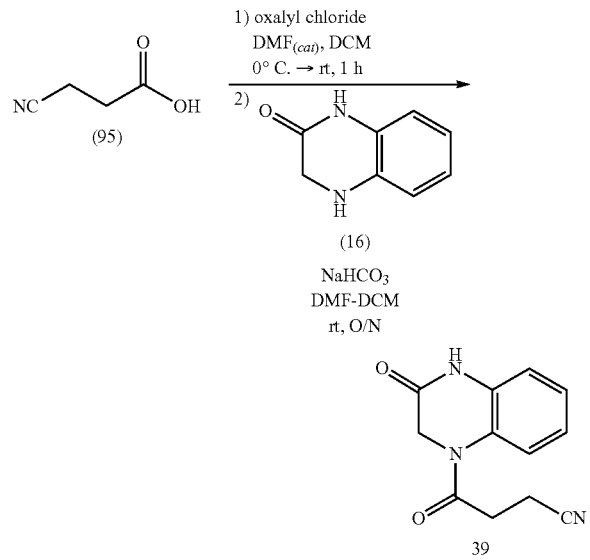

Scheme 39

Preparation of 4-oxo-4-(3-oxo-3,4-dihydroquinoxalin-1 (2H)-yl)butanenitrile, 39. To a solution of 3-cyanopropanoic acid (95) (250 mg, 2.5 mmol) in DCM (6 mL) containing two drops of DMF and powdered molecular sieves (4 Å, 2 g) cooled in an ice bath was added oxalyl chloride (315 mg, 2.5 mmol). After stirring for 30 min the ice bath was removed. After 1 h at ambient temperature, the mixture was diluted with DMF (8 mL) and 3,4-dihydro-1H-quinoxalin-2-one (16) (150 mg, 1.0 mmol) was added, followed by sodium bicarbonate (500 mg, 6 mmol). After overnight at room temperature the mixture was filtered, and to the filtrate was added a few drops of acetic acid and then the mixture was concentrated under reduced pressure. Purification of the product was accomplished by silica gel column chromatography (eluting with a gradient of 25%→100% ethyl acetate in hexanes), which provided 39 (215 mg, 94% yield) as a white powder.

$^1$H NMR (600 MHz, DMSO-d6) δ 10.71 (s, 1H), 7.54 (br s, 1H), 7.23 (br s, 1H), 7.09-7.01 (m, 2H), 4.36 (br s, 2H), 2.91 (br s, 2H), 2.66 (t, J=6.8 Hz, 2H). LC/MS: Eluent system C (retention time: 4.71 min); ESI-MS 230 [M+H]$^+$ and 228 [M–H]$^-$.

Compound 40

3,4-dihydro-4-(4-hydroxy-1-oxobutyl)-2(1H)-quinoxalinone, 40

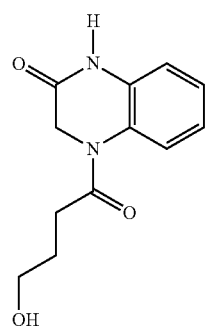

40

Compound 3,4-dihydro-4-(4-hydroxy-1-oxobutyl)-2 (1H)-quinoxalinone, 40 is commercially available (CAS #1512680-56-6) or it can be generated by one skilled in the art using chemistry similar to that reported herein.

Compound 41

Synthesis of 3-(2,3-dioxo-3,4-dihydroquinoxalin-1 (2H)-yl)propyl 2-methylpropanoate, 41

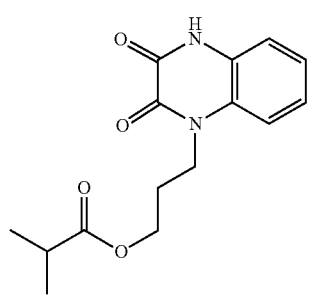

41

Compound 41 was synthesized as in Scheme 40.

Scheme 40

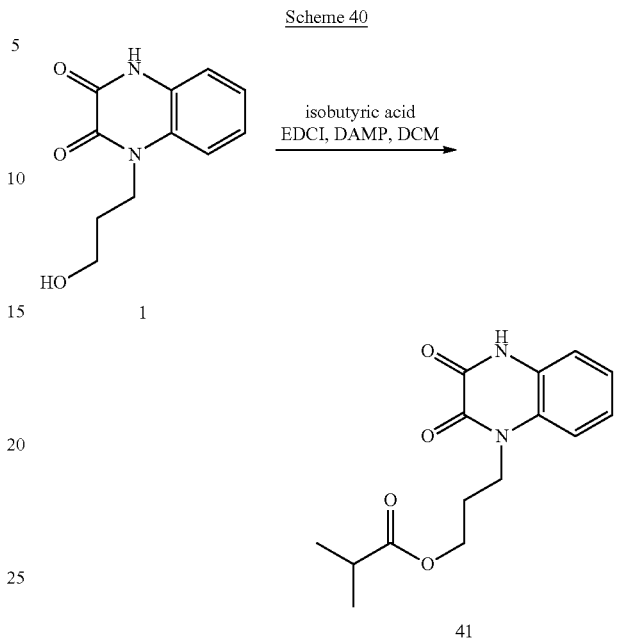

Preparation of 3-(2,3-dioxo-3,4-dihydroquinoxalin-1 (2H)-yl)propyl 2-methylpropanoate, 41. To a solution of 1-(3-hydroxypropyl)-1,4-dihydroquinoxaline-2,3-dione 1 (75 mg, 0.34 mmol) and isobutyric acid (0.046 mL, 0.51 mmol) in DCM (8 mL) was added EDCI (104 mg, 0.54 mmol) and DMAP (125 mg, 1.02 mmol). After overnight, the mixture was diluted with DCM (15 mL) and water (5 mL). The two layers were separated, and the organic phase was washed with brine (10 mL), dried over Na$_2$SO$_4$, filtered and concentrated under reduced pressure. The product was purified by column chromatography on silica gel with a gradient of EtOAc/hexanes, 50 to 100%, which generated 41 (54 mg, 55% yield) as a white solid.

$^1$H NMR (600 MHz, CDCl$_3$) δ 10.89-10.61 (br.s, 1H), 7.40-7.21 (m, 4H), 4.40-4.31 (m, 2H), 4.25 (t, J=6.0 Hz, 2H), 2.62 (t, J=7.0 Hz, 1H), 2.20-2.13 (m, 2H), 1.24 (d, J=7.0 Hz, 6H). LC/MS: Eluent system A (retention time: 6.78 min); ESI-MS 291 [M+H]$^+$.

Compound 42

Synthesis of 3-(2,3-dioxo-3,4-dihydroquinoxalin-1 (2H)-yl)propyl L-valinate hydrochloride salt, 42

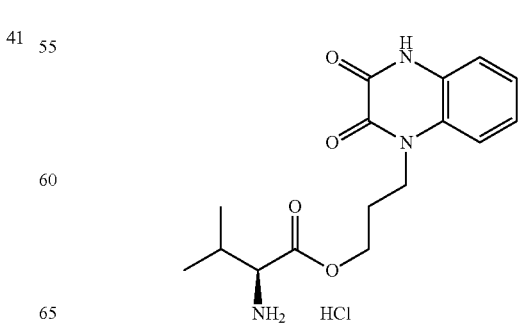

42

Compound 42 was synthesized as in Scheme 41.

Scheme 41

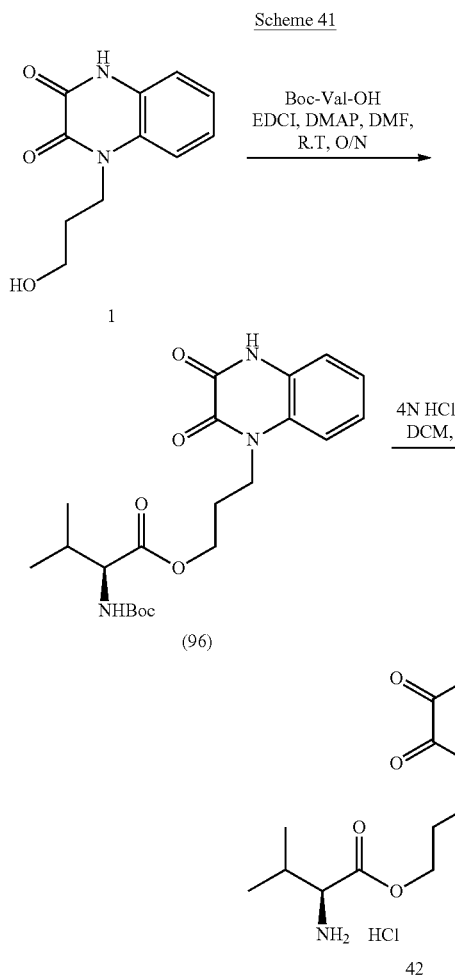

Preparation of 3-(2,3-dioxo-3,4-dihydroquinoxalin-1(2H)-yl)propyl N-(tert-butoxycarbonyl)-L-valinate (96). To a solution of 1-(3-hydroxypropyl)-1,4-dihydroquinoxaline-2,3-dione 1 (75 mg, 0.34 mmol) and (S)-2-(Boc-amino)-3-methylbutyric acid (Boc-Val-OH) (81 mg, 0.37 mmol) in DMF was added EDCI (98 mg, 0.51 mmol) and DMAP (1 mg). After 24 h, more DMAP (42 mg, 0.34 mmol) was added and after an additional 24 h the reaction mixture was then diluted with DCM (30 mL) and the mixture was washed with water (3×5 mL) and brine (10 mL). The organic phase was dried over Na$_2$SO$_4$, filtered and concentrated under reduced pressure. The product was purified by column chromatography on silica gel with a gradient of MeOH/CHCl$_3$, 0 to 5%, which generated (96) (80 mg, 56% yield) as a white solid.

Preparation of 3-(2,3-dioxo-3,4-dihydroquinoxalin-1(2H)-yl)propyl L-valinate hydrochloride salt, 42. To a solution of 3-(2,3-dioxo-3,4-dihydroquinoxalin-1(2H)-yl)propyl N-(tert-butoxycarbonyl)-L-valinate (96) (80 mg, 0.19 mmol) in DCM (3 mL) was added 4N HCl solution in dioxane (2 mL, 8 mmol). After overnight, the mixture was concentrated under reduced pressure and the residue was co-evaporated with DCM/CH$_3$CN (1:1, 2×10 mL). The solid was collected by filtration and dried, which provided 42 (60 mg, 89% yield) as a white solid.

$^1$H NMR (600 MHz, DMSO-d$_6$) δ 12.06 (br s, 1H), 8.32 (br s, 3H), 7.45-7.41 (m, 1H), 7.25-7.14 (m, 3H), 4.37-4.31 (m, 1H), 4.29-4.18 (m, 3H), 3.93 (d, J=4.5 Hz, 1H), 2.21-2.11 (m, 1H), 2.06-1.96 (m, 2H), 1.01 (d, J=7.0 Hz, 3H), 0.98 (d, J=6.9 Hz, 3H). LC/MS: Eluent system A (retention time: 4.09 min); ESI-MS 320 [M+H]$^+$.

Compound 43

Synthesis of propan-2-yl 4-(3-hydroxypropyl)-2,3-dioxo-3,4-dihydroquinoxaline-1(2H)-carboxylate, 43

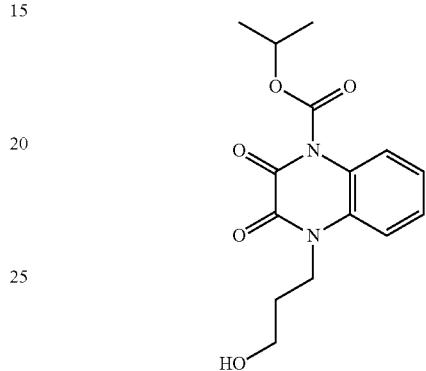

Compound 43 was synthesized as in Scheme 42.

Scheme 42

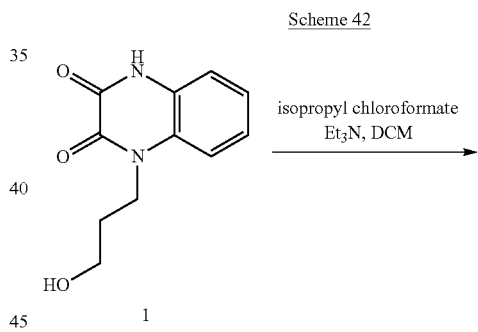

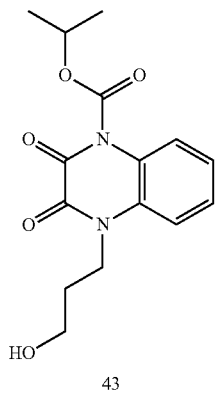

Preparation of propan-2-yl 4-(3-hydroxypropyl)-2,3-dioxo-3,4-dihydroquinoxaline-1(2H)-carboxylate 43. To a solution of 1-(3-hydroxypropyl)-1,4-dihydroquinoxaline-2,3-dione 1 (75 mg, 0.34 mmol) in DCM (5 mL) cooled in an ice-bath was added Et$_3$N (0.14 mL, 1.02 mmol), followed by isopropyl chloroformate (0.37 mL, 0.37 mmol). The ice bath was then removed. After 3 days at ambient temperature, the reaction mixture was diluted with DCM (15 mL) and water (10 mL) was added. The two layers were separated. The aqueous layer was extracted with DCM (2×15 mL). The combined organic phase was washed with brine, dried over $Na_2SO_4$, filtered and concentrated under reduced pressure. The product was purified by column chromatography on silica gel with a gradient of MeOH/CHCl$_3$, 0 to 10%, which generated 43 (29 mg, 28% yield) as a white solid.

$^1$H NMR (600 MHz, CDCl$_3$) δ 7.86 (dd, J=1.5, 7.9 Hz, 1H), 7.64 (ddd, J=1.5, 7.2, 8.6 Hz, 1H), 7.51-7.42 (m, 2H), 5.07 (spt, J=6.3 Hz, 1H), 4.52 (t, J=6.4 Hz, 2H), 3.66-3.56 (m, 2H), 2.98 (t, J=6.6 Hz, 1H), 2.13-2.03 (m, 2H), 1.44 (d, J=6.3 Hz, 6H). LC/MS: Eluent system A (retention time: 7.17 min).

Compound 44 and 45

Synthesis of [4-(3-hydroxypropyl)-2,3-dioxo-3,4-dihydroquinoxalin-1(2H)-yl]methyl methyl carbonate, 44 and {[4-(3-hydroxypropyl)-3-oxo-3,4-dihydroquinoxalin-2-yl]oxy}methyl methyl carbonate, 45

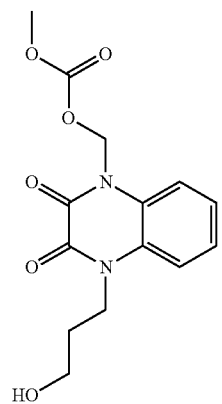

44

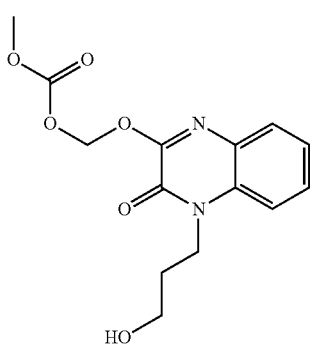

45

Compounds 44 and 45 were synthesized as in Scheme 43.

Scheme 43

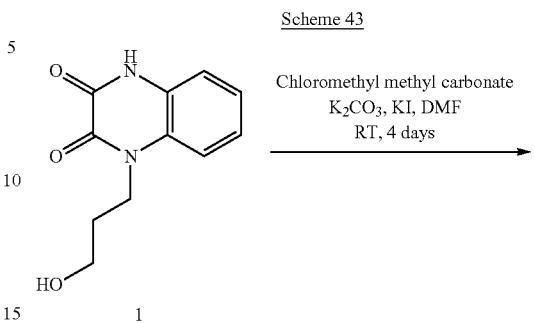

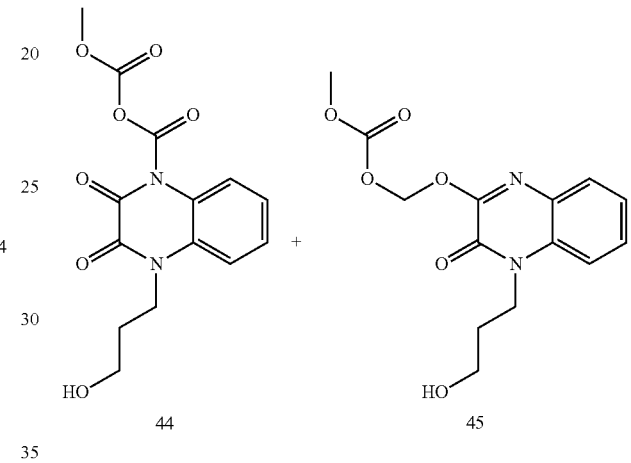

Preparation of [4-(3-hydroxypropyl)-2,3-dioxo-3,4-dihydroquinoxalin-1(2H)-yl]methyl methyl carbonate, 14 and {[4-(3-hydroxypropyl)-3-oxo-3,4-dihydroquinoxalin-2-yl]oxy}methyl methyl carbonate, 15. To a solution of 1-(3-hydroxypropyl)-1,4-dihydroquinoxaline-2,3-dione 1 (75 mg, 0.34 mmol) in DMF (5 mL) was added chloromethyl methyl carbonate (64 mg, 0.51 mmol), $K_2CO_3$ (94 mg, 0.68 mmol) and KI (56 mg, 0.34 mmol). After 48 h, another portion of chloromethyl methyl carbonate (64 mg, 0.51 mmol), $K_2CO_3$ (94 mg, 0.68 mmol) and KI (56 mg, 0.34 mmol) were added. After another 48 h, the mixture was diluted with EtOAc (50 mL) and washed with water (3×10 mL) and brine (10 mL). The organic phase was dried over $Na_2SO_4$, filtered and concentrated under reduced pressure. The products were purified by column chromatography on silica gel with a gradient of MeOH/CHCl$_3$, 0 to 5%, which provided 44 (13 mg, 12% yield) as a white solid and then after continuing to eluent from 5% to 10% MeOH/CHCl$_3$ provided 45 (18 mg, 17% yield) as a white solid.

Compound 44: $^1$H NMR (600 MHz, DMSO-d$_6$) δ 7.65-7.57 (m, 2H), 7.54 (ddd, J=1.5, 7.1, 8.4 Hz, 1H), 7.40-7.33 (m, 1H), 6.10 (s, 2H), 4.68 (t, J=5.3 Hz, 1H), 4.33-4.25 (m, 2H), 3.79 (s, 3H), 3.53 (q, J=5.8 Hz, 2H), 1.84-1.78 (m, 2H). LC/MS: Eluent system A (retention time: 6.42 min); ESI-MS 309 [M+H]$^+$.

Compound 45: $^1$H NMR (600 MHz, DMSO-d$_6$) δ 7.52-7.48 (m, 2H), 7.37-7.26 (m, 1H), 7.31-7.26 (m, 1H), 6.18 (s, 2H), 4.67 (s, 1H), 4.17 (dd, J=6.8, 8.7 Hz, 2H), 3.76 (s, 3H), 3.54 (q, J=6.0 Hz, 2H), 1.85-1.75 (m, 2H) LC/MS: Eluent system A (retention time: 4.96 min); ESI-MS 309 [M+H]$^+$.

Compound 46

Synthesis of 3-(2,3-dioxo-3,4-dihydroquinoxalin-1 (2H)-yl)propyl 2-methylbenzoate, 46

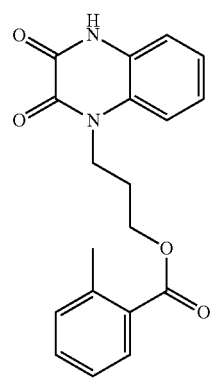

46

Compound 46 was synthesized as in Scheme 44.

Scheme 44

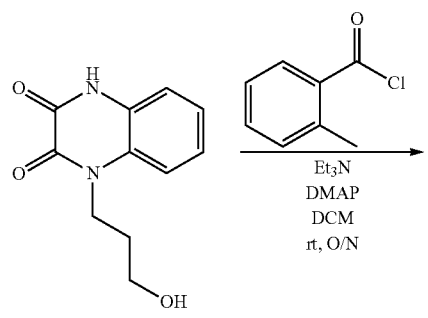

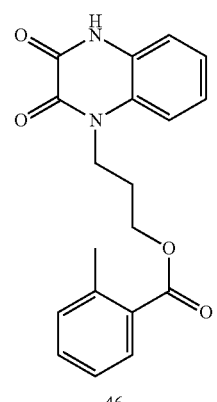

Preparation of 3-(2,3-dioxo-3,4-dihydroquinoxalin-1 (2H)-yl)propyl 2-methylbenzoate, 46. To a stirred suspension of 1-(3-hydroxypropyl)quinoxaline-2,3(1H,4H)-dione 1 (30 mg, 0.13 mmol) in DCM (10 mL) was added 2-methylbenzoyl chloride (50 mg, 0.32 mmol, 2.5 equivalents) followed by triethylamine (100 mg, 0.99 mmol). After overnight, the mixture was concentrated under reduced pressure, then the residue was dissolved in a minimal amount of DCM and loaded on silica column through a silica plug. Purification by column chromatography (eluted with a gradient of 0%→8% methanol in chloroform) provided 46 (14 mg, 32% yield) as white powder.

$^1$H NMR (600 MHz, DMSO-d6) δ 12.01 (s, 1H), 7.79 (dd, J=1.3, 7.8 Hz, 1H), 7.49 (ddd, J=1.5, 7.5, 7.6 Hz, 1H), 7.46-7.43 (m, 1H), 7.33 (d, J=7.7 Hz, 1H), 7.31 (t, J=7.5 Hz, 1H), 7.20-7.15 (m, 3H), 4.34 (t, J=6.0 Hz, 2H), 4.30 (t, J=7.0 Hz, 2H), 2.51 (s, 3H), 2.10 (quintet, J=7.1 Hz, 2H). LC/MS: Eluent system D (retention time: 4.60 min); ESI-MS 339 [M+H]$^+$ and 337 [M–H]$^-$.

Compound 47

Synthesis of 3-(2,3-dioxo-3,4-dihydroquinoxalin-1 (2H)-yl)propyl 4-methylbenzoate, 47

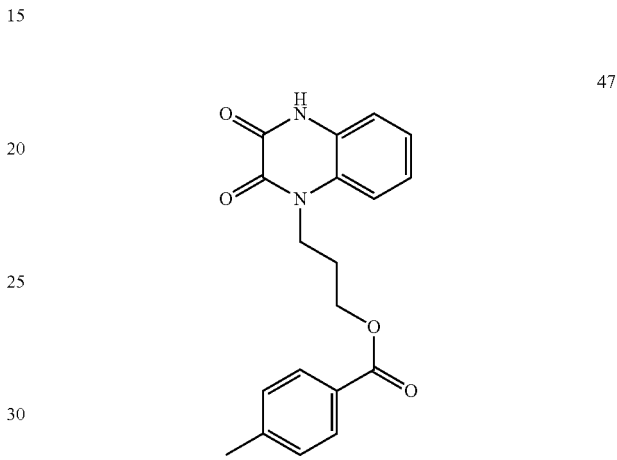

47

Compound 47 was synthesized as in Scheme 45.

Scheme 45

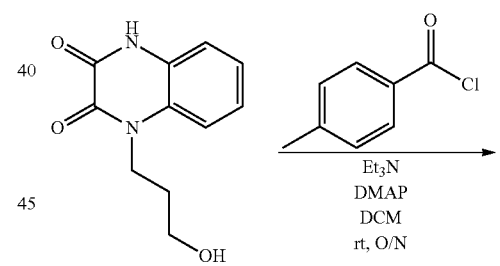

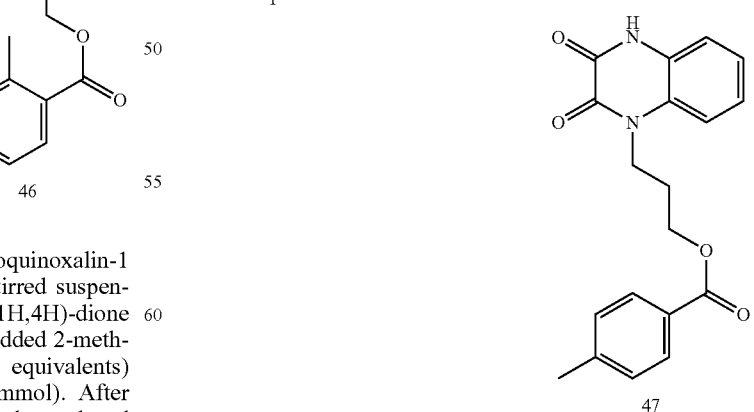

47

Preparation of 3-(2,3-dioxo-3,4-dihydroquinoxalin-1 (2H)-yl)propyl 4-methylbenzoate, 47. Following the procedure for 46 in Scheme 44 with 1-(3-hydroxypropyl)quinoxaline-2,3(1H,4H)-dione 1 (30 mg, 0.13 mmol), 4-methylbenzoyl chloride (50 mg, 0.32 mmol) and triethylamine (100 mg, 0.99 mmol) provided after product purification by column chromatography (eluted with a gradient of 0%→8% methanol in chloroform), and subsequent trituration with ether, 47 (40 mg, 91% yield) as white powder.

$^1$H NMR (600 MHz, DMSO-$d_6$) δ 12.02 (s, 1H), 7.82 (d J=8.2 Hz, 2H), 7.47-7.22 (m, 1H), 7.33 (d J=8.0 Hz, 2H), 7.21-7.15 (m, 3H), 4.34 (t, J=6.1 Hz, 2H), 4.31 (t, J=7.1 Hz, 2H), 2.39 (s, 3H), 2.11 (quintet, J=6.1 Hz, 2H). LC/MS: Eluent system D (retention time: 4.81 min); ESI-MS 339 [M+H]$^+$ and 337 [M−H]$^-$.

Compound 48

Synthesis of 3-(2,3-dioxo-3,4-dihydroquinoxalin-1(2H)-yl)propyl benzoate, 48

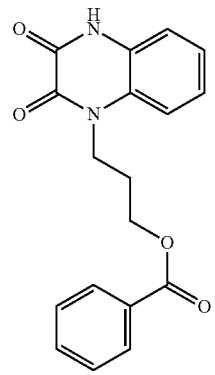

48

Preparation of 3-(2,3-dioxo-3,4-dihydroquinoxalin-1(2H)-yl)propyl benzoate, 48. Following the procedure for 46 in Scheme 44 with 1-(3-hydroxypropyl)quinoxaline-2,3(1H, 4H)-dione 1 (30 mg, 0.13 mmol), benzoyl chloride (50 mg, 0.36 mmol) and triethylamine (100 mg, 0.99 mmol) provided after purification by column chromatography (eluted with a gradient of 0%→8% methanol in chloroform), and subsequent trituration with ether, 48 (36 mg, 85% yield) as a white powder.

$^1$H NMR (600 MHz, DMSO-$d_6$) δ 12.03 (s, 1H), 7.92 (d J=8.3 Hz, 1H), 7.69-7.65 (m, 1H), 7.54-7.51 (m, 2H), 7.47-7.44 (m, 1H), 7.21-7.15 (m, 3H), 4.36 (t, J=6.0 Hz, 2H), 4.31 (t, J=7.0 Hz, 2H), 2.51 (s, 3H), 2.13 (quintet, J=6.8 Hz, 2H). LC/MS: Eluent system D (retention time: 3.69 min); ESI-MS 325 [M+H]$^+$ and 323 [M−H]$^-$.

Compound 49

Synthesis of 3-(2,3-dioxo-3,4-dihydroquinoxalin-1(2H)-yl)propyl 2-methoxybenzoate, 49

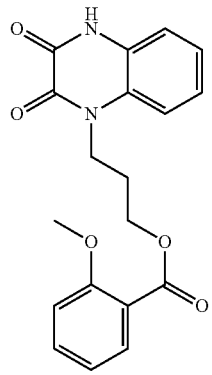

49

Compound 48 was synthesized as in Scheme 46.

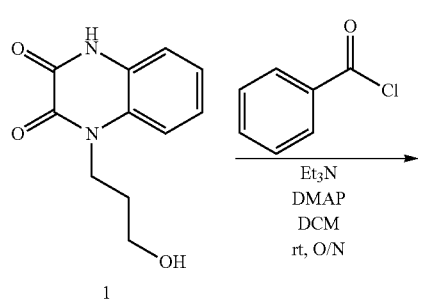

Scheme 46

Compound 49 was synthesized as in Scheme 47.

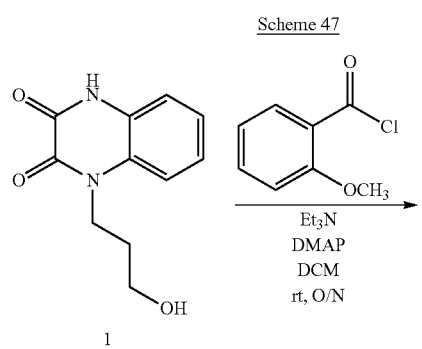

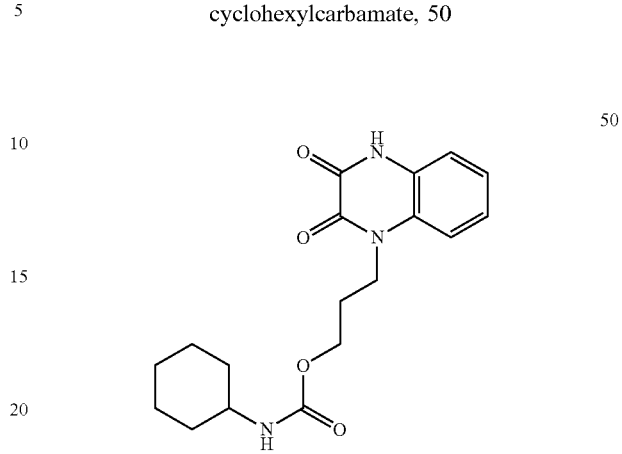

Compound 50

Synthesis of 3-(2,3-dioxo-3,4-dihydroquinoxalin-1(2H)-yl)propyl cyclohexylcarbamate, 50

Compound 50 was synthesized as in Scheme 48

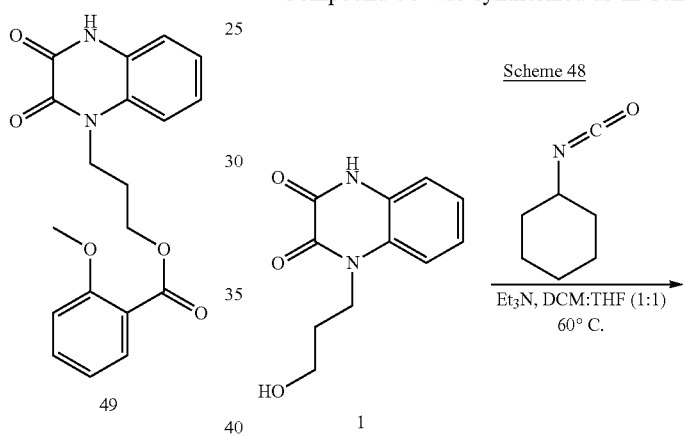

Preparation of 3-(2,3-dioxo-3,4-dihydroquinoxalin-1 (2H)-yl)propyl 2-methoxybenzoate, 49. Following the procedure for 46 in Scheme 44 with 1-(3-hydroxypropyl) quinoxaline-2,3(1H,4H)-dione 1 (30 mg, 013 mmol), 2-methoxybenzoyl chloride (50 mg, 0.29 mmol) and triethylamine (100 mg, 0.99 mmol) provided after purification by column chromatography (eluted with a gradient of 0%→8% methanol in chloroform), and subsequent trituration with ether, 49 (32 mg, 69% yield) as a white powder.

$^1$H NMR (600 MHz, DMSO-$d_6$) δ 12.02 (s, 1H), 7.66 (dd, J=1.8, 7.6 Hz, 1H), 7.56 (ddd, J=1.0, 7.5, 8.3 Hz, 1H), 7.46-7.43 (m, 1H), 7.21-7.14 (m, 4H), 7.03 (ddd, J=0.8, 7.3, 7.6 Hz, 1H), 4.32 (t, J=6.0 Hz, 2H), 4.28 (t, J=7.0 Hz, 2H), 3.83 (s, 3H), 2.06 (quintet, J=7.2 Hz, 2H). LC/MS: Eluent system D (retention time: 2.99 min); ESI-MS 355 [M+H]$^+$ and 353 [M−H]$^-$.

Preparation of 3-(2,3-dioxo-3,4-dihydroquinoxalin-1 (2H)-yl)propyl cyclohexylcarbamate, 50. A mixture of 1-(3-hydroxypropyl)-1,4-dihydroquinoxaline-2,3-dione 1 (40 mg, 0.18 mmol), cyclohexyl isocyanate (29.6 mg, 0.24 mmol), and Et$_3$N (38.0 μL, 0.27 mmol) in anhydrous DCM: THF (1:1, 5.0 mL) was heated in an oil bath at 60° C. After 3 h, the reaction was cooled to room temperature and concentrated under reduced pressure. The product was purified by column chromatography on silica gel (Biotage®, 12 g Silicycle column, eluted with gradient of 0 to 4% methanol in chloroform), which afforded 50 (45.2 mg, 72% yield) as an off-white solid.

$^1$H NMR (600 MHz, DMSO-d$_6$) δ 12.02 (s, 1H), 7.38 (dd, J=3.4, 5.8 Hz, 1H), 7.22-7.16 (m, 3H), 7.11 (d, J=7.9 Hz, 1H), 4.16 (t, J=7.2 Hz, 2H), 4.03 (t, J=6.1 Hz, 2H), 3.28-3.19 (m, 1H), 1.97-1.85 (m, 2H), 1.79-1.71 (m, 2H), 1.71-1.63 (m, 2H), 1.61-1.47 (m, 1H), 1.31-0.97 (m, 5H). LC/MS: Eluent system D (retention time: 3.96 min); ESI-MS: 344 [M−H]$^-$.

Figure 2:
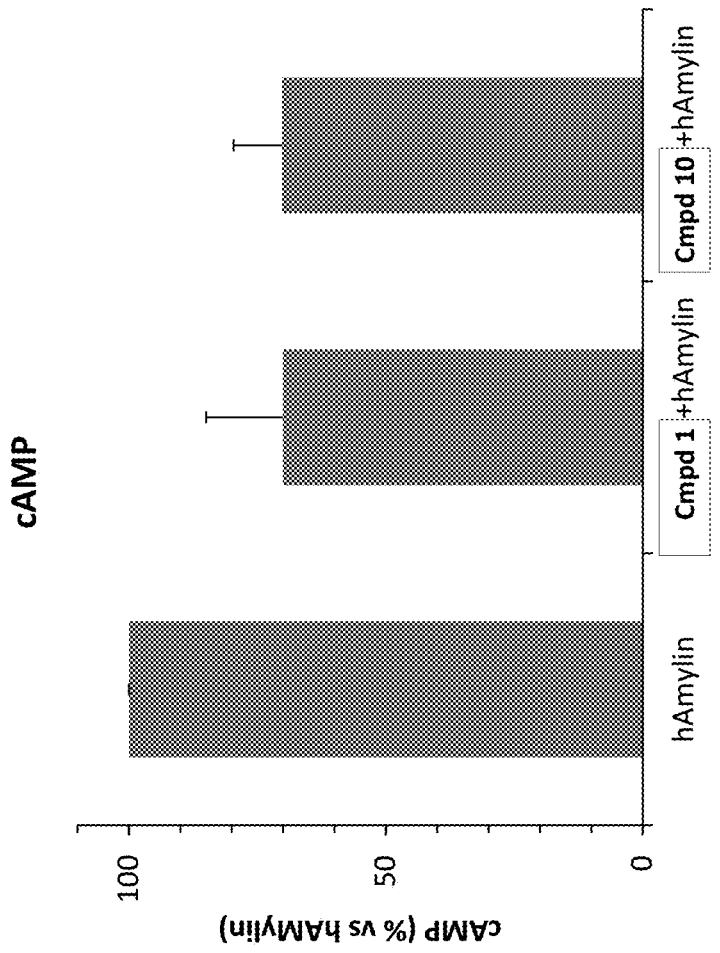
FIG. 2: Human amylin (0.1 μM) generation of cAMP was attenuated in the presence of Compounds 1 and 10 (10 μM)

Example 2: Testing of Compounds for Reduction of Camp in the Presence of Human Amylin Compounds described herein were screened using a cAMP (cyclic adenosine monophosphate) assay in amylin receptor subtype 3 expressing cells (See FIG. 1). Screening of Compound 1 and Compound 10 using cAMP assays in amylin receptor subtype 3 expressing cells indicated that they were amylin receptor antagonists. See FIG. 2.

Cell Cultures. Amylin receptor subtypes (AMY3-HEK cells) stably expressed in human embryonic kidney (HEK293) cell-line were generated and characterized as described in a previous published article (Fu et al., *J. Biol. Chem.* 2012). The AMY3-HEK cells were grown in a 5% CO$_2$ humidified incubator at 37° C. with DMEM, 10% FBS, and 100 µg/mL Zeocin medium.

ELISA (enzyme-linked immunosorbent assay). Cellular cAMP levels were measured using a parameter cyclic AMP assay kit (R&D Systems) according to the manufacturer's instructions. Briefly, AMY3-HEK cells were plated on 24-well plates overnight. These cells were then incubated with or without the assay compounds and hAmylin for 5 min. The cells were lysed with lysis buffer provided in the assay kit. Standard curves were plotted using the cAMP standards provided in the ELISA kits. All samples were analyzed in duplicate. The plate was measured at 450 nm. Data was plotted, and non-linear regression was fitted with four parameters using Prism software (GraphPad Software, La Jolla, CA).

Compounds were assayed based on potency of reduction at 10 µM of 0.1 µM human Amylin (hAmylin) induced cAMP increases.

Example 3: Compound 1 and 10 Attenuated Elevations in Intracellular Calcium Evoked by Human Amylin Kinetic Intracellular Ca$^{2+}$ Changes. Dynamic changes of the free cytosolic Ca2+ concentration were monitored with microplate reader. For monitor amylin induced intracellular Ca$^{2+}$, AMY3-HEK293 cells were plated on 96 well cell culture plates and incubated at 37° C. for 12-36 h with DMEM, 10% FBS, and Zeocin medium. For Ca$^{2+}$ changes, the AMY3-HEK293 cells were washed twice with assay solution which ion content similar to extracellular brain fluid thus containing the following: 130 mM NaCl, 4 mM KCl, 1 mM MgCl$_2$, 2 mM CaCl$_2$), 10 mM HEPES, and 10 mM glucose (pH 7.35). Then incubated with the membrane-permeant fluorescent Ca$^{2+}$-sensitive dye Fluo-8L-AM (AAT Bioquest, Inc., Sunnyvale, CA), with 5 µM of the agent for 40 min at room temperature (20-23° C.) in assay solution. The test compounds were added in various concentrations of 0.01, 0.1, 1, and 10 µM for 10 min and kinetic measured the fluorescent intensity with Varioskan-LUX microplate reader (Thermo Fisher Scientific, Waltham, MA). Human amylin were dissolved in sterile bidistilled water at 1 mM stock solution and incubated at room temperature for 10 min before dilution with assay solution for use at a final concentration of 0.5 µM. Fluorescent intensity was measured at excitation/emission wavelength of 488/514 nm, excitation bandwidth 12 nm, kinetic interval 1 min, and measure time at 100 ms.

Figure 3:
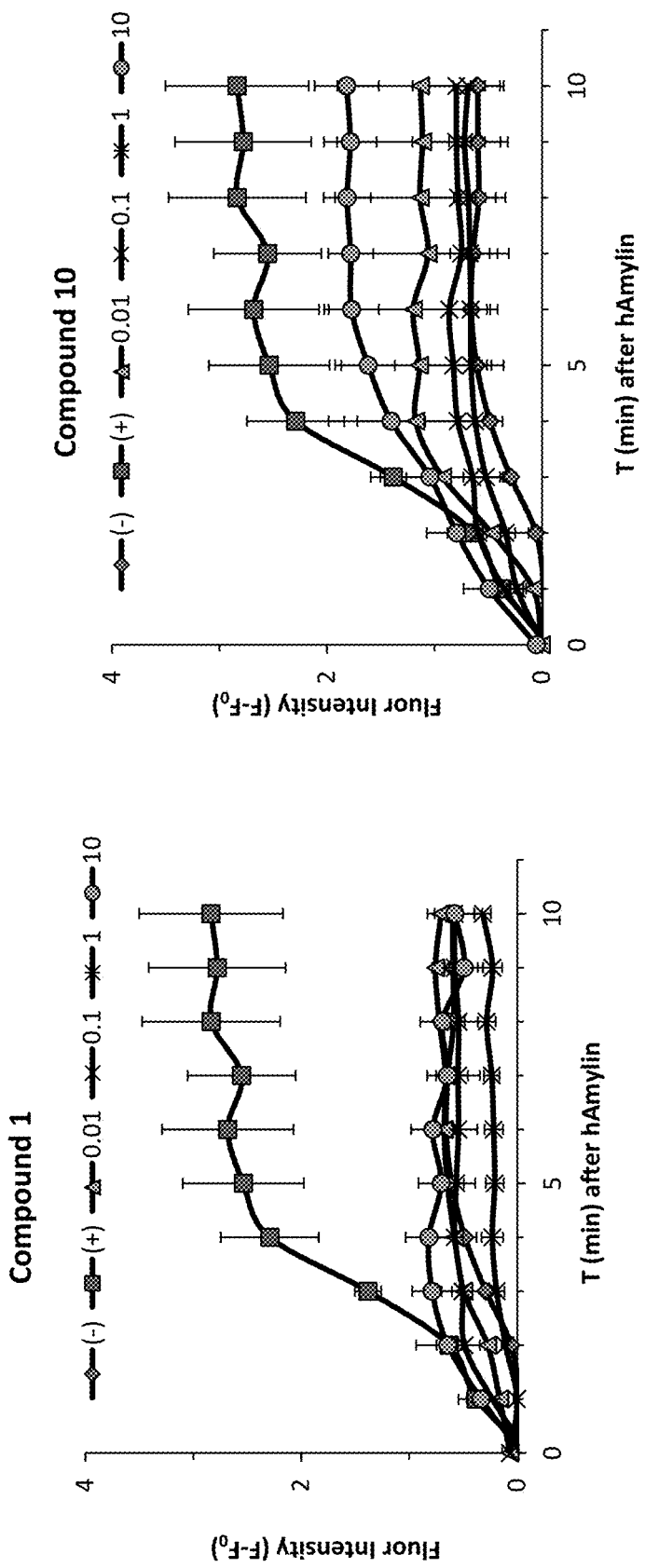
FIG. 3: Compound 1 and 10 (0.01-10 μM range) attenuated elevations in intracellular calcium evoked by application of human amylin (0.5 μM). Fluor-8 is a fluorescent membrane permeable calcium dye that fluoresces upon elevation of intracellular calcium levels due to ligand activation of receptors (such as human amylin).

Compounds 1 and 10 were examined for their ability to alter intracellular calcium levels in AMY3-HEK cells using this method as shown in FIG. 3.

Example 4: Compound 1 and 10 Reduced Human Amylin and Amyloid Beta Induced Cytotoxicity in Neuronal Cells MTT Cell Death Assay. The N2a (mouse) and SK-N-SH (human) neuronal cells were seeded to 5000 cells/well in a 96-well plate in DMEM medium, 10% FBS and incubated overnight. Cells in culture medium were incubated either with or without the assay compounds and Aβ$_{1-42}$, 10 µM for 24-48 h. At the end of treatment, 20 µL of 5 mg/mL 3-(4,5-dimethylthiazol-2-yl)-2,5-diphenyltetrazolium bromide (MTT, Sigma) was added to each well and incubated at 37° C. for 3 h. Medium was removed, 100 µL of MTT solvent (isopropanol with 4 mM HCl) was added to each well, and the plates were incubated for 30 min at room temperature on a rotating shaker. Plates were analyzed on a microplate reader at a 562 nm wavelength.

Figure 4:
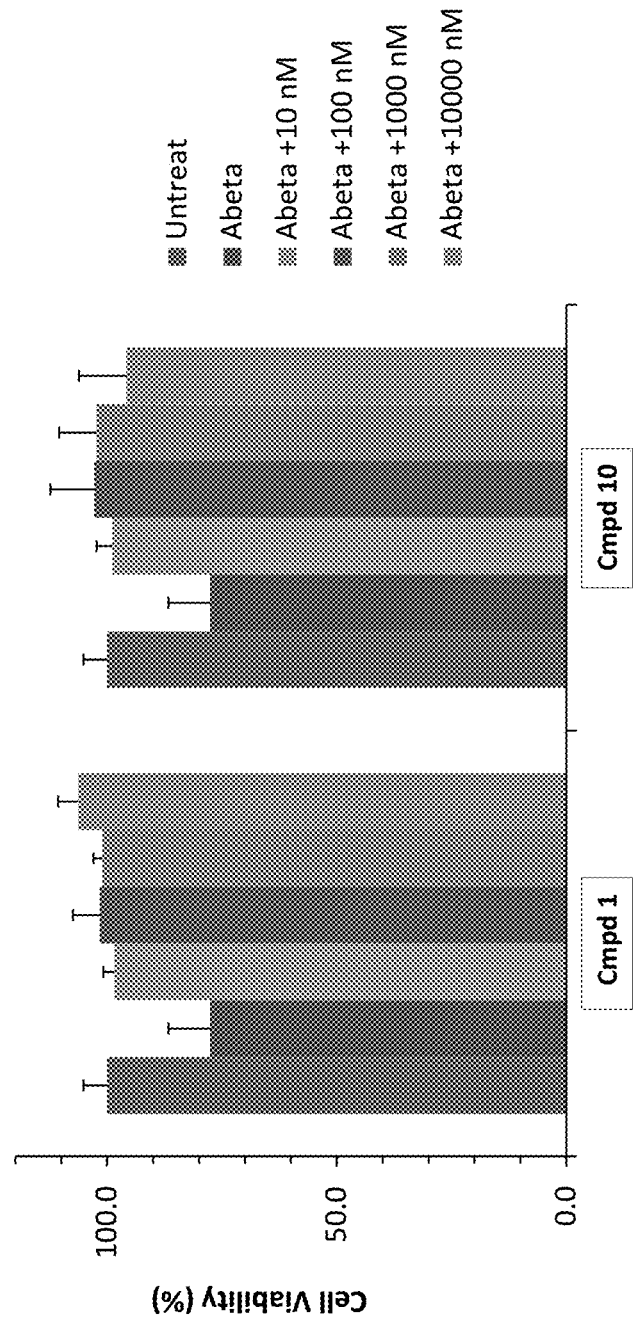
FIG. 4: Compounds 1 and 10 were cytoprotective against amyloid beta (Abeta) toxicity in a neurons cell line (N2a). MTT cell assay measured cell viability. Abeta was prepared and applied as a soluble oligomeric species described in the literature, such as in Soudy, R. et al Alzheimer's & Dementia: Translational Research & Clinical Interventions (2017).

Compounds 1 and 10 were cytoprotective against amyloid beta (Abeta) toxicity in a neurons cell line (N2a) using the MTT cell assay to measure cell viability. See FIG. 4.

Example 5: Compound 1 and 10 Increased Hippocampal Long Term Potentiation (LTP)

Hippocampal long term potentiation (LTP) electrophysiology experiments: an in vitro cellular surrogate for memory. Brains were quickly removed from mice following decapitation, placed in a cold artificial cerebral spinal fluid (aCSF) on a vibratome chamber and transverse sections cut through the hippocampus. The aCSF contained (in mM) 124 NaCl, 3 KCl, 2.4 CaCl$_2$), 2 MgCl$_2$, 1.25 NaH$_2$PO$_4$, 26 NaHCO$_3$ and 10 D-glucose, and was equilibrated with 95% 02 and 5% CO$_2$. Hippocampal slices (400 m thick) were maintained in aCSF-filled holding chamber at room temperature for at least 1 hour and individually transferred to the submerged glass bottom recording chamber, which was constantly perfused with aCSF (2 mL/min) at 30° C. Field excitatory postsynaptic potential (fEPSP) was recorded with a metallic (Pt/Ir) electrode (FHC, Bowdoin, ME) from the stratum radiatum layer of Cornu ammonis 1 region of the hippocampus (CA1) area, and the Schaffer collateral afferents were stimulated with 100-µs test pulses via a bipolar cluster electrode (FHC) (Kimura et al., 2012, Kimura et al. 2016). To evaluate basal synaptic transmission, we applied different stimulation strengths (75 µA to 300 µA in steps of 25 µA) and plotted the amplitudes of presynaptic fiber volleys versus the corresponding fEPSP slopes to compare the slope of input/output (I/O) curves of fEPSP. For long-term potentiation (LTP) experiments, the stimulus strength was set to elicit 40-50% of the maximum fEPSP amplitude and test pulses were delivered to Schaffer collaterals once every 30 seconds. LTP was induced by 3-theta-burst stimulation (3-TBS) protocol (each burst consisted of 4 pulses at 100 Hz with a 200-ms inter-burst interval). Before 3-TBS or drug application, the responses were monitored for at least 10 minutes to ensure a stable baseline of fEPSP. To determine whether the magnitude of LTP differed significantly between groups, average responses during the last 20-min block of recordings (40-60 min after TBS) were compared. Results were from various treatment groups were plotted as histograms with means±standard error (SE). Statistical analysis was performed using one-way ANOVA followed by post-hoc Tukey's honestly significant difference (HSD) test (for multiple comparisons) or Student's t test (for pair-wise comparisons). All drugs and chemicals were applied directly to the slice via bath perfusion, which allowed for a complete exchange of the perfusate in less than a minute and a half.

Figure 5A:
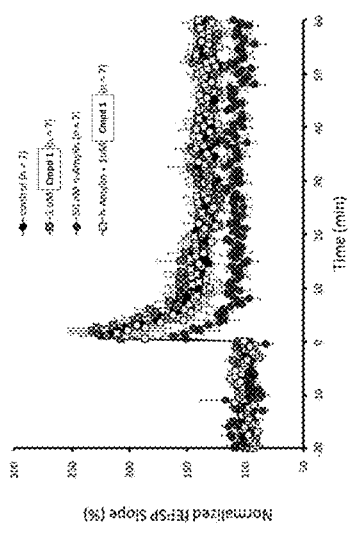
FIGS. 5A to 5C: LTP data for Compound 1, which blocked human Amylin and Amyloid beta induced LTP responses. Compound 1 also restored LTP in transgenic (Tg_Cont) AD mice to levels comparable to those in age-matched wild type controls.
Figure 5B:
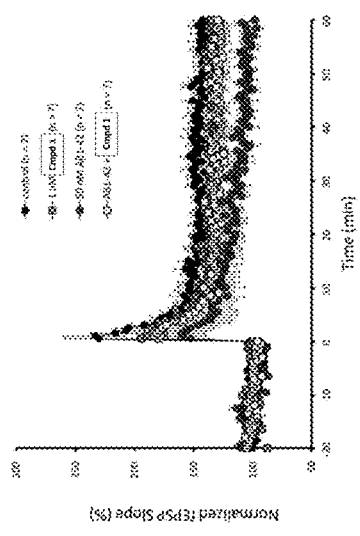
Figure 5C:
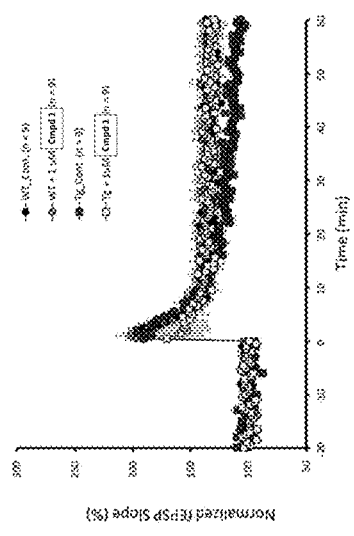
Figure 6A:
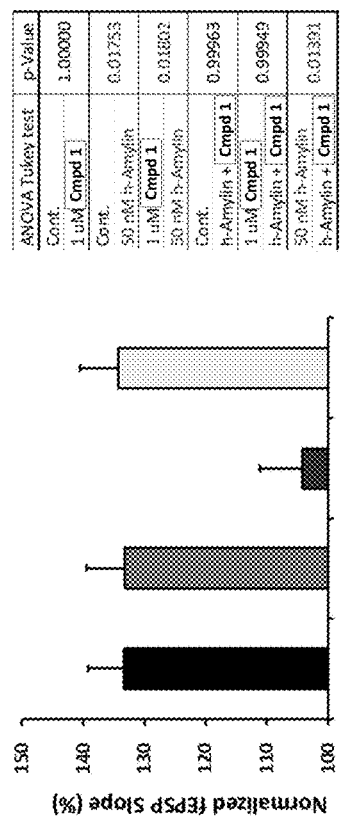
FIGS. 6A to 6C: Histograms depicting summary data of LTP responses from experimental data shown in FIG. 5. Right panels show statistical treatment of the data using one-way ANOVA followed Tukey's test. Both human amylin- and Aβ-induced LTP responses were blocked by Compound 1 and the chronically reduced LTP levels in transgenic transgenic AD mice (Tg_Cont) were restored by applications of Compound 1 to levels comparable to age matched wild type control mice (WT_Cont). Compound 1 had no effects on LTP from WT_Cont mice.
Figure 6B:
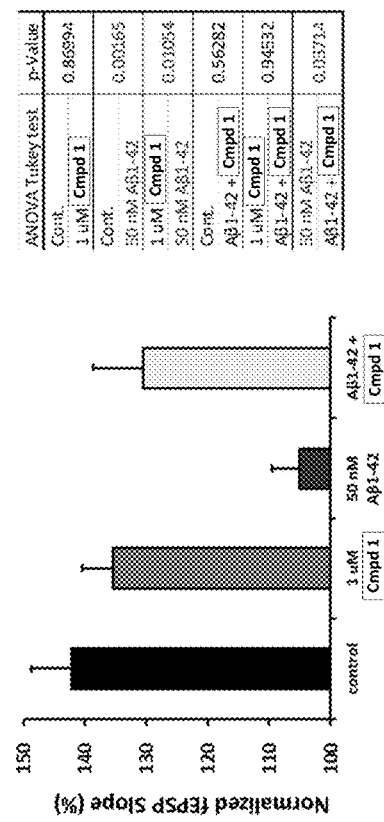
Figure 6C:
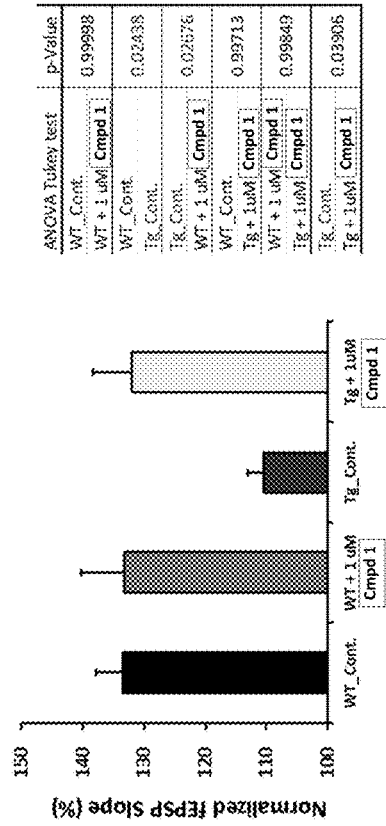
Figure 7A:
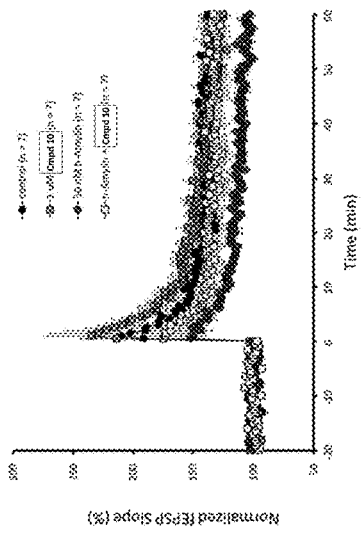
FIGS. 7A to 7C: LTP data for Compound 10, which blocked human Amylin and Amyloid beta induced LTP responses. Compound 10 also restored LTP in transgenic (Tg_Cont) AD mice to levels comparable to those in age-matched wild type controls.
Figure 7B:
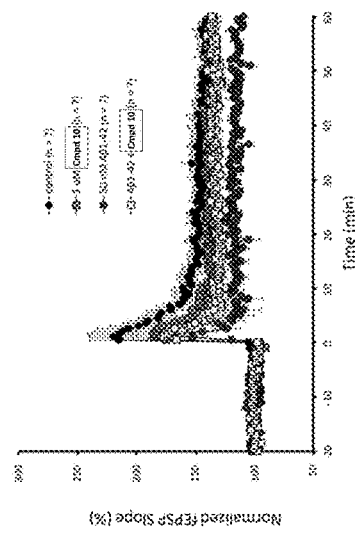
Figure 7C:
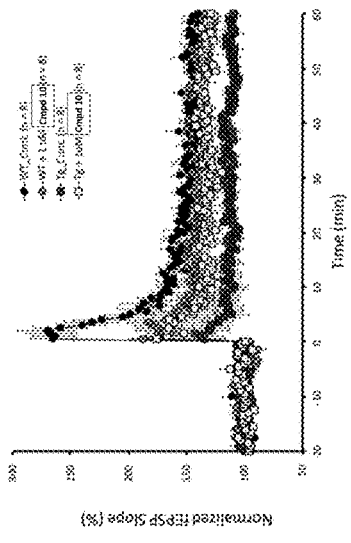
Figure 8A:
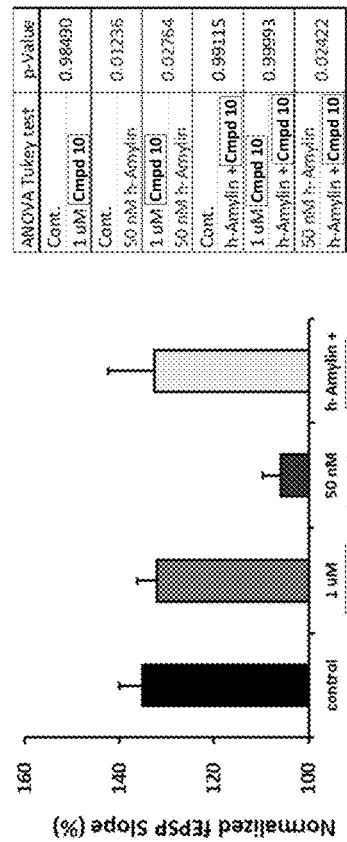
FIGS. 8A to 8C: Histograms depicting summary data of LTP responses from experimental data shown in FIG. 5. Right panels show statistical treatment of the data using one-way ANOVA followed Tukey's test. Both human amylin- and Aβ-induced LTP responses were blocked by Compound 10 and the chronically reduced LTP levels in transgenic transgenic AD mice (Tg_Cont) were restored by applications of Compound 10 to levels comparable to age matched wild type control mice (WT_Cont). Compound 10 had no effects on LTP from WT_Cont mice.
Figure 8B:
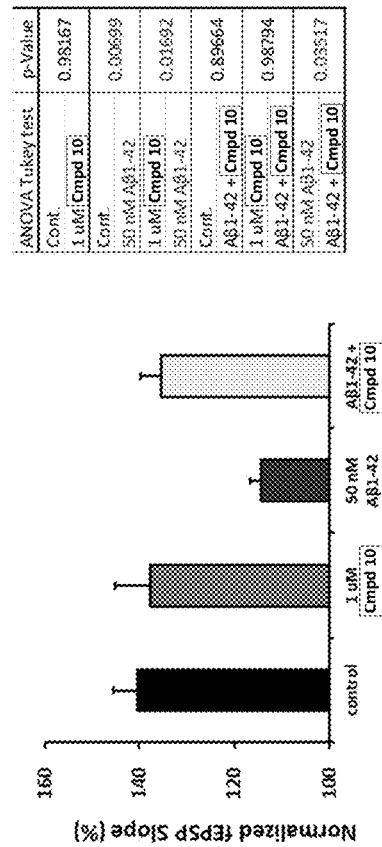
Figure 8C:
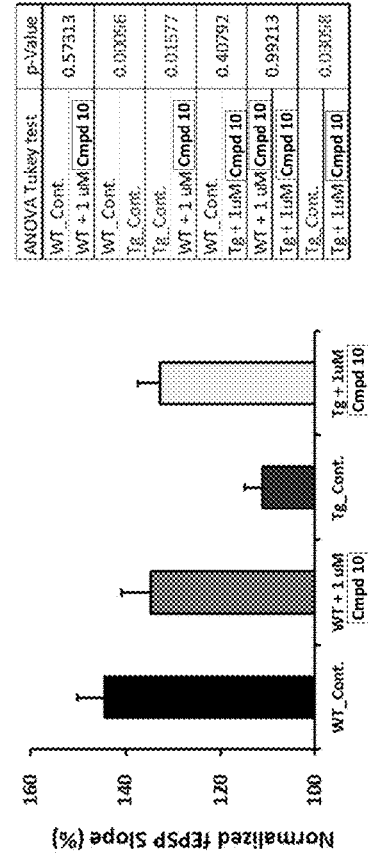

LTP is a cellular surrogate of memory. In brain hippocampal slices, Compound 1 application at 1 µM blocked human amylin- and amyloid beta (Aβ)-induced depression of LTP (FIGS. 5A and 5B, FIGS. 6A and 6B). In hippocampal brain slices from transgenic AD mice (TgCRND8), LTP was chronically depressed. Application of Compound 1 increased LTP levels (FIGS. 5C and 6C) to levels close to those observed for wild type, age matched control (WT_Cont) mice. Similarly, application of Compound 10 at 1 µM blocked human amylin- and amyloid beta (Aβ)-induced depression of LTP (FIGS. 7A and 7B, FIGS. 8A and 8B). Additionally, in AD mice (TgCRND8) Compound 10 also increased LTP levels to levels observed in WT_Cont mice (FIG. 7C and FIG. 8C).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating Alzheimer's disease, the method comprising:
   administering to a subject in need thereof, a therapeutically effective amount of a compound of formula (I):

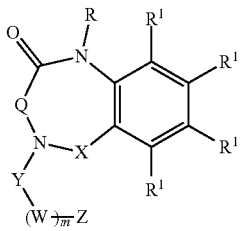

(I)

wherein:
R is selected from the group consisting of —H, $C_1$-$C_6$-alkyl, and substituted $C_1$-$C_6$-alkyl;
each $R^1$ is independently selected from the group consisting of H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;
each $R^2$ is independently selected from the group consisting of —H, $C_1$-$C_6$-alkyl, and substituted $C_1$-$C_6$-alkyl;
each W is selected from the group consisting of —$CH_2$—, —$CHR^3$— and —$CR^3R^4$—;
$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo;
m is selected from 1, 2 or 3;
Q is —C(=O)—;
X is absent;
Y is selected from the group consisting of —$CH_2$—, and —C(=O)—;
Z is selected from the group consisting of —$OR^5$, halogen, —CN, —$NR^5R^5$, —NHC(=O)$R^5$, —NHC(=O)$NR^5R^5$, aryl, and heteroaryl; and
each $R^5$ is independently selected from the group consisting of —H, $C_1$-$C_6$-alkyl, substituted $C_1$-$C_6$-alkyl, aryl, substituted aryl, heteroaryl, and substituted heteroaryl;
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

2. The method of claim 1, wherein the administering comprises contacting an amylin receptor with the compound.

3. The method of claim 2, wherein the amylin receptor is an AMY3 receptor.

4. The method of claim 1, wherein the compound is of formula (II):

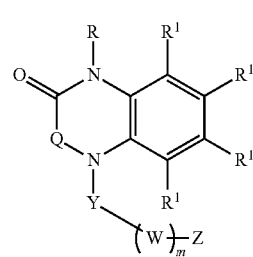

(II)

wherein:
R is selected from the group consisting of —H and $C_1$-$C_6$-alkyl;
each $R^1$ is independently selected from the group consisting of —H, halogen, $C_1$-$C_6$-alkyl, substituted $C_1$-$C_6$-alkyl, $C_3$-$C_6$-cycloalkyl, substituted $C_3$-$C_6$-cycloalkyl, —$OR^2$, heterocyclyl, substituted heterocyclyl, aryl, substituted aryl, heteroaryl, and substituted heteroaryl;
each $R^2$ is independently selected from the group consisting of —H, and $C_1$-$C_6$-alkyl;
each W is selected from the group consisting of —$CH_2$—, —$CHR^3$— and —$CR^3R^4$—;
$R^3$ and $R^4$ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together $R^3$ and $R^4$ comprise a carbocycle, substituted carbocycle or oxo;
m is selected from 1, 2 or 3;
Q is —C(=O)—;
Y is selected from the group consisting of —$CH_2$—, and —C(=O)—;
Z is selected from the group consisting of —$OR^5$, -halogen, —$NR^5R^5$, —NHC(=O)$R^5$, —NHC(=O)$NR^5R^5$, aryl, and heteroaryl; and each R⁵ is independently selected from the group consisting of —H, $C_1$-$C_6$-alkyl, substituted $C_1$-$C_6$-alkyl, aryl, substituted aryl, heteroaryl, and substituted heteroaryl;
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

5. The method of claim 1, wherein the compound is of formula (III):

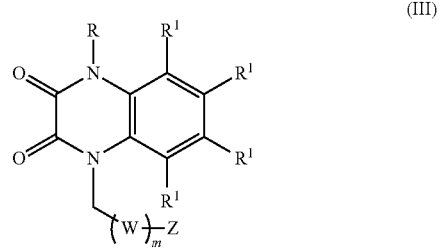

wherein:
R is selected from the group consisting of —H and $C_1$-$C_6$-alkyl;
each R¹ is independently selected from the group consisting of —H, halogen, $C_1$-$C_6$-alkyl, substituted $C_1$-$C_6$-alkyl, $C_3$-$C_6$-cycloalkyl, substituted $C_3$-$C_6$-cycloalkyl, —OR², heterocyclyl, substituted heterocyclyl, aryl, substituted aryl, heteroaryl, and substituted heteroaryl;
each R² is independently selected from the group consisting of —H, and $C_1$-$C_6$-alkyl;
each W is selected from the group consisting of —CH₂—, —CHR³— and —CR³R⁴—;
R³ and R⁴ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heterocyclyl, substituted heterocyclyl, aryl, substituted aryl, heteroaryl, substituted heteroaryl, fused-heterocycle, and substituted fused-heterocycle, or together R³ and R⁴ comprise a carbocycle, substituted carbocycle or oxo;
m is selected from 1, 2 or 3;
Z is selected from the group consisting of —OR⁵, halogen, —NR⁵R⁵, —NHC(=O)R⁵, —NHC(=O)NR⁵R⁵, aryl, and heteroaryl; and
each R⁵ is independently selected from the group consisting of —H, $C_1$-$C_6$-alkyl, substituted $C_1$-$C_6$-alkyl, aryl, substituted aryl, heteroaryl, and substituted heteroaryl;
or an enantiomer, a mixture of enantiomers, a mixture of two or more diastereomers, a tautomer, a mixture of two or more tautomers, or an isotopic variant thereof;
or a pharmaceutically acceptable salt, solvate, or hydrate thereof.

6. The method of claim 5, wherein R is —H or —CH₃.
7. The method of claim 5, wherein each R¹ is selected from —H, —CH₃, —CF₃, —F, —Cl and heteroaryl.
8. The method of claim 7, wherein each R¹ is selected from —H, —CH₃, —CF₃, —F, —Cl and pyridyl.
9. The method of claim 8, wherein R¹ is —H.
10. The method of claim 5, wherein m is 1.
11. The method of claim 5, wherein m is 2.
12. The method of claim 5, wherein R³ and R⁴ are independently selected from the group consisting of halogen, $C_1$-$C_6$-alkyl, substituted $C_1$-$C_6$-alkyl, $C_3$-$C_6$-cycloalkyl, substituted $C_3$-$C_6$-cycloalkyl, heteroaryl, substituted heteroaryl, fused-heterocycle, and substituted fused-heterocycle, or together R³ and R⁴ comprise a $C_3$-$C_6$ carbocycle, substituted $C_3$-$C_6$ carbocycle or oxo.

13. The method of claim 12, wherein R³ and R⁴ are independently selected from the group consisting of —F, —Cl, —CH₃, or together R³ and R⁴ comprise a cyclopropyl, cyclobutyl, cyclopentyl or oxo.

14. The method of claim 5, wherein W is selected from —CH₂— and —CHR³—.

15. The method of claim 14, wherein W is —CH₂—.

16. The method of claim 5, wherein Z is selected from the group consisting of —OR⁵, —F, —NHC(=O)R⁵, and heteroaryl.

17. The method of claim 16, wherein Z is selected from the group consisting of —OR⁵, and —NHC(=O)R⁵.

18. The method of claim 5, wherein each R⁵ is independently selected from —H, —CH₃, —CH₂CH₃, —CH(CH₃)₂ and phenyl.

19. The method of claim 18, wherein each R⁵ is independently selected from —H, and —CH₃.

20. The method of claim 1, wherein the compound is selected from the group consisting of:

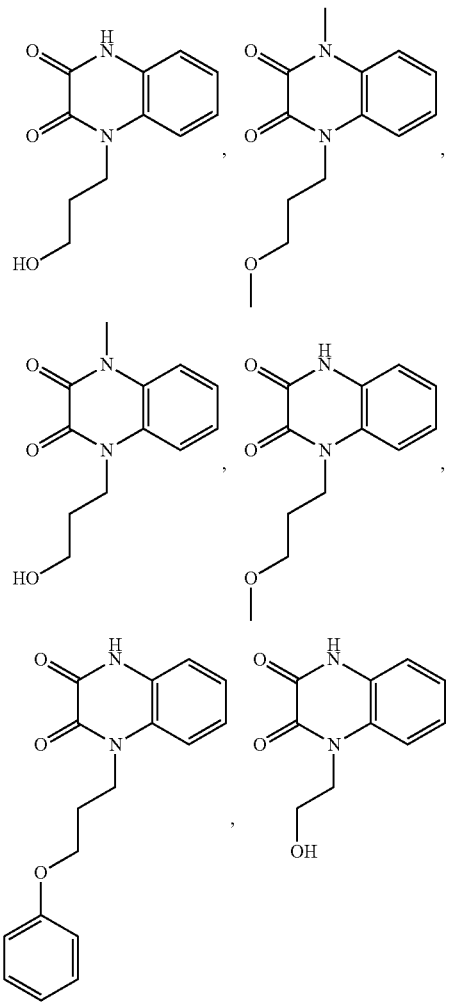

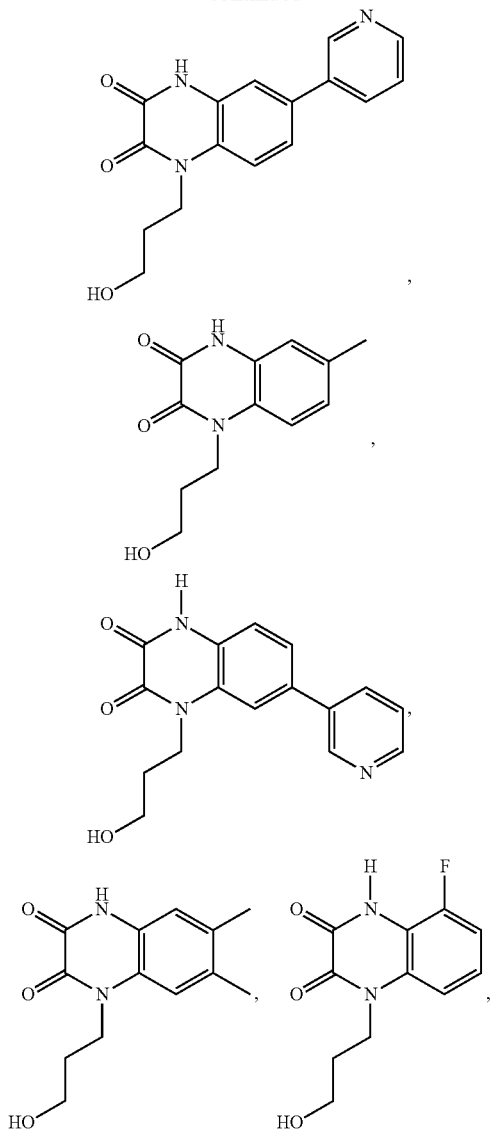
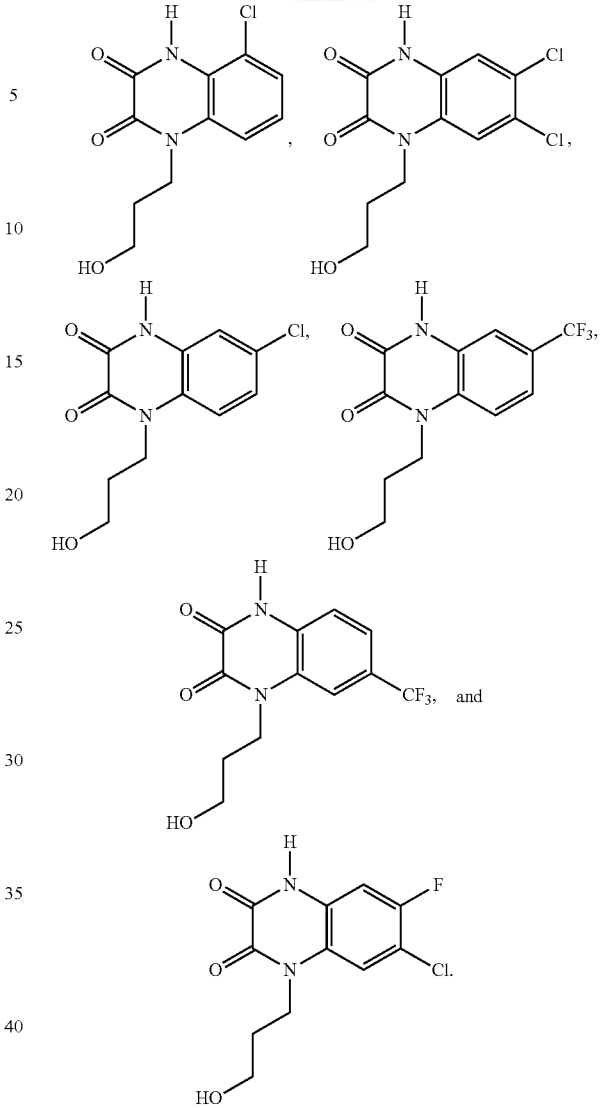
* * * * *